United States Patent

Rawson et al.

[11] Patent Number: 6,017,945
[45] Date of Patent: Jan. 25, 2000

[54] INDOLE DERIVATIVES USEFUL AS ENDOTHELIN RECEPTOR ANTAGONISTS

[75] Inventors: David James Rawson; Kevin Neil Dack; Roger Peter Dickinson; Kim James, all of Sandwich, United Kingdom

[73] Assignee: Pfizer Inc., New York, N.Y.

[21] Appl. No.: 09/147,096

[22] PCT Filed: Apr. 11, 1997

[86] PCT No.: PCT/EP97/01882

§ 371 Date: Oct. 5, 1998

§ 102(e) Date: Oct. 5, 1998

[87] PCT Pub. No.: WO97/43260

PCT Pub. Date: Nov. 20, 1997

[30] Foreign Application Priority Data

May 9, 1996 [GB] United Kingdom .................. 9609641

[51] Int. Cl.[7] .......................... A61K 31/40; C07D 405/02
[52] U.S. Cl. .......................... 514/414; 514/415; 514/419; 548/454; 548/455; 548/494; 548/495; 548/496
[58] Field of Search .................. 514/414, 415, 514/419; 548/454, 455, 494, 495, 496

[56] References Cited

FOREIGN PATENT DOCUMENTS

92/04321 3/1992 WIPO .

*Primary Examiner*—Joseph K. McKane
*Assistant Examiner*—John F. Dolan
*Attorney, Agent, or Firm*—Peter C. Richardson; Gregg C. Benson; Carl J. Goddard

[57] ABSTRACT

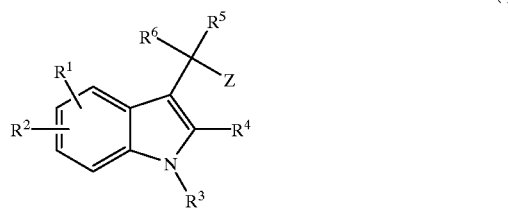

Compounds of formula (I), and their pharmaceutically acceptable derivatives, wherein $R^1$ and $R^2$ are optional substituents and independently represent $C_{1-6}$ alkyl, $C_{2-6}$ alkenyl [optionally substituted by $CO_2H$ or $CO_2(C_{1-6}$ alkyl)], $C_{2-6}$ alkynyl, halogen, $C_{1-3}$ perfluoroalkyl, $(CH_2)_mAr^1$, $(CH_2)_mHet^1$, $(CH_2)_mCONR^7R^8$, $(CH_2)_mCO_2R^8$, $O(CH_2)_qCO_2R^8$, $(CH_2)_mCOR^8$, $(CH_2)_mOR^8$, $O(CH_2)_pOR^8$, $(CH_2)_mNR^7R^8$, $CO_2(CH_2)_qNR^7R^8$, $(CH_2)_mCN$, $S(O)_nR^8$, $SO_2NR^7R^8$, $CONH(CH_2)_mAr^1$ or $CONH(CH_2)_mHet^1$; $R^3$ represents H, $C_{1-6}$ alkyl, $(CH_2)_pNR^9R^{10}$, $SO_2R^{10}$, $SO_2NR^9R^{10}$, $(CH_2)_mCOR^{10}$, $C_{2-6}$ alkenyl, $C_{2-6}$ alkynyl, $(CH_2)_mCONR^9R^{10}$, $(CH_2)_mCO_2R^{10}$, $(CH_2)_pCN$, $(CH_2)_pR^{10}$ or $(CH_2)_pOR^{10}$; $R^4$ represents H or $C_{1-6}$ alkyl; $R^5$ represents H or OH; $R^6$ represents phenyl optionally fused to a heterocyclic ring, the group as a whole being optionally substituted; $R^{7-10}$ are fully defined herein and may independently represent $Ar^2$ or $Het^2$; Z represents $CO_2H$, $CONH$(tetrazol-5-yl), $CONHSO_2O(C_{1-4}$ alkyl), $CO_2Ar^3$, $CO_2(C_{1-6}$ alkyl), tetrazol-5-yl, $CONHSO_2Ar^3$, $CONHSO_2(CH_2)_qAr^3$ or $CONHSO_2(C_{1-6}$alkyl); $Ar^{1-3}$ independently represent phenyl, naphthyl, or an aromatic heterocycle, which groups are optionally fused and optionally substituted; and $Het^1$ and $Het^2$ independently represent a non-aromatic heterocycle which is optionally substituted; are useful in the treatment of restenosis, renal failure and pulmonary hypertension.

11 Claims, No Drawings

INDOLE DERIVATIVES USEFUL AS ENDOTHELIN RECEPTOR ANTAGONISTS

CROSS REFERENCE TO RELATED APPLICATIONS

This application is the National Stage filing under 35 U.S.C. §371 based on PCT/EP97/01882 which was filed internationally on Apr. 11, 1997.

This invention relates to indole derivatives useful in the treatment of a variety of diseases including restenosis, renal failure and pulmonary hypertension, and to pharmaceutical formulations containing such compounds.

International Patent Application WO 94/14434 discloses indole derivatives which are indicated as endothelin receptor antagonists. European Patent Application 617001 discloses a large number of phenoxyphenylacetic acid derivatives which are also indicated as endothelin receptor antagonists.

Bergman et al. Tetrahedron. Vol 31. N° 17, 1975, pages 2063–2073, disclose a number of indole-3-acetic acids. Similar compounds are disclosed by Rusinova et al. Khim Geterotsikl Soedin, 1974, (2), 211–213 (see also Chemical Abstracts, Vol 81, N° 7, 19 August 1974, abstract N° 37455a). and Yarovenko et al. J Gen Chem USSR (English translation), Vol 39, 1969, page 2039 (see also Beilstein, Registry Number 431619). These compounds are not indicated in any kind of therapy, and proviso (i) below relates to them.

Julian et al. J Chem Soc. Chemical Communications. N° 1, 1973, disclose an N-p-chlorobenzoylindole derivative as a by-product of a photo-addition reaction. The compound is not indicated in any kind of therapy, and proviso (ii) below relates to it.

Yamamoto et al. Japanese Patent N° 70 041 381 (see also Chemical Abstracts. Vol 75. N° 3, 1971. abstract N° 20189v), disclose an N-p-chlorobenzoylindole derivative which is indicated as an anti-inflammatory. Proviso (iii) below relates to it.

According to the present invention, there is provided a compound of formula I.

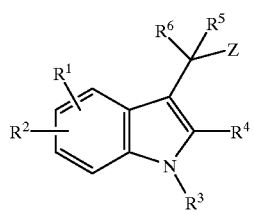

wherein
$R^1$ and $R^2$ are optional substituents and independently represent $C_{1-6}$ alkyl, $C_{2-6}$ alkenyl [optionally substituted by $CO_2H$ or $CO_2(C_{1-6}$ alkyl)], $C_{2-6}$ alkynyl, halogen, $C_{1-3}$ perfluoroalkyl, $(CH_2)_mAr^1$, $(CH_2)_mHet^1$, $(CH_2)_mCONR^7R^8$, $(CH_2)_mCO_2R^8$, $O(CH_2)_qCO_2R^8$, $(CH_2)_mCOR^8$, $(CH_2)_mOR^8$, $O(CH_2)_pOR^8$, $(CH_2)_mNR^7R^8$, $CO_2(CH_2)_qNR^7R^8$, $(CH_2)_mCN$, $S(O)_nR^8$, $SO_2NR^7R^8$, $CONH(CH_2)_mAr^1$ or $CONH(CH_2)_mHet^1$;

$R^3$ represents H, $C_{1-6}$ alkyl, $(CH_2)_pNR^9R^{10}$, $SO_2R^{10}$, $SO_2NR^9R^{10}$, $(CH_2)_mCOR^{10}$, $C_{2-6}$ alkenyl, $C_{2-6}$ alkynyl, $(CH_2)_mCONR^9R^{10}$, $(CH_2)_mCO_2R^{10}$, $(CH_2)_pCN$, $(CH_2)_pR^{10}$ or $(CH_2)_pOR^{10}$;

$R^4$ and $R^9$ independently represent H or $C_{1-6}$ alkyl;

$R^7$ represents H, $C_{1-6}$ alkyl or $C_{1-6}$ alkoxy;

$R^5$ represents H or OH;

$R^6$ represents phenyl optionally fused to a saturated or unsaturated 5- or 6-membered heterocyclic ring containing 1 or 2 heteroatoms selected from N, S and O, the group as a whole being optionally substituted by one or more groups selected from $C_{1-6}$ alkyl, $C_{1-6}$ alkoxy and halogen, and wherein any members of the heterocyclic ring which are S may be substituted by one or two oxygen atoms;

$R^8$ and $R^{10}$ independently represent H, $C_{1-6}$ alkyl, $Ar^2$, $Het^2$ or $C_{1-6}$ alkyl substituted by $Ar^2$ or $Het^2$;

Z represents $CO_2H$, $CONH(tetrazol-5-yl)$, $CONHSO_2O(C_{1-4}$ alkyl), $CO_2Ar^3$, $CO_2(C_{1-6}$ alkyl), tetrazol-5-yl, $CONHSO_2Ar^3$, $CONHSO_2(CH_2)_qAr^3$ or $CONHSO_2(C_{1-6}$ alkyl);

m represents 0, 1, 2 or 3;
n represents 0, 1 or 2;
p represents 2, 3 or 4;
q represents 1, 2 or 3;

$Ar^{1-3}$ independently represent phenyl, naphthyl, or an aromatic heterocycle having 5 or 6 ring members up to 4 of which are selected from N, S and O, which aromatic heterocycle is optionally fused to a benzene ring, and which phenyl group is optionally fused to an aromatic heterocycle as defined immediately above, the group as a whole being optionally substituted by one or more groups falling within the definition of $R^1$ above; and $Het^1$ and $Het^2$ independently represent a non-aromatic heterocycle having 5 or 6 ring members up to 4 of which are selected from N, S and O, which group is optionally substituted by one or more groups falling within the definition of $R^1$ above, and is further optionally substituted by =O or =S; provided that:

(i) when $R^1$ represents methoxy or is absent, $R^2$ is absent, $R^3$ represents H, $R^4$ represents H, methyl or ethyl, and $R^6$ represents unsubstituted phenyl, then Z does not represent $CO_2H$ or $CO_2(C_{1-6}$ alkyl);

(ii) when $R^1$ and $R^2$ are absent, $R^3$ represents $CO(p-ClC_6H_4)$, $R^4$ represents H, and $R^6$ represents unsubstituted phenyl, then Z does not represent $CO_2(C_{1-6}$ alkyl); and (iii) when $R^1$ represents methoxy, $R^2$ is absent, $R^3$ represents $CO(p-ClC_6H_4)$, $R^4$ represents methyl, and $R^6$ represents unsubstituted phenyl, then Z does not represent $CO_2H$;

or a pharmaceutically acceptable derivative thereof.

Pharmaceutically acceptable derivatives include those compounds in which the functional groups explicitly recited above have been derivatised to provide prodrugs which can be converted to the parent compound in vivo. Such prodrugs are discussed in Drugs of Today. Vol 19, 499–538 (1983) and Annual Reports in Medicinal Chemistry, Vol 10, Ch 31 p306–326. In addition, pharmaceutically acceptable derivatives include pharmaceutically acceptable salts, such as alkali metal salts (for example sodium salts) of any acidic groups that may be present.

"Halogen" includes fluorine, chlorine, bromine and iodine.

Alkyl groups which $R^{1-4}$, $R^{6-10}$ and Z represent or comprise may be straight chain, branched or cyclic.

Besides phenyl and naphthyl, specific groups that $Ar^{1-3}$ may represent or comprise include indolyl, pyridinyl, thienyl, oxazolyl, thiazolyl, isothiazolyl, pyrazolyl, triazolyl, tetrazolyl, oxadiazolyl, thiadiazolyl, imidazolyl, thiazolinidyl, isoxazolyl, oxadiazolyl, thiadiazolyl, pyrrolyl and pyrimidinyl.

Specific groups that Het$^1$ and Het$^2$ may represent or comprise include oxazolidinyl, triazolethione, triazolone, oxadiazolone, oxadiazolethione, imidazolidinyl, morpholinyl, piperidinyl and piperazinyl.

Preferred groups of compounds which may be mentioned include those in which:

(a) R$^1$ represents halogen, $(CH_2)_m CONR^7R^8$, $(CH_2)_m CO_2R^8$, $(CH_2)_m COR^8$, $(CH_2)_m OR^8$ or $(CH_2)_m CN$. In these groups it is preferred that R$^7$ and R$^8$ represent H or $C_{1-6}$ alkyl. Preferably, m is 0 or 1. Thus, specific groups which may be mentioned are $CONH_2$, $CO_2H$, $CH_2OH$, F or $CH_3CO$. R$^1$ is preferably attached to the 6-position of the indole ring.

(b) R$^2$ is absent (i.e. its place on the indole ring is occupied by H).

(c) R$^3$ represents H, $C_{1-6}$ alkyl or $(CH_2)_p OR^{10}$. Preferably, R$^{10}$ is $C_{1-6}$ alkyl and p is 2. Thus, specific groups which may be mentioned are methyl and $(CH_2)_2 OCH_3$.

(d) R$^4$ represents H.

(e) R$^5$ represents H.

(f) R$^6$ represents phenyl fused to a saturated 5-membered heterocyclic ring, for example 3,4-methylenedioxyphenyl.

(g) Z represents $CO_2H$ or $CONHSO_2Ar^3$. Preferably, Ar$^3$ is phenyl substituted by one or more groups selected from $C_{1-6}$ alkyl, $C_{1-6}$ alkoxy and $C_{1-6}$ alkyl substituted by carboxy. Thus, specific groups which may be mentioned are:

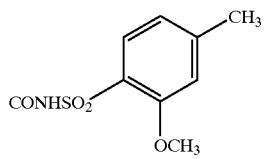

and

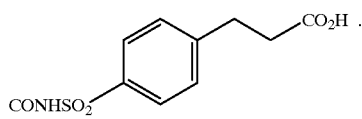

There is further provided a process for the production of the compounds of the invention, comprising:

(a) when R$^5$ represents H, reaction of a compound of formula IIA.

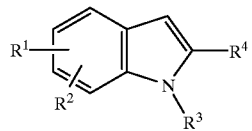

IIA wherein R$^{1-4}$ are as defined above, with a compound of formula III.

III wherein R$^6$ and Z are as defined above, in the presence of a Lewis acid or trifluoroacetic acid, and a tri($C_{1-6}$ alkyl)silane;

(b) when R$^5$ represents OH, reaction of a compound of formula IIA, as defined above, with a compound of formula III, as defined above, in the presence of a Lewis acid;

(c) when R$^3$ represents H and R$^5$ represents H, treatment of a compound of formula IIB,

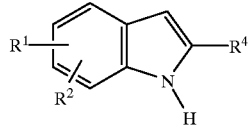

IIB wherein R$^1$, R$^2$ and R$^4$ are as defined above, with a Grignard reagent, followed by reaction with a compound of formula III, as defined above, followed by treatment with a Lewis acid or trifluoroacetic acid, and a tri($C_{1-6}$ alkyl)silane;

(d) when R$^3$ represents H and R$^5$ represents H, treatment of a compound of formula IIB, as defined above, with a Grignard reagent, followed by reaction with a compound of formula IV,

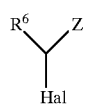

IV wherein R$^6$ and Z are as defined above, and Hal represents halogen;

(e) when R$^5$ represents H, reaction of a compound of formula IIA, as defined above, with a compound of formula IV, as defined above, in the presence of a hindered, non-nucleophilic base;

(f) reacting a compound of formula I, in which R$^1$ represents Br, with CO gas in the presence of a palladium catalyst and a reducing agent, to provide the corresponding compound of formula I in which R$^1$ represents CHO;

(g) reacting a compound of formula I, in which R$^1$ represents Br, with CO gas in the presence of a palladium catalyst and a $C_{1-6}$ alkanol, to provide the corresponding compound of formula I in which R$^1$ represents $CO_2(C_{1-6}$ alkyl);

(h) coupling a compound of formula I in which Z represents $CO_2H$ with a compound of formula VI.

$H_2NSO_2Ar^3$   VI wherein Ar$^3$ is as defined above, to provide the corresponding compound of formula I in which Z represents $CONHSO_2Ar^3$; or (i) reacting a compound of formula I, in which R$^1$ represents Br, with an alkyl lithium reagent and quenching with dimethylformamide or carbon dioxide, to give a corresponding compound in which R$^1$ represents CHO or $CO_2H$ respectively;

and where desired or necessary converting the resulting compound of formula I into a pharmaceutically acceptable derivative thereof or vice versa.

In process (a), suitable Lewis acids include boron trifluoride diethyletherate. The reaction is preferably carried out in a solvent which does not adversely affect the reaction, for example dichloromethane, at a temperature below room temperature, for example −40 to −78° C. A preferred tri($C_{1-6}$ alkyl)silane is triethylsilane. Intermediate compounds in which $R^5$ represents OH may be isolated from this process.

In process (b), suitable Lewis acids include boron trifluoride diethyletherate. The reaction is preferably carried out in a solvent which does not adversely affect the reaction, for example dichloromethane, at a temperature below room temperature, for example −40 to −78° C. The reaction is followed by basic work up.

In process (c), suitable Grignard reagents include methylmagnesium iodide. The reaction is preferably carried out in a solvent which does not adversely affect the reaction, for example toluene, below room temperature, for example −70° C. Suitable Lewis acids include boron trifluoride diethyletherate. The acid treatment may be carried out in a solvent which does not adversely affect the reaction, for example dichloromethane, at a temperature of 0° C. to room temperature. A preferred tri($C_{1-6}$ alkyl)silane is triethylsilane.

In process (d), suitable Grignard reagents include methylmagnesium iodide. The reaction is preferably carried out in a solvent which does not adversely affect the reaction, for example toluene, at or around room temperature. The reaction mixture may be worked up with a weak acid such as aqueous ammonium chloride. Hal is preferably Br.

In process (e), suitable hindered non-nucleophilic bases include 2,6-dimethylpyridine. The reaction is preferably carried out in a solvent which does not adversely affect the reaction, for example dimethylformamide, at an elevated temperature, for example 80° C.

In process (f), suitable palladium catalysts include dichlorobis(triphenylphosphine)palladium(II). Suitable reducing agents include sodium formate. The reaction is preferably carried out in a solvent which does not adversely affect the reaction, for example dimethylformamide, at an elevated temperature, for example 110° C.

In process (g), suitable palladium catalysts include dichlorobis(triphenylphosphine)palladium(II). The reaction is preferably carried out in a solvent which does not adversely affect the reaction, for example dimethylformamide, at an elevated temperature, for example the reflux temperature of the reaction mixture.

In process (h), the reaction may be facilitated by the use of conventional coupling agents, for example N,N-carbonyl diimidazole. When using this agent, the acid is first reacted with the agent (for example in dichloromethane at the reflux temperature of the solvent), and then the product of this reaction is reacted with the amine (preferably in the presence of a strong hindered amine base such as 1,8-diazabicyclo[5.4.0]undec-7-ene, in a solvent such as dichloromethane at the reflux temperature of the solvent). An alternative agent is 1-(3-dimethylaminopropyl)-3-ethylcarbodiimide which reacts at room temperature.

In process (i), suitable alkyl lithium reagents include n-butyl lithium. The reaction is carried out by adding the alkyl lithium reagent to the compound of formula I in a solvent such as tetrahydrofuran, at a temperature below room temperature (for example −40 to −78° C.), and stirring for about 2 hours. Dimethylformamide or solid carbon dioxide is then added and the reaction mixture allowed to warm to room temperature.

Compounds of formulae IIA, IIB, III, IV and VI are either known or may be prepared by conventional methods well known to those skilled in the art. For example, compounds of formulae IIA and IIB may be prepared by the Fischer, Reissert and Madelung syntheses. In addition, International Patent Application WO 94/14434 discloses a number of routes to 2-carboxy indole derivatives (see page 8 onwards) which may be decarboxylated readily (using copper and quinoline) to give compounds of formulae IIA or IIB in which $R^4$ is H, or reduced to give compounds of formulae IIA or IIB in which $R^4$ is alkyl. Other methods for the preparation of indoles are described by Moyer et al. J Org Chem. 1986, 51, 5106–5110; Wender et al. Tetrahedron. 1983, 39 N° 22, 3767–3776; Uhle. J. Am Chem Soc. 1949, 71, 761; Uhle et al. J Am Chem Soc. 1960, 82, 1200; Nagasaka et al, Heterocycles, 1977, 8, 371; Bowman et al. J Chem Soc. Perkin Trans 1, 1972, 1121; Bowman et al, J Chem Soc, Perkin Trans 1, 1972, 1926; and Clark et al, Heterocycles, 1984, 22, 195.

Compounds of formula III in which $R^6$ is an electron-rich group (for example 1,3-benzodioxole) and Z is $CO_2CH_2CH_3$ may be prepared by a Friedel-Crafts acylation between a compound of formula $R^6H$ and the compound of formula $ClCOCO_2CH_2CH_3$. The reaction is preferably carried out in the presence of a Lewis acid (for example $AlCl_3$), in a solvent which does not adversely affect the reaction, for example dichloromethane, below room temperature (for example 0° C.).

Compounds of formula III in which $R^6$ is not an electron-rich group (for example groups substituted by halogen or OH) and Z is $CO_2CH_3$ may be prepared by reaction of a compound of formula $R^6Li$ with a compound of formula $CH_3OCOCO_2CH_3$. The reaction may be carried out in a solvent which does not adversely affect the reaction, for example tetrahydrofuran, below room temperature (for example −40° C. to −78° C.).

Compounds of formula $R^6Li$ may be prepared by reacting a compound of formula $R^6Br$ and butyl lithium. The reaction may be carried out in a solvent which does not adversely affect the reaction, for example tetrahydrofuran, below room temperature (for example −78° C.).

Compounds of formula IV may be prepared by halogenating the corresponding alcohol with an agent such as hydrobromic acid. When Z represents $CO_2(C_{1-6}$ alkyl), compounds of formula $R^6CH(OH)Z$ may be prepared by reacting an aldehyde of formula $R^6CHO$ with bromoform under basic conditions, and treating the crude carboxylic acid intermediate with a $C_{1-6}$ alkanol.

Compounds of formula I may be converted into other compounds of formula I using known techniques. Processes (f)–(i) above are such conversions of particular interest.

Compounds of formulae I, III or IV in which Z represents a carboxylic ester may be converted into corresponding compounds in which Z represents other groups by conventional methods.

Compounds of formulae I, IIA or IIB in which $R^3$ represents H may be converted to corresponding compounds in which $R^3$ is other than H by conventional methods. In general, $R^3$ groups other than H may be added by treatment of a compound of formula I, IIA or IIB in which $R^3$ represents H with sodium hydride, followed by an appropriate compound of formula $R^3Br$ or $R^3I$, in dimethylformamide at 0° C. Preferably, compounds of formulae I, IIA or IIB in which $R^3$ represents electron-withdrawing groups (such as $SO_2R^{10}$, $SO_2NR^9R^{10}$, $CONR^9R^{10}$ and $COR^{10}$) are prepared by reacting a compound of formula I, IIA or IIB in which $R^3$ represents H with an appropriate compound of formula $R^3Cl$.

The compounds of the invention may be separated and purified by conventional methods.

It will be apparent to those skilled in the art that sensitive functional groups may need to be protected and deprotected during synthesis of a compound of the invention. This may be achieved by conventional techniques, for example as described in 'Protective Groups in Organic Synthesis' by T W Greene and P G M Wuts, John Wiley and Sons Inc, 1991. For example, it may be desirable to protect the indole nitrogen of a compound of formula IIA and use the method of process (a) followed by deprotection to give a compound of formula I in which $R^3$ represents H. Processes (a)–(h) embrace such protection and deprotection steps.

The synthesis of triazolethione, oxadiazolone and oxadiazolethione is described in J Med Chem, 1993, 36, 1090–1099. The synthesis of oxathiadiazole is described in Bioorganic and Medicinal Chemistry Letters, 1994, 4 N° 1, 41–44.

The compounds of the invention may possess one or more chiral centres and so exist in a number of stereoisomeric forms. All stereoisomers and mixtures thereof are included in the scope of the present invention. Racemic compounds may either be separated using preparative HPLC and a column with a chiral stationary phase or resolved to yield individual enantiomers utilising methods known to those skilled in the art. In addition, chiral intermediate compounds may be resolved and used to prepare chiral compounds of formula I.

The compounds of the invention are useful because they have pharmacological activity in animals, including humans. More particularly, they are useful in the treatment of restenosis, renal failure, pulmonary hypertension, benign prostatic hypertrophy, congestive heart failure, stroke, angina, atherosclerosis, cerebral and cardiac ischaemia and cyclosporin induced nephrotoxicity. The treatment of restenosis, renal failure and pulmonary hypertension are of particular interest. The compounds of the invention may be administered alone or as part of a combination therapy.

Thus, according to a further aspect of the invention, there is provided a compound of formula I, as defined above, but without provisos (i) and (ii), or a pharmaceutically acceptable derivative thereof, for use as a pharmaceutical.

There is further provided a pharmaceutical formulation comprising a compound of formula I, as defined above, but without provisos (i) and (ii). or a pharmaceutically acceptable derivative thereof, and a pharmaceutically acceptable adjuvant, diluent or carrier.

The invention also provides the use of a compound of formula I, as defined above, but without provisos (i)–(iii), or a pharmaceutically acceptable derivative thereof, in the manufacture of a medicament for the treatment of restenosis, renal failure, pulmonary hypertension, benign prostatic hypertrophy, congestive heart failure, stroke, angina, atherosclerosis, cerebral and cardiac ischaemia or cyclosporin induced nephrotoxicity. The invention also provides a method of treatment of these diseases, which comprises administering a therapeutically effective amount of a compound of formula I, as defined above, but without provisos (i)–(iii), or a pharmaceutically acceptable derivative thereof, to a patient in need of such treatment.

Without being limited by theory, the compounds of the invention are believed to be endothelin receptor antagonists. Endothelin (ET) is a potent vasoconstrictor synthesised and released by endothelial cells. There are three distinct isoforms of ET: ET-1, ET-2 and ET-3, all being 21-amino acid peptides and herein the 'term endothelin' refers to any or all of the isoforms. Two receptor subtypes, $ET_A$ and $ET_B$ have been pharmacologically defined (see for example H. Arai et al. Nature, 348, 730, 1990) and further subtypes have recently been reported. Stimulation of $ET_A$ promotes vasoconstriction and stimulation of $ET_B$ receptors causes either vasodilation or vasoconstriction.

The effects of endothelin are often long-lasting and, as the endothelins are widely distributed in mammalian tissues, a wide range of biological responses have been observed in both vascular and non-vascular tissue. The main effects of endothelin are observed in the cardiovascular system, particularly in the coronary, renal, cerebral and mesenteric circulation.

Increased circulating levels of endothelin have been observed in patients who have undergone percutaneous transluminal coronary angioplasty (PTCA) (A. Tahara et al. Metab. Clin. Exp. 40, 1235, 1991) and ET-1 has been found to induce neointimal formation in rats after balloon angioplasty (S. Douglas et al. J. Cardiovasc. Pharm., 22 (Suppl 8), 371, 1993). The same workers have found that an endothelin antagonist, SB-209670, causes a 50% reduction in neointimal formation relative to control animals (S. Douglas et al. Circ Res, 75, 1994). Antagonists of the endothelin receptor may thus be useful in preventing restenosis post PTCA.

Endothelin-1 is produced in the human prostate gland and endothelin receptors have been identified in this tissue. Since endothelin is a contractile and proliferative agent endothelin antagonists could be useful in the treatment of benign prostate hypertrophy.

There is widespread localisation of endothelin and its receptors in the central nervous system and cerebrovascular system (R. K. Nikolov et al. Drugs of Today, 28(5), 303, 1992) with ET being implicated in cerebral vasospasm, cerebral infarcts and neuronal death. Elevated levels of endothelin have also been observed in patients with:

Chronic renal failure (F. Stockenhuber et al. Clin Sci (Lond.), 82, 255, 1992)

Ischaemic Heart Disease (M. Yasuda Am. Heart J., 119, 801, 1990)

Stable or unstable angina (J. T. Stewart. Br. Heart J. 66, 7 1991)

Pulmonary Hypertension (D. J. Stewart et al. Ann. Internal Medicine, 114, 464, 1991)

Congestive heart failure (R. J. Rodeheffer et al. Am. J. Hypertension, 4, 9A, 1991)

Preeclampsia (B. A. Clark et al. Am. J. Obstet. Gynecol., 166, 962, 1992)

Diabetes (A. Collier et al. Diabetes Care. 15 (8), 1038, 1992)

Crohn's disease (S. H. Murch et al. Lancet. 339, 381, 1992)

Atherosclerosis (A. Lerman et al. New Eng. J. Med., 325, 997, 1991)

In every case the disease state associated with the physiologically elevated levels of endothelin is potentially treatable with an endothelin receptor antagonist and hence a compound of the invention.

Compounds that selectively antagonise the $ET_A$ receptor rather than the $ET_B$ receptor are preferred.

The biological activity of the compounds of the invention may be demonstrated in Tests A–C below:

A. Binding assay

Competition between test compounds and $^{125}$I-ET-1 binding to human endothelin receptors is determined as follows. Binding to $ET_A$ receptors 25 µl of a 30 pM solution of [$^{125}$I]Tyr$^{13}$ ET-1 (specific activity 2,200 Ci/mM) is mixed with 25 µl samples of test compound (final concentrations in the range 0.1 nM–50,000 nM). 200 µl of a solution containing cloned human $ET_A$ receptor (0.75 pmoles receptor protein/ml). 50 mM Tris. 0.5 mM $CaCl_2$, 0.1% human serum albumen, 0.1% bacitracin, 0.05% Tween 20. pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radioactivity, and the $IC_{50}$ (the concentration of test compound at which 50% of the radio-labelled compound is unbound) determined for the concentration range tested.

Binding to $ET_B$ receptors

25 $\mu$l of a 30 pM solution of $[^{125}I]Tyr^{13}$ ET-1 (specific activity 2,200 Ci/mM) is mixed with 25 $\mu$l samples of test compound (final concentration 0.1 nM–50,000 mM). 200 $\mu$l of a solution containing cloned human $ET_B$ receptor (0.25 pmoles receptor protein/ml), 50 mM Tris, 0.5 mM $CaCl_2$, 0.1% human serum albumen, 0.1% bacitracin, 0.05% Tween 20, pH 7.4 is added. The solution is mixed at 37° C. for 2 hours. After the incubation, the unbound ligand is separated from receptor bound ligand by filtration with a Brandel cell harvester, followed by three washes of buffer. Filter papers are counted for radio-activity, and the $IC_{50}$ (the concentration of test compound at which 50% of the radio-labelled compound is unbound) determined for the concentration range tested.

B. In vitro vascular smooth muscle activity

Rat aorta

Rat aortae are cleaned of connective tissue and fat and cut into helical strips approx 4 mm in width. The endothelium is removed by dragging the luminal surface of the tissue gently across filter paper moistened with Krebs solution of composition (mM) NaCl 130, KCl 5.6, $NaHCO_3$ 25, Glucose 11.1, $NaH_2PO_4$ 0.6, $CaCl_2$ 2.16, $MgCl_2$ 0.5, gassed with 95% $O_2$/5% $CO_2$. The strips are mounted in isolated organ baths in Krebs solution under a resting tension of 1 gram. Organ bath solutions are maintained at 37° C. and continuously aerated with 95% $O_2$/5% $CO_2$. Tensions are measured with Maywood Industries isometric force transducers and displayed on Gould TA4000 recorders. After equilibration in the organ bath for 1 hour, tissues are contracted by the addition of KCl to a final concentration of 60 mM. The KCl is removed by replacing the Krebs solution, with two further washes with Krebs solution. To determine the potency of an $ET_A$ receptor antagonist, two tissues are cumulatively dosed with ET-1 (0.1 nM–1 $\mu$M); other tissues are dosed with ET-1 (0.1 nM–1 $\mu$M) in duplicate, beginning 30 minutes after the inclusion in the organ bath medium of the test compound. Sufficient tissues are used per experiment to generate dose-response curves to ET-1 in the absence and the presence of at least 3 concentrations of antagonist. Data are expressed as the mean ±s.e.m. Dissociation constants ($k_b$) of competitive antagonists are calculated by the method of Arunlakshana and Schild.

Rabbit pulmonary artery

Isolated rabbit pulmonary arteries are cleaned of connective tissue and fat and cut into rings approx 4 mm in width. The endothelium is removed by inserting a fibrous instrument moistened with Krebs solution of composition (mM) NaCl 130, KCl 5.6, $NaHCO_3$ 25, Glucose 11.1, $NaH_2PO_4$ 0.6, $CaCl_2$ 2.16, $MgCl_2$ 0.5, gassed with 95% $O_2$/5% $CO_2$. The rings are mounted in isolated organ baths in Krebs solution under a resting tension of 1 gram. Organ bath solutions are maintained at 37° C. and continuously aerated with 95% $O_2$/5% $CO_2$. Tensions are measured with Maywood Industries isometric force transducers and displayed on Gould TA4000 recorders. After equilibration in the organ bath for 1 hour, tissues are contracted by the addition of KCl to a final concentration of 60 mM. The KCl is removed by replacing the Krebs solution, with two further washes with Krebs solution. To determine the potency to an $ET_B$ receptor antagonist, two tissues are cumulatively treated with BQ-3020 (0.1 nM–1 $\mu$M); other tissues are treated with BQ-3020 (0.1 nM–1 $\mu$M) in duplicate, beginning 30 minutes after the inclusion in the organ bath medium of the test compound. Sufficient tissues are used per experiment to generate dose-response curves to BQ-3020 in the absence and the presence of at least 3 concentrations of antagonist. Data are expressed as the mean ±s.e.m. Dissociation constants ($k_b$) of competitive antagonists are calculated by the method of Arunlakshana and Schild.

C. In vivo blockade of endothelin-induced blood pressure elevation

In anaesthetised, ganglion-blocked and artificially respired rats, the left common carotid artery and the right jugular vein are cannulated for the measurement of arterial blood pressure and the administration of compound respectively. Rats are treated with the $ET_B$ antagonist BQ-788 (0.25 mg/kg i.v.). Beginning 10 minutes after administering BQ-788, the hypertensive response to ET-1 (1 $\mu$g/kg i.v.) is determined. When the blood pressure has returned to baseline, the test compound is administered (0.1–20 mg/kg i.v.) and after 10 minutes the ET-1 challenge is repeated. Increasing concentrations of the test compound are administered, followed 10 minutes after each administration by a further ET-1 challenge. An $IC_{50}$ is determined based upon inhibition of ET-1 induced pressor response upon cumulative dosing with compound.

Duration of blockade is determined in anaesthetised, ganglion-blocked and artificially respired rats, in which the left common carotid artery and the right jugular vein are cannulated for the measurement of arterial blood pressure and the administration of compound respectively. Rats are treated with the $ET_B$ antagonist BQ-788 (0.25 mg/kg i.v.). Beginning 10 minutes after administering BQ-788, the hypertensive response to ET-1 (1 $\mu$g/kg i.v.) is determined. When the blood pressure has returned to baseline, the test compound is administered (10 mg/kg i.v.). Further administrations of ET-1 are made 5, 20 and 60 minutes after dosing the test compound. In separate animals, prepared similarly, an ET-1 challenge is made 2 or 4 hours after dosing with the test compound, in these animals BQ-788 is dosed 10 minutes before the ET-1 challenge. For later time points, rats are dosed with the test compound (10 mg/kg) i.v. via a tail vein or p.o., they are then anaesthetised and prepared for blood pressure measurement as above. In these rats, ET-1 (1 $\mu$g/kg i.v.) was administered 6 or 8 hours after the test compound.

For human use the compounds of the invention can be administered alone but will generally be administered in admixture with a pharmaceutical carrier selected with regard to the intended route of administration and standard pharmaceutical practice. For example they can be administered orally in the form of tablets containing such excipients as starch or lactose or in capsules or ovules either alone or in admixture with excipients or in the form of elixirs, solutions or suspensions containing the compound or salt in a liquid carrier, for example a vegetable oil, glycerine or water with a flavouring or colouring agent. They can be injected parenterally, for example intravenously, intramuscularly or subcutaneously. For parental administration, they are best used as sterile aqueous solutions which may contain other substances, for example, enough glucose or salts to make the solution isotonic with blood. For parenteral administration the compound or salt may also be administered as a solution or suspension in a suitable oil, for example polyethylene glycol, lecithin or sesame oil.

Compounds of the invention may also be administered through inhalation of a solution, suspension or emulsion that may be administered as a dry powder or in the form of an aerosol using a conventional propellant such as dichlorodifluoromethane.

For oral or parenteral administration to human patients the daily dosage levels of compounds of the invention will be from 0.01 to 30 mg/kg (in single or divided doses) and preferably will be in the range 0.01 to 5 mg/kg. Thus tablets will contain 1 mg to 0.4 g of compound for administration singly or two or more at a time, as appropriate. The above dosages are, of course only exemplary of the average case and there may be instances where higher or lower doses are merited, and such are within the scope of the invention.

Alternatively the compounds of the invention can be administered in the form of a suppository or pessary, or they may be applied topically in the form of a lotion, solution, cream, ointment or dusting powder or in the form of a medicated plaster, patch or membrane. For example they may be incorporated in a cream containing an aqueous emulsion of polyethylene glycols or liquid paraffin. The compounds may also be administered intranasally.

The invention is illustrated by the following Examples, in which the following abbreviations are used:

APCI atmospheric pressure chemical ionisation
DMF dimethylformamide
DMSO dimethylsulphoxide
Et ethyl
h hour
iPr isopropyl
LRMS low resolution mass spectroscopy
min minute
Me methyl
NMR nuclear magnetic resonance
TFA trifluoroacetic acid
Tlc thin layer chromatography

EXAMPLE 1

Ethyl 2-[3-(1-ethyl-6-methoxycarbonyl)indolyl]-2-(3,4-methylenedioxyphenyl)acetate (a) 6-Bromo-1-ethylindole

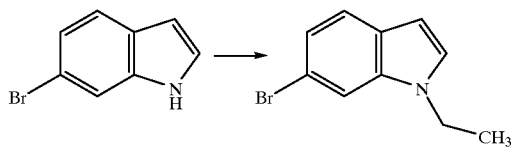

Sodium hydride (480 mg of a 60% dispersion in mineral oil) was added to a stirred solution of 6-bromoindole (1.8 g, 9.2 mmol) in dimethylformamide (20 ml) at 0° C. under a nitrogen atmosphere. After 1 hour bromoethane (1.1 ml, 14.7 mmol) was added and the cooling bath removed. After 12 hours the dimethylformamide was removed in vacuo. The residue as purified directly by flash column chromatography (using 95% hexane, ethyl acetate as eluant) to give 2.1 g of the subtitle compound as a yellow oil.

$^1$H NMR (300 MHz, CDCl$_3$): δ=1.45 (t, 3 H), 4.10 (q, 2 H), 6.45 (d, 1 H), 7.10 (d, 1 H), 7.20 (d, 1 H), 7.45 (d, 1 H), 7.55 (s, 1 H)

LRMS (Thermospray): 224 (MH$^{31}$)

(b) 6-Methoxycarbonyl-1-ethylindole

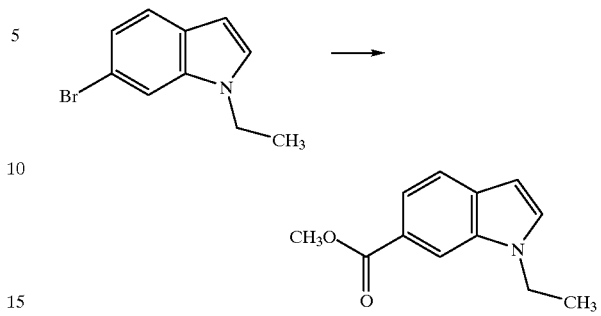

Sec-butyllithium (9.4 ml of a 1.3M solution in cyclohexene) was added to a stirred solution of 6-bromo-1-ethylindole [the compound of step (a), 2.5 g] in diethylether (20 ml) at −78° C. under a nitrogen atmosphere. After 30 minutes this solution was transferred by cannula to a stirred solution of methyl chloroformate (1.29 ml, 16.74 mmol) in diethyl ether (8 ml) at −78° C. under a nitrogen atmosphere. After 1 hour the cooling bath was removed and the mixture was allowed to warm to room temperature. After a further 1 hour the mixture was poured into brine and extracted with ethyl acetate. The organic layers were dried (MgSO$_4$) and concentrated in vacuo to give a yellow oil. Flash column chromatography (elution with 90% hexane, 10% ethyl acetate) gave 1.76 g of the subtitle compound as a pale yellow oil.

$^1$H NMR (300 MHz, CDCl$_3$): δ=1.50 (t, 3 H), 4.00 (s, 3 H), 4.25 (q, 2 H), 6.50 (d, 1 H), 7.25 (d, 1 H), 7.60 (d, 1 H), 7.80 (d, 1 H), 8.10 (s, 1 H)

LRMS (Thermospray): 204.2 (MH$^+$)

(c) Benzo(1,3)dioxol-5-yl-oxo-acetic acid ethyl ester

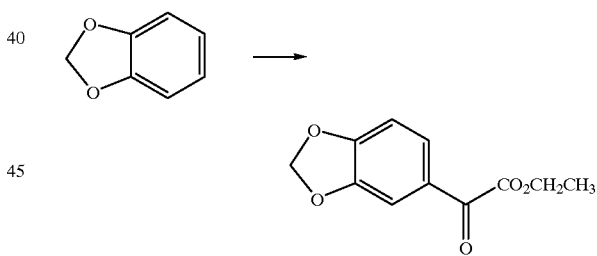

A mixture of ethyl oxalyl chloride (50 ml, 0.45 mmol) and 1,3-benzodioxole (50 g, 0.41 mmol) in dichloromethane (40 ml) was added dropwise to a stirred slurry of aluminium trichloride (71 g, 0.53 mmol) in dichloromethane (500 ml) at 0° C. under a nitrogen atmosphere. After 2 hours the mixture was poured into iced water and the organic layer was washed with further volumes of water (3×500 ml), saturated sodium bicarbonate solution (500 ml) and brine (500 ml). The organic layer was dried (magnesium sulphate) and concentrated to give an orange oil. Flash column chromatography (90% hexane, 10% ethyl acetate) gave 30 g of the subtitle compound as a pale yellow oil.

$^1$H NMR (300 MHz, CDCl$_3$): δ=1.40 (t, 3 H), 4.40 (q, 2 H), 6.10 (s, 2 H), 6.85 (d, 1 H), 7.50 (s, 1 H), 7.60 (d, 1 H).

LRMS (Thermospray): 240 (MNH$_4^-$)

(d) Ethyl 2-[3-(1-ethyl-6-methoxycarbonyl)indolyl]-2-(3,4-methylenedioxyphenyl)acetate

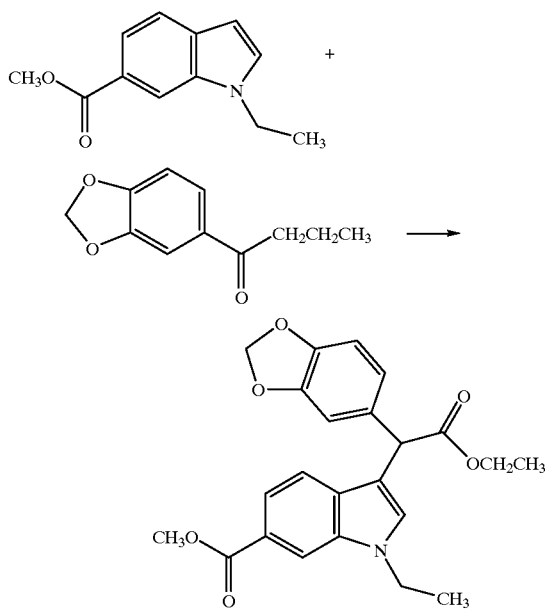

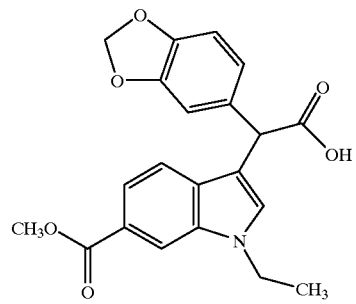

A mixture of 6-methoxycarbonyl-1-ethylindole [the compound of step (b), 2.1 g, 10.3 mmol] and benzo(1,3)dioxol-5-yl-oxo-acetic acid ethyl ester [the subtitle compound of step (c), 2.4 g, 10.9 mmol] in dichloromethane (10 ml) was added dropwise to a solution of triethylsilane (6.4 ml 51.5 mmol) and boron trifluoride diethyletherate (3.28 ml, 20.6 mmol) in dichloromethane (15 ml) at −78° C. under a nitrogen atmosphere. After 1 hour the deeply coloured mixture was warmed to −40° C. After 10 hours the mixture was warmed to room temperature and poured into sodium hydroxide solution (200 ml of 1 M). The flask was washed with dichloromethane (150 ml) and the 2 phases were vigorously shaken. The organic layer was separated and washed with brine before drying (MgSO$_4$) and concentrating in vacuo. Flash column chromatography (elution with 90% hexane, 10% ethyl acetate) gave 4.2 g of the title compound as a clear oil.

$^1$H NMR (300 MHz, CDCl$_3$): δ=1.45 (t, 3 H), 4.00 (s, 3 H), 4.25 (q, 2 H), 5.15 (s, 1 H), 5.90 (s, 2 H), 6.70 (d, 1 H), 6.80 (d, 1 H), 6.85 (s, 1 H), 7.30 (s, 1 H), 7.40 (d, 1 H) 7.70 (d, 1 H), 8.10 (s, 1 H)

LRMS (Thermospray): 410.2 (MH$^-$)

EXAMPLE 2
2-[3-(1-Ethyl-6-methoxycarbonyl)indolyl]-2-(3,4-methylenedioxyphenyl)acetic acid

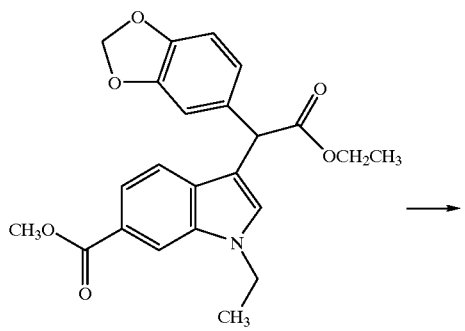

Sodium hydroxide solution (5 ml of 2M) was added to a stirred solution of ethyl 2-[3-(1-ethyl-6-methoxycarbonyl) indolyl]-2-(3,4-methylenedioxyphenyl)acetate [the title compound of Example 1, 3.76 g, 9.2 mmol] in a 2:1 mixture of tetrahydrofuran and methanol (30 ml) at room temperature. The mixture was heated at reflux for 6 hours, following closely by tlc, before recooling and removing the organic solvents in vacuo. The residue was poured into sodium hydroxide solution (200 ml of 0.5 M) and extracted with dichloromethane to recover an unreacted starting material. The aqueous layer was then acidified to pH1 with 2 M hydrochloric acid and extracted with dichloromethane (2×300 ml). The organic fractions were combined, dried and concentrated in vacuo to give the crude product as an oil. Flash column chromatography (elution with 94% dichloromethane, 5% methanol, 1% ammonia) gave the title compound as a clear oil.

$^1$H NMR (300 MHz, CDCl$_3$): δ=1.45 (t, 3 H), 3.95 (s, 3 H), 4.20 (q, 2 H), 5.20 (s, 1 H), 5.95 (s, 2 H), 6.80 (d, 1 H), 6.85 (d, 1 H), 6.90 (s, 1 H), 7.35 (s, 1 H), 7.40 (d, 1 H), 7.85 (d, 1 H), 8.10 (s, 1 H)

LRMS (Thermospray): 382.6 (MH$^-$)

EXAMPLE 3
N-(4-Iso-propylbenzenesulphonyl)-2-[3-(1-ethyl-6-methoxycarbonyl)indolyl]-2-(3,4-methylenedioxyphenyl) acetamide

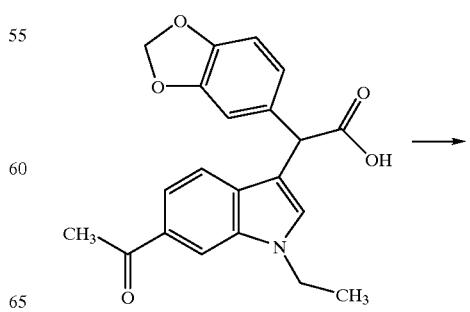

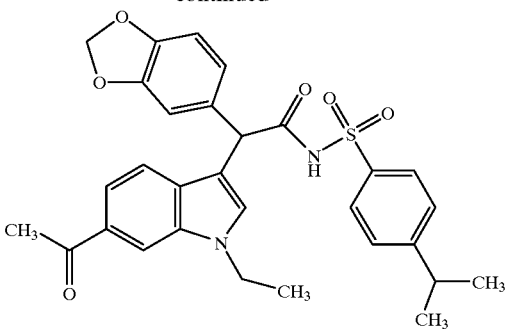

N,N-Carbonyl diimidazole (0.99 g, 6.14 mmol) was added to a stirred solution of 2-[3-(1-ethyl-6-methoxycarbonyl)indolyl]-2-(3,4-methylenedioxyphenyl) acetic acid [the title compound of Example 2, 1.8 g, 4.7 mmol] in dichloromethane (60 ml) at room temperature under a nitrogen atmosphere. The solution was heated to reflux for 12 hours. The mixture was cooled and 1,8-diazabicyclo[5.4.0]undec-7-ene (0.92 ml, 6.14 mmol) and 4-isopropylbenzenesulphonamide (1.03 g, 5.17 mmol) were added. The mixture was refluxed for a further 12 hours. After cooling the mixture was poured into ammonium chloride solution (200 ml) and extracted into dichloromethane. The organic fractions were dried (MgSO$_4$) and concentrated to give a yellow oil. Flash column chromatography using firstly dichloromethane and then 3% methanol in dichloromethane gave 1.95 g of the title compound as a pale yellow oil.

$^1$H NMR (300 MHz CDCl$_3$): δ=1.30 (d, 6 H), 1.45 (t, 3 H), 3.00 (m, 1 H), 3.95 (s, 3 H), 4.20 (q, 2 H), 5.00 (s, 1 H), 5.90 (s, 2 H), 6.60 (s, 1 H), 6.70 (d, 2 H), 7.05 (s, 1 H), 7.10 (d, 1 H), 7.35 (d, 2 H), 7.65 (d, 1 H), 7.80 (d, 2 H), 8.10 (s, 1 H), 8.20 (brs, 1 H)

LRMS (Thermospray): 580.4 (MNH$_4^+$)

EXAMPLE 4

N-(4-Iso-propylbenzenesulphonyl)-2-[3-(1-ethyl-6-carboxy)indolyl]-2-(3,4-methylenedioxyphenyl)acetamide

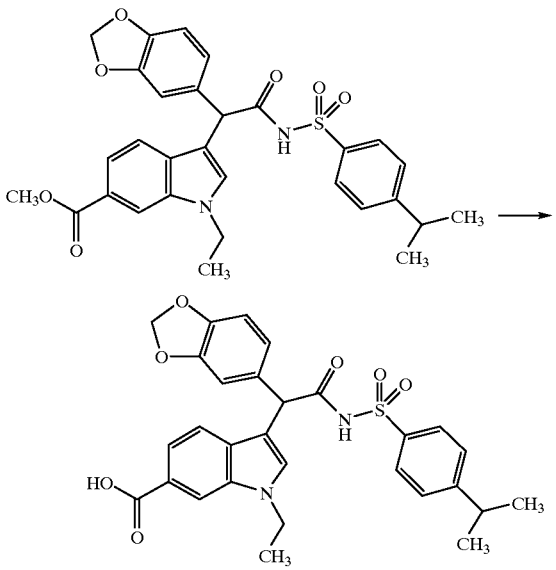

Aqueous KOH (14.2 ml of a 1 M solution) was added to a stirred solution of N-(4-isopropylbenzenesulphonyl)-2-[3-(1-ethyl-6-methoxycarbonyl)indolyl]-2-(3,4-methylenedioxyphenyl)acetamide [the title compound of Example 3, 2 g, 3.56 mmol] in methanol (50 ml) and the solution was heated at reflux for 8 hours. After cooling the methanol was removed in vacuo and the resulting solution was partitioned between 1M hydrochloric acid (100 ml) and dichloromethane (3×100 ml). The organic fractions were dried (MgSO$_4$) and concentrated to give a yellow solid. Flash column chromatography (using 95% dichloromethane/5% methanol as eluant) gave the title compound as a white solid.

$^1$H NMR (300 MHz, CDCl$_3$): δ=1.25 (d, 6 H), 1.40 (t, 3 H), 3.00 (m, 1 H), 4.15 (q, 2 H), 5.00 (s, 1 H), 5.90 (s, 2 H), 6.65 (d, 2 H), 6.70 (s, 1 H), 7.00 (s, 1 H), 7.15 (m, 1 H), 7.30 (d, 2H), 7.60 (m, 1 H), 7.85 (d, 2 H), 8.10 (s, 1 H)

LRMS (Thermospray): 566.3 (MNH$_4^+$)

Analysis: Found C, 63.29; H, 5.21; N, 4.95, C$_{29}$H$_{28}$N$_2$O$_7$S requires: C, 63.49; H, 5.14; N, 5.11.

EXAMPLE 5

N-(4-Iso-propylbenzenesulphonyl)-2-[3-(1-ethyl-6-methylamido)indolyl]-2-(3,4-methylenedioxyphenyl) acetamide

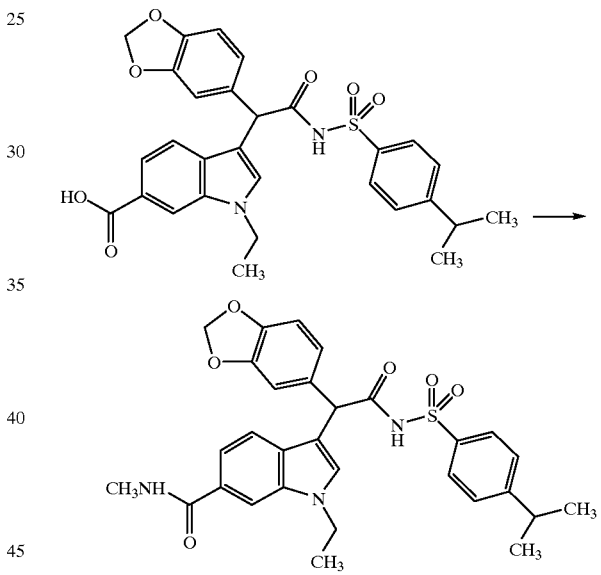

1-(3-Dimethylaminopropyl)-3-ethylcarbodiimide hydrochloride (56 mg, 0.294 mmol) was added to a stirred solution of N-(4-iso-propylbenzenesulphonyl)-2-[3-(1-ethyl-6-carboxy)indolyl]-2-(3,4-methylenedioxyphenyl)acetamide (the title compound of Example 4, 124 mg, 0.23 mmol), hydroxybenzotriazole (37 mg, 0.27 mmol), triethylamine (63 µl, 0.45 mmol) and methylamine hydrochloride (23 mg, 0.34 mmol) in dichloromethane (7 ml) at room temperature under a nitrogen atmosphere. After 12 hours the reaction mixture was poured into aqueous sodium hydrogen carbonate solution and extracted with dichloromethane (3×100 ml). The combined organic fractions were dried (MgSO$_4$) and concentrated to give a yellow solid. Flash column chromatography (using ethyl acetate as eluant) gave the title compound as a yellow solid.

$^1$H NMR (300 MHz, CDCl$_3$): δ=1.25 (d, 6 H), 1.40 (t, 3 H), 3.00 (m, 1 H), 3.05 (d, 3 H), 4.05 (q, 2 H) 5.00 (s, 1 H), 5.90 (s, 2 H), 6.30 (d, 1 H), 6.65 (d, 1 H), 6.70 (s, 1 H), 6.90 (d, 1 H), 6.95 (s, 1 H), 7.10 (d, 1 H), 7.25 (s, 1 H), 7.30 (d, 2 H), 7.85 (d, 2 H), 7.90 (s, 1 H), 9.40 (brs, 1 H).

LRMS (Thermospray): 562 (MH⁺).

Examples 6–10 were prepared by the method of Example 5, using the product of Example 4 and the appropriate substituted amine starting materials. Their physical data are shown in Table 1.

TABLE 1

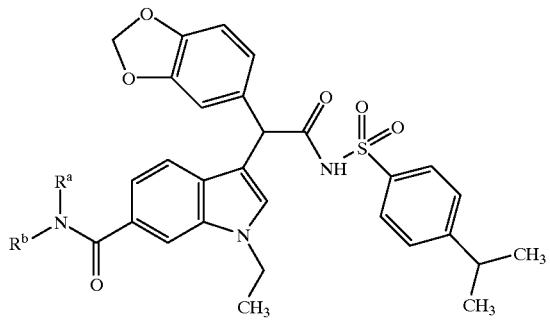

| Example N° | | Physical Data |
|---|---|---|
| 6 | 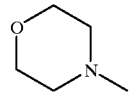 | ¹H NMR(300MHz, CDCl₃): δ=1.25(d, 6H), 1.35 (t, 3H), 2.30 (s, 3H), 2.40(m, 4H), 2.95(m, 1H), 3.50(m, 2H), 4.00(m, 2H), 4.20(q, 2H), 5.00(s, 1H), 5.95(s, 2H), 6.65(d 2H), 6.70(s, 1H), 6.85(d, 1H), 7.00(m, 1H), 7.20(m, 3H), 7.40(s, 1H), 7.80(d, 2H). LRMS(Thermospray): 631.5(MH⁺) |
| 7 | 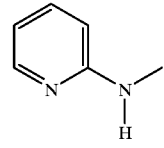 | ¹H NMR(300MHz, CDCl₃): δ=1.25(d, 6H), 1.40(t, 3H), 3.00 (m, 1H), 3.70(m, 8H), 4.10(q, 2H), 4.90(s, 1H), 5.90(s, 2H), 6.60(s, 1H), 6.70(m, 2H), 6.95(m, 3H), 7.30(d, 2H), 7.40(s, 1H), 7.80 (d, 2H), 8.85(brs, 1H) LRMS(Thermospray): 618(MH⁺) |
| 8 | 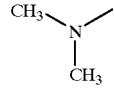 | ¹H NMR(300MHz, CD₃OD): δ=1.25(d, 6H), 1.40(t, 3H), 3.00 (m, 1H), 4.20(q, 2H), 5.10(s, 1H), 5.80(s, 2H), 6.70(d, 2H), 6.75(s, 1H), 7.00(s, 1H), 7.15(m, 1H), 7.30(d, 1H), 7.40(d, 2H), 7.50(d, 1H), 7.75(m, 1H), 7.80(d, 1H), 8.05(s, 1H), 8.20(d, 1H), 8.35(m, 1H) LRMS(Thermospray): m/z=625.3 (MH⁺) |
| 9 | 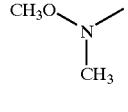 | ¹H NMR(300MHz, CD₃OD): δ=1.25(d, 6H), 1.40(t, 3H), 3.00 (m, 1H), 3.30(s, 6H), 4.20(q, 2H), 5.10(s, 1H), 5.95(s, 2H), 6.60(s, 1H), 6.65(s, 2H), 6.90(s, 1H), 6.95(d, 1H), 7.20(d, 1H), 7.40(d, 2H), 7.45(s, 1H), 7.80(d, 2H) LRMS(Thermospray): 576.6(MH⁺) |
| 10 | | ¹H NMR(300MHz, CDCl₃): δ=1.25(d, 6H), 1.40(t, 3H), 3.00 (m, 1H), 3.40(s, 3H), 3.60(s, 3H), 4.10(q, 2H), 5.00(s, 1H), 5.90(s, 2H), 6.65(d, 2H), 6.70(s, 1H), 7.00(s, 1H), 7.25(m, 2H), 7.30(d, 2H), 7.75(s, 1H), 7.80(d, 2H) LRMS(Thermospray): 609.5 (MNH₄⁺) |

EXAMPLE 11

N-(4-Iso-propylbenzenesulphonyl)-2-[3-[1-ethyl-6-(1,3,4-oxadiazol-2(3H)-one)]indolyl]-2-(3,4-methylenedioxyphenyl)acetamide

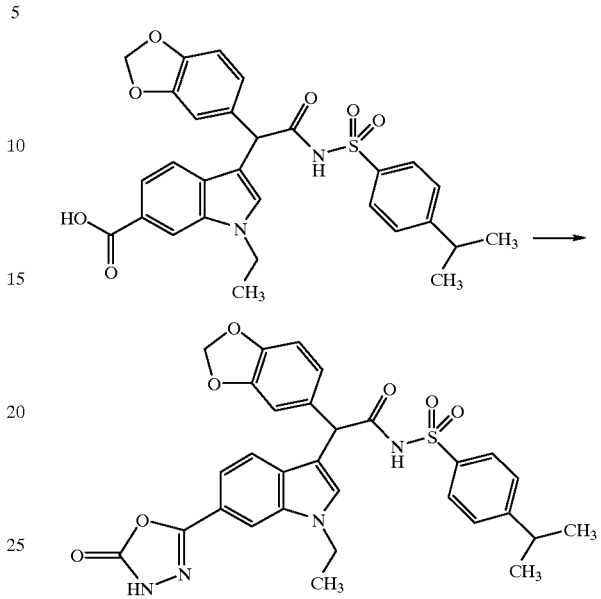

Oxalyl chloride (0.065 ml, 0.74 mmol) was added to a stirred solution of N-(4-isopropylbenzenesulphonyl)-2-[3-(1-ethyl-6-carboxy)indolyl]-2-(3,4-methylenedioxyphenyl) acetamide (the compound of Example 4, 340 mg, 0.62 mmol) in dry tetrahydrofuran (10 ml) at room temperature under a nitrogen atmosphere. Dimethylformamide (3 drops) was added and stirring was continued at room temperature for 2 hours. The solvent was removed in vacuo (azeotroping twice with toluene) and the residue redissolved in tetrahydrofuran (5 ml). This solution was added to a stirred solution of tert-butylcarbazate (163 mg, 1.24 mmol) in tetrahydrofuran (5 ml) at room temperature under a nitrogen atmosphere. After 18 hours the solvent was removed in vacuo and the residue dissolved in dichloromethane (3 ml). The solution was passed through a short plug of silica washing with 20 ml of a 95/5 mixture of dichloromethane/methanol. The solvent was again removed in vacuo and the residue redissolved in tetrahydrofuran (8 ml). Concentrated hydrochloric acid (1.9 ml) and water (0.6 ml) were added and the mixture was heated on a steam bath for 1 hour. After cooling the mixture was poured into water (100 ml), the pH adjusted to pH 6 and the product extracted with dichloromethane (2×100 ml). The organic layers were dried (MgSO₄) and concentrated. The yellow residue was redissolved in tetrahydrofuran (8 ml) and N,N-carbonyl diimidazolyl (121 mg, 0.74 mmol) and triethylamine (0.095 ml, 0.68 mmol) were added. After 18 hours the solution was poured into aqueous ammonium chloride (100 ml) and extracted with dichloromethane (2×100 ml). The organic layers were dried (MgSO₄) and concentrated in vacuo to give a yellow oil. Flash column chromatography (eluting with 97% dichloromethane, 3% methanol) gave the title compound as a yellow foam.

¹H NMR (300 MHz, CDCl₃): δ=1.25 (d, 6 H), 1.45 (t, 3 H), 3.00 (m, 1 H), 4.10 (q, 2 H), 5.00 (s, 1 H), 5.90 (s, 2 H), 6.65 (s, 1 H), 6.70 (d, 1 H), 7.00 (s, 1 H), 7.20 (d, 1 H), 7.40 (d, 1H), 7.40 (d, 2 H), 7.45 (d, 1 H), 7.80 (s, 1 H), 7.90 (d, 2 H), 8.40 (s, 1 H), 8.60 (s, 1 H)

LRMS (Thermospray): 606.4 (MNH₄⁻)

EXAMPLE 12
N-(4-Iso-propylbenzenesulphonyl)-2-[3-(1-ethyl-6-amido)indolyl]-2-(3,4-methylenedioxyphenyl)acetamide

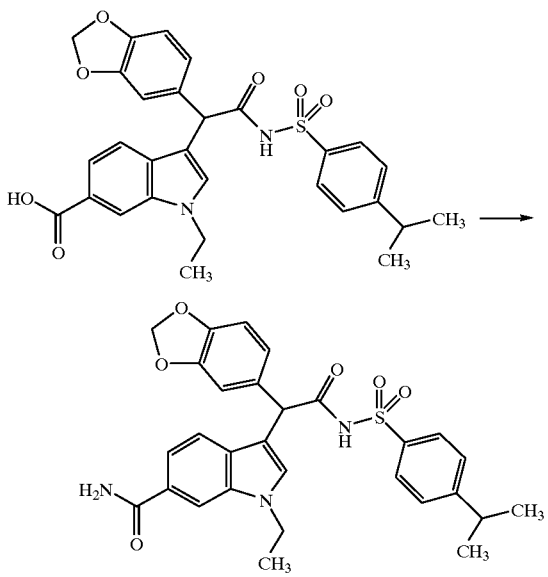

N,N'-carbonyldiimidazole (98 mg, 0.60 mmol) was added to a stirred solution of N-(4-isopropylbenzenesulphonyl)-2-[3-(1-ethyl-6-carboxy)indolyl]-2-(3,4-methylenedioxyphenyl) acetamide (the title compound of Example 4, 300 mg, 0.55 mmol), in dry tetrahydrofuran (8 ml) under nitrogen. The solution was heated to reflux for 12 hours then cooled to room temperature. Ammonia (gas) was bubbled through the solution for 10 minutes and the flask was securely stoppered and stirring continued for a further 48 hours during which time a yellow precipitate formed. The solvent was removed in vacuo and the residue dissolved in dichloromethane (50 ml) the organic layer was washed with aqueous ammonium chloride and then brine before drying (magnesium sulphate) and concentrating in vacuo. The yellow residue was triturated with 5% methanol and 95% dichloromethane to give the product as a pale yellow solid.

$^1$H NMR (400 MHz CD$_3$OD): δ=1.25 (d, 6 H), 1.40 (t, 3 H), 3.00 (sep, 1 H), 4.20 (q, 2 H), 5.05 (s, 1 H), 5.90 (s, 1 H), 6.65 (s, 1 H), 6.70 (s, 2 H), 7.00 (s, 1 H), 7.20 (d, 1 H), 7.40 (d, 2 H), 7.45 (d, 1 H), 7.80 (d, 2 H), 8.00 (s, 1 H).

LRMS (Thermospray): 548.0 (MH$^-$).

EXAMPLE 13
N-(4-Iso-propylbenzenesulphonyl)-2-[3-(1-methyl-6-carboxy)indolyl]-2-(3,4-methylenedioxyphenyl)acetamide
(a) 6-Bromo-1-methylindole

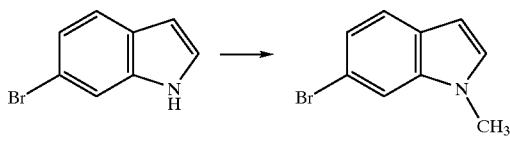

Sodium hydride (4.10 g of a 60% dispersion in paraffin wax) was added to a stirred solution of 6-bromoindole (10 g, 51.3 mmol) in tetrahydrofuran (10 ml) at 0° C. under a nitrogen atmosphere. After 1 hour iodomethane (6.38 ml, 102.6 mmol) was added and the cooling bath removed. After 12 hours methanol was added dropwise until effervescence ceased and then the solvent was removed in vacuo. The thick residue was diluted with dichloromethane and washed first with water then with brine. The organic layer was dried (magnesium sulphate) and concentrated in vacuo to give a dark yellow oil. Filtration through a plug of silica with 90% hexane/10% ethyl acetate as eluant gave the subtitle compound as a pale yellow oil (10.5 g).

$^1$H NMR (300 MHz, CDCl$_3$): δ=3.75 (d, 3 H), 6.40 (d, 1 H), 7.00 (d, 1 H), 7.20 (d, 1 H), 7.50 (d, 1 H), 7.45 (s, 1 H).

LRMS (Thermospray): 209.7 (MH$^+$)

(b) N-(4-Iso-propylbenzenesulphonyl)-2-[3-(1-methyl-6-carboxy)indolyl]-2-(3,4-methylenedioxyphenyl)acetamide

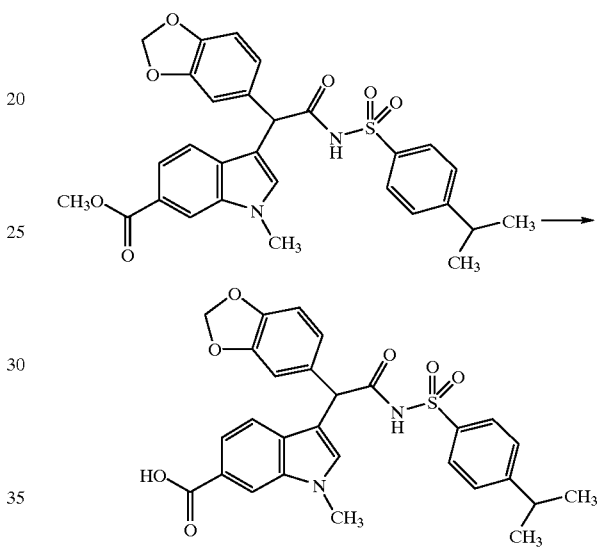

N-(4-Iso-propylbenzenesulphonyl)-2-[3-(1-methyl-6-methoxycarbonyl)indolyl]-2-(3,4-methylenedioxyphenyl) acetamide was prepared by the methods of Examples 1(b), 1(d), 2 and 3, but starting with the subtitle compound of step (a) in place of 6-bromo-1-ethylindole. Then, aqueous KOH (7.3 ml of a 1 M solution) was added to a stirred solution of this product (2 g, 3.65 mmol) in methanol (50 ml) and the solution was heated at reflux for 8 hours. After cooling the methanol was removed in vacuo and the resulting solution was partitioned between 1 M hydrochloric acid (100 ml) and dichloromethane (3×100 ml).

The organic fractions were dried (MgSO$_4$) and concentrated to give a yellow solid. Flash column chromatography (using 95% dichloromethane/5% methanol as eluant) gave the title compound as a white solid (1.44 g).

$^1$H NMR (400 MHz, CDCl$_3$): δ=1.25 (d, 6 H), 3.00 (hept, 1 H), 3.80 (s, 3 H), 5.05 (s, 1 H), 5.95 (s, 2 H), 6.65 (d, 2 H), 6.70 (s, 1 H), 7.00 (s, 1 H), 7.20 (d, 1 H), 7.40 (d, 2 H), 7.65 (d, 1 H), 7.90 (d, 2 H), 8.05 (s, 1 H).

LRMS (Thermospray): 552.7 (MNH$_4^-$)

Examples 14–18 were prepared using the method of Example 13(b), but using the appropriate aromatic sulphonamide in place of 4-isopropylbenzenesulphonamide in the method of Example 3.

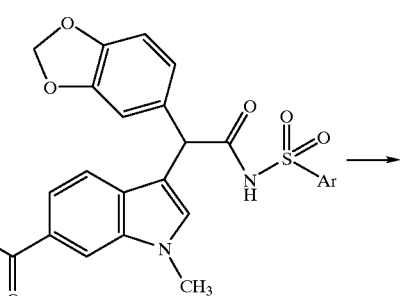

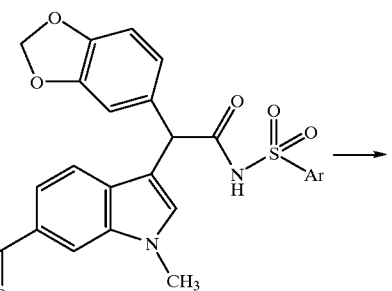

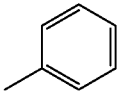

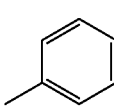

| Example N° | Ar | Physical Data |
|---|---|---|
| 14 | 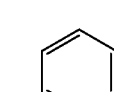 | ¹H NMR(300 MHz, CDCl₃): δ=3.80(s, 3H), 5.00(s, 1H), 5.90(s, 2H), 6.60(s, 1H), 6.65(d, 2H), 7.00(s, 1H), 7.10(d, 1H), 7.45(m 2H), 7.60 (m, 2H), 7.90(d, 2H), 8.00(s, 1H), 8.80(brs, 1H). LRMS(Thermospray): 493.1(MH⁺). |
| 15 | 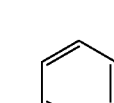 | ¹H NMR(400 MHz, CDCl₃): δ=3.80(s, 3H), 5.00(s, 1H), 6.00 (s, 2H), 6.65(m, 3H), 7.00(s, 1H), 7.20(d, 1H), 7.50(d, 2H), 7.70(d, 1H)7.90(d, 2H), 8.05(s, 1H), 8.45 (brs, 1H). LRMS(APCI): 527.0, 527.8(MH⁺). |
| 16 | 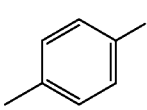 | ¹H NMR(400MHz, CDCl₃): δ=3.80(s, 3H), 5.00(s, 1H), 5.90(s, 2H), 6.65(m, 3H), 7.00(s, 1H), 7.20(d, 1H), 7.65(d, 1H), 7.80(d, 2H), 8.00(s,1H), 8.10(d, 2H), 9.00(s, 1H). LRMS(APCI): 592.9(MNH₄⁺). |
| 17* |  | ¹H NMR(400 MHz, CDCl₃): δ=2.40(s, 3H), 3.40(s 3H), 3.75(s, 3H), 5.05(s, 1H), 5.90(d, 2H), 6.45(s, 1H), 6.70(d, 1H), 6.75(d, 1H), 6.85(d,1H), 7.10(s, 1H), 7.30(m, 3H), 7.60(d, 1H), 7.90(d, 1H), 8.00(s, 1H), 9.20(brs, 1H). LRMS(APCI): 537.0(MH⁺). |
| 18 | CN-phenyl | ¹H NMR(300MHz, CD₃OD): δ=3.75(s, 3H), 4.95(s, 1H), 5.95(d, 2H), 6.65(s, 1H), 6.75(s, 2H), 7.15(s, 1H), 7.25(d 1H), 7.65(d, 1H), 7.95(d, 2H), 8.05(d, 2H), 8.10(s, 1H). LRMS(APCI): 518.3(MH⁺). |
| 19 | CH₃-phenyl | ¹H NMR(300MHz, CDCl₃): δ=2.45(s, 3H), 3.80(s, 3H), 5.00(s, 1H), 5.95(s, 2H), 6.65(m, 3H), 7.00(s, 1H), 7.15(d, 1H), 7.30(d, 2H), 7.60(d, 1H), 7.80(d, 2H), 8.00(s, 1H), 8.70(s, 1H). LRMS(APCI): 507.3(MH⁺) |
| 20 |  | ¹H NMR(300MHz, d₆-DMSO): δ=3.64(s, 3H), 5.23(s, 1H), 5.92(s, 2H), 6.52(s, 1H), 6.60 (d, 1H), 6.68(d, 1H), 6.90(s, 1H), 7.03(d, 1H), 7.35(d, 1H), 7.60(dd, 1H) 7.75(dd, 1H), 7.90 (s, 1H), 8.30(d, 1H), 8.40(d, 1H), 8.49(d, 1H), 8.80(d, 1H). LRMS(APCI): 543.8(MH⁺) m.p.: 238–240° C. dec. |

*See Preparation 11 for preparation of aromatic sulphonamide

Examples 21–24 were prepared by the method of Example 12 from the compounds of Examples 14, 15, 16 and 20 respectively.

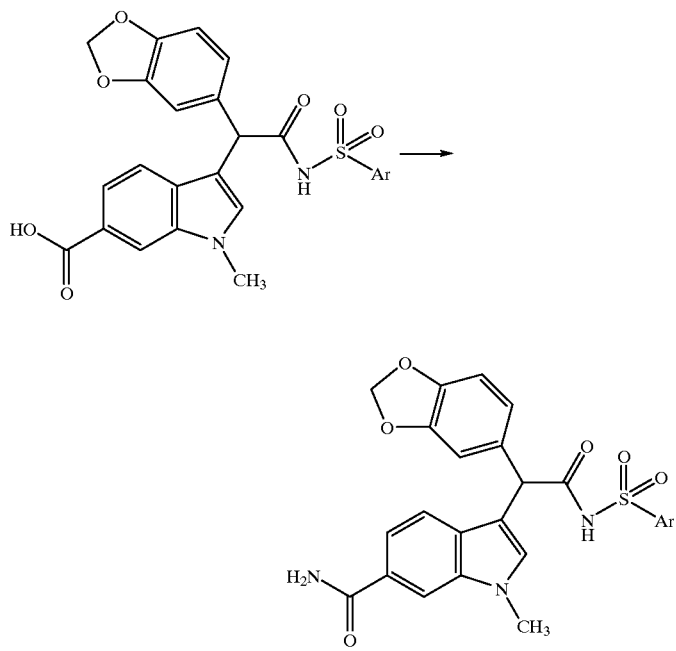
| Example N° | Ar | Physical Data |
|---|---|---|
| 21 | 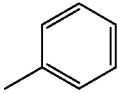 | $^1$H NMR(400MHz, CD$_3$OD): δ=3.70(s, 3H), 5.05(s, 1H), 5.80(s, 2H), 6.80(m, 3H), 6.85(s, 1H), 7.20(m, 2H), 7.40 (m, 3H), 7.90(m, 3H). LRMS(APCI): 492(MH$^+$). |
| 22 | 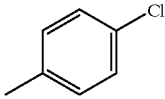 | $^1$H NMR(400 MHz, CD$_3$OD): δ=3.65(s, 3H), 5.05(s, 1H), 5.80(d, 2H), 6.85(m, 3H), 6.95(s, 1H), 7.20(d, 1H), 7.40(d, 2H), 7.45(d, 1H), 7.80(d, 2H), 7.95(s, 1H). LRMS(APCI): 525.9, 526.7(MH$^+$). |
| 23 | 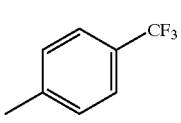 | $^1$H NMR(300 MHz, CD$_3$OD: δ=3.70(s, 3H), 5.00(s, 1H), 5.80(s, 2H), 6.60(d, 1H), 6.70(s, 1H), 6.75(d, 1H), 7.00(s, 1H), 7.30(d, 1H), 7.40(d, 1H), 7.65(d, 2H), 7.90(s, 1H) 8.00(d, 2H). LRMS(APCI): 560.9(MH$^+$). |

-continued
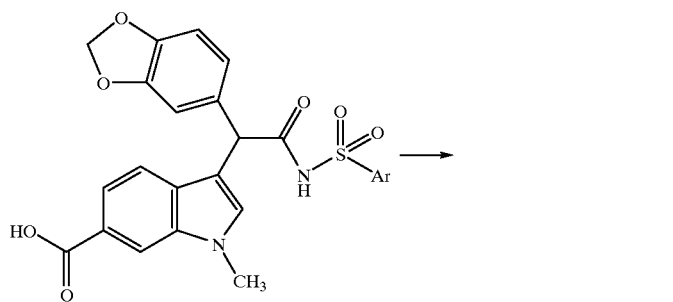
| Example N° | Ar | Physical Data |
|---|---|---|
| 24 | 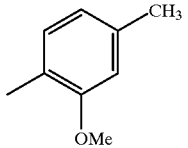 | $^1$H NMR(400 MHz, d$_6$-DMSO): δ=3.64(s, 3H), 4.87(s, 1H), 5.90(d, 2H), 6.64(d, 1H), 6.65(d, 1H), 6.76(s, 1H), 7.02(s, 1H), 7.09(brs, 1H), 7.20(d, 1H), 7.35(d, 1H), 7.55(dd, 1H), 7.60(dd, 1H), 7.78(brs, 1H), 7.90(s, 1H), 8.08(d, 1H), 8.29(d, 1H), 8.39(d, 1H), 8.90(d, 1H). Analysis: Found: C, 57.98; H, 4.62; N, 11.58. C$_{28}$H$_{22}$N$_4$O$_6$S:NH$_3$:H$_2$O: Requires: C, 58.22; H, 4.71; N, 12.12. |
Examples 25–26 were prepared by the method of Example 5 from the compound of Example 17 and the appropriate amine.
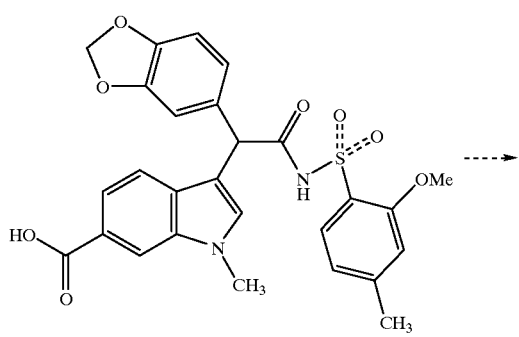

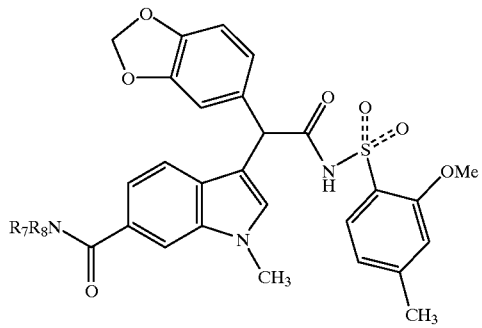

| Example N° | R₇R₈N | Physical Data |
|---|---|---|
| 25 | 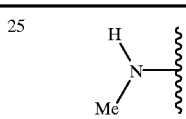 | ¹H NMR(400 MHz, d₆-DMSO): δ=2.70 (s, 3H), 2.80(d, 3H), 3.60(s, 3H), 3.80(s, 3H), 5.20(s, 1H), 5.95 (s, 2H), 6.70(d, 1H), 6.75(s, 1H), 6.80(d, 1H), 6.95(s, 1H), 7.05(s, 1H), 7.20(d, 1H), 7.40(d, 1H), 7.65(d, 1H), 7.90(s, 1H), 8.25(s, 1H), 12.3(brs, 1H). LRMS(APCI): 550.4(MH⁺). |
| 26 | 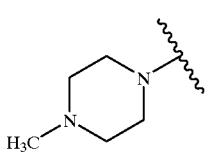 | ¹H NMR(400 MHz, CD₃OD): δ=2.45(s, 3H), 2.50 (s, 3H), 2.60(brs, 4H), 3.65(s, 3H), 3.70(brs, 4H), 3.80 (s, 3H), 5.15(s, 1H), 5.90(s, 2H), 6.70(s, 1H), 6.80(m, 2H), 6.95(s, 1H), 7.00(d, 1H), 7.05(s, 1H), 7.10(d, 1H), 7.40(d, 1H), 7.55(s, 1H), 7.85(d, 1H). LRMS(APCI): 619.9(MH⁺). |

EXAMPLE 27

2-(Dimethylamino)ethyl 3-[1-(1,3-benzodioxol-5-yl)-2-[(2-methoxy-4-methylphenyl)sulfonamido]-2-oxoethyl]-1-methyl-1H-6-indolecarboxylate

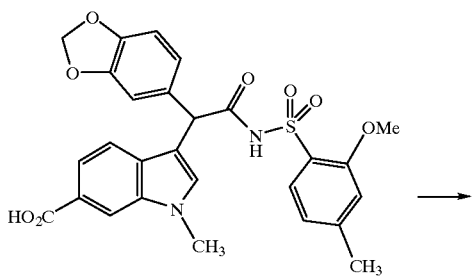

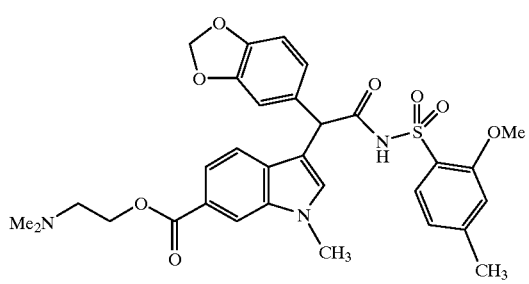

1-(3-Dimethylaminopropyl)-3-ethylcarbodiimide hydrochloride (128 mg, 0.67 mmol) was added to a stirred solution of 3-{1-(1,3-benzodioxol-5-yl)-2-[(2-methoxy-4-methylphenyl)sulfonamido]-2-oxoethyl}-1-methyl-1H-6-indolecarboxylic acid (the product of Example 17, 300 mg, 0.56 mmol), N,N-dimethylaminopyridine (75 mg, 0.61 mmol) and dimethylaminoethanol (0.17 ml, 1.67 mmol) in a mixture of CH₂Cl₂ (9 ml) and DMF (0.5 ml) at room temperature under a nitrogen atmosphere. After 12 h a fine white precipitate had formed. The product was removed by filtration and washed with cold methanol.

¹H NMR (400 MHz, d₆-DMSO): δ=2.40 (s, 9 H), 2.70 (t, 2 H), 3.60 (s, 3 H), 3.75 (s, 3 H), 4.30 (t, 2 H), 5.05 (s, 1 H), 5.90 (s, 2 H), 6.65 (d, 1 H), 6.70 (s, 1 H), 6.75 (d, 1 H), 6.80 (d, 1 H), 6.85 (s, 1 H), 7.20 (s, 1 H), 7.30 (d, 1 H), 7.50 (d, 1 H), 7.60 (d, 1 H), 8.00 (s, 1 H).

LRMS (APCI): 608.9 (MH⁺).

EXAMPLE 28

3-{1-(1,3-Benzodioxol-5-yl)-2-[(4-methylphenyl)sulfonamido]-2-oxoethyl}-1-methyl-1H-6-indolecarboxamide (a) 3-Nitro-4-methylbenzoic acid tert-butyl ester

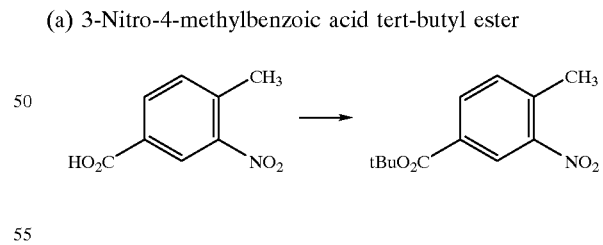

To a solution of 3-nitro-4-methylbenzoic acid (17.3 g 96 mmol) in dichloromethane (250 ml) and tert-butanol (35.8 g 470 mmol) at 0° C. under nitrogen was added 4-dimethylaminopyridine (6 g 50 mmol) and 1-(3-Dimethylaminopropyl)-3-ethylcarbodiimide hydrochloride (25.8 g 140 mmol) and the solution allowed to come to room temperature over 1 hour, then stirred overnight. The solution was poured into 1:1 ethyl acetate:water (800 ml each) and the organic layer washed with aqueous bicarbonate and saturated aqueous sodium chloride, then dried (MgSO₄) and evaporated, to give the product as a clear oil (22.6 g).

¹H NMR (300 MHz CDCl₃): 1.60 (s, 9 H), 2.65 (s, 3 H), 7.40 (d, 1 H) 8.10 (d, 1 H), 8.55 (s, 1H).
LRMS (Thermospray): 238.4 (MH⁻)

(b) Indole 6-tert-butyl ester

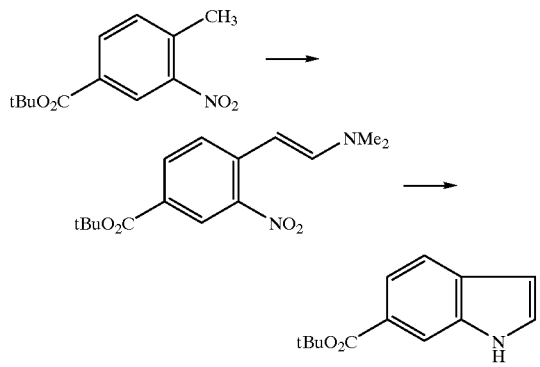

To a solution of the ester from step (a) (23 g 97 mmol) in dimethylformamide (100 ml) was added dimethylformamidedimethyl acetal (50 ml) and pyrrolidine (20 drops). The solution was stirred under nitrogen at 80° C. overnight to give a dark red solution, which was evaporated to dryness to give a dark red oil, which crystallised on standing and was used without further purification.

The crude dimethyl enamine (assumed 97 mmol) was dissolved in toluene (850 ml) and hydrogenated overnight at a pressure of 345 kPa (50 psi) in the presence of 10% palladium-on-charcoal (5 g). Catalyst was removed by filtration and solvents evaporated. The residue was chromatographed on flash silica using dichloromethane eluant to give product as a crystalline solid (12.6 g).

¹H NMR (400 MHz CDCl₃): 1.65 (s, 9 H), 6.60 (s, 1 H), 7.40 (t, 1 H), 7.65 (d, 1 H), 7.80 (d, 1 H), 8.15 (s, 1 H), 8.50 (s, 1 H).

(c) 1-Methylindole 6-tert-butyl ester

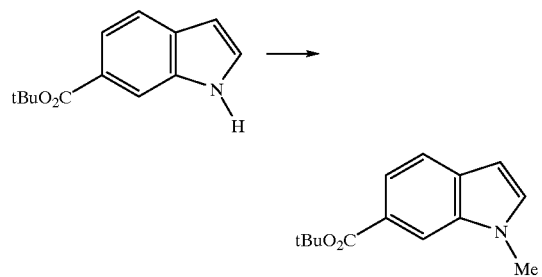

To a solution of the indole from step (b) (12.5 g 57 mmol) in tetrahydrofuran (150 ml) at 0° C. under nitrogen was added sodium hydride as a 60% suspension in oil (2.28 g 57 mmol). When effervescence ceased, methyl iodide (3.6 ml 57 mmol) was added and the solution allowed to come to room temperature. The mixture was stirred for 1 hour, poured into ethyl acetate (500 ml), and washed with water and saturated brine, then dried (MgSO₄) and evaporated to give an oil which was contaminated with hydride oil, but sufficiently pure to continue (14.1 g).

¹H NMR (300 MHz CDCl₃): 1.65 (s, 9 H), 3.85 (s, 3 H), 6.50 (d, 1 H), 7.20 (s, 1 H), 7.60 (d, 1 H), 7.75 (d, 1 H), 8.05 (s, 1 H).

LRMS (Thermospray): 232.2 (MH⁻)

(d) Ethyl 2-[3-(1-methyl-6-carboxy)indolyl]-2-(3,4-methylenedioxyphenyl)acetate

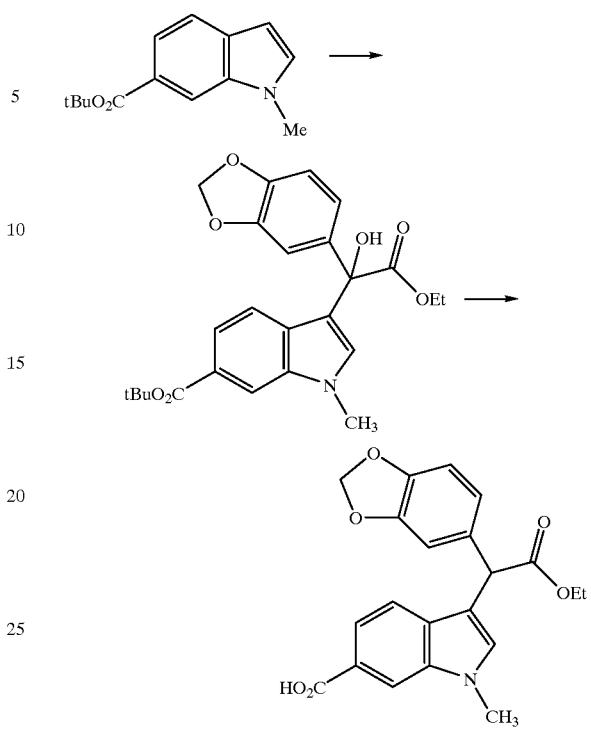

To a solution of boron trifluoride diethyl etherate (14 ml 132 mmol) and triethysilane (40 ml 240 mmol) in dichloromethane (60 ml) at -78° C. under nitrogen was added a solution of the indole from (c) (14 g 60 mmol) and benzodioxole ethylpyruvate (14 g, 66 mmol) in dichloromethane (80 ml) dropwise. The solution was stirred at -78° C. for 30 minutes, then quenched with aqueous hydrochloric acid and the organic layer separated, dried (MgSO₄) and evaporated. The hydroxy intermediate was isolated by flash chromatography using 30% ethyl acetate in hexane eluant as a buff solid (19.38 g). This intermediate (15 g) was dissolved in dichloromethane (50 ml) and triethyl silane (15 g) at 0° C. under nitrogen, and trifluoroacetic acid (50 ml) was added dropwise over 10 minutes. After 1 hour at room temperature the reaction was quenched with water, and the organic layer separated, dried (MgSO₄) and evaporated. Chromatography on flash silica using ethyl acetate eluant gave the acid ester as a pale foam (9.53 g).

¹H NMR (400 MHz CDCl₃): 1.25 (t, 3 H), 3.85 (s, 3 H), 4.20 (m, 2 H), 5.20 (s, 1 H), 5.95 (s, 2 H), 6.70–8.20 (m, 7 H).

(e) Ethyl 2-(1,3-Benzodioxol-5-yl)-2-(6-carbamoyl-1-methyl-1H-3-indolyl)acetate

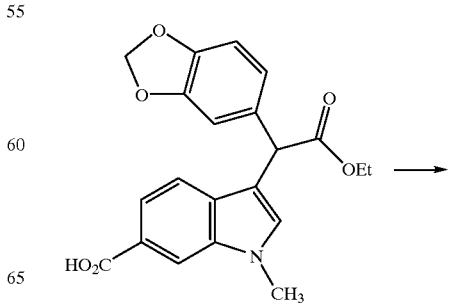

-continued

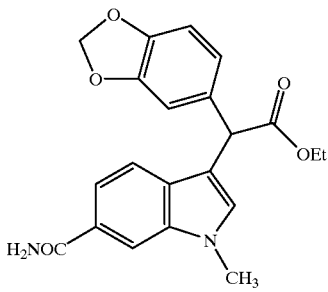

To a solution of the acid (9.43 g 25 mmol) in tetrahydrofuran (125 ml) was added carbonyldiimidazole (4.0 g 25 mmol) and the solution refluxed for 4 hours. The solution was cooled to 0° C. and saturated with gaseous ammonia then stirred overnight. The reaction was concentrated in vacuo and partitioned between ethyl acetate and water. The organic layer was washed twice with water and brine, then dried (MgSO$_4$) and evaporated. Product was isolated by flash chromatography using 2% methanol in dichloromethane eluant to give the amide ester as a pale foam (5.6 g).

$^1$H NMR (300 MHz d$_6$-DMSO): 1.20 (t, 3 H), 3.80 (s, 3 H), 4.15 (q, 2 H), 5.20 (s, 1 H), 5.95 (d, 2 H), 6.80–8.00 (m, 9 H).

LRMS (Thermospray): 381.1 (MH$^-$)

(f) 2-(1,3-Benzodioxol-5-yl)-2-(6-carbamoyl-1-methyl-1H-3-indolyl)acetic acid

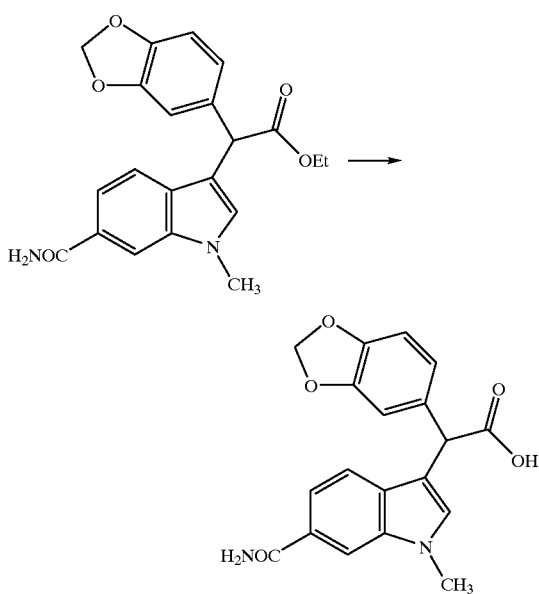

To a solution of the amide ester from step (e) (5.6 g 14.7 mmol) in tetrahydrofuran (60 ml) and methanol (30 ml) was added aqueous sodium hydroxide solution (10 ml of 5M, 50 mmol) dropwise, and the mixture heated at reflux for 9 hours. Solvents were removed in vacuo and the residue dissolved in aqueous sodium hydroxide and washed with dichloromethane. The aqueous layer was acidified with aqueous hydrochloric acid and the product isolated by filtration. Trituration with ethyl acetate gave the product as a white solid (5.1 g).

$^1$H NMR (300 MHz d$_6$-DMSO): 3.80 (s, 3 H), 5.15 (s, 1 H), 6.00 (d, 2 H), 6.80–8.00 (m, 9 H).

LRMS (Thermospray): 353.5 (MH$^-$)

(g) 3-{1-(1,3-Benzodioxol-5-yl)-2-[(4-methylphenyl)sulfonamido]-2-oxoethyl}-1-methyl-1H-6-indolecarboxamide

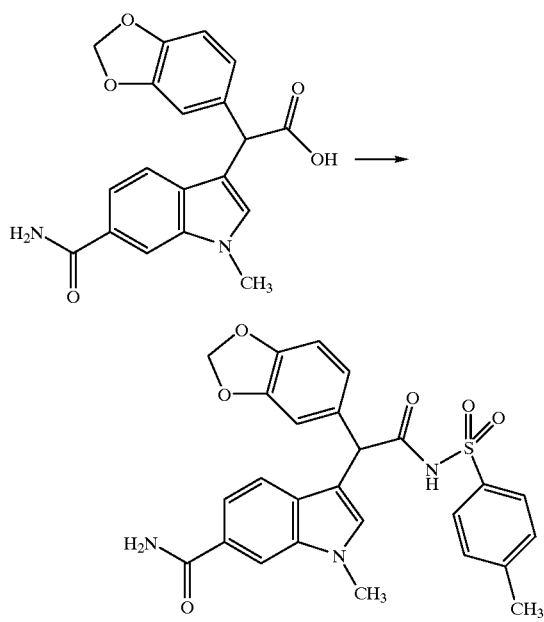

1-(3-Dimethylaminopropyl)-3-ethylcarbodiimide hydrochloride (65 mg, 0.34 mmol) was added to a stirred solution 2-(1,3-benzodioxol-5-yl)-2-(6-carbamoyl-1-methyl-1H-3-indolyl)acetic acid (from step (f), 100 mg, 0.28 mmol), dimethylaminopyridine (45 mg, 0.37 mmol) and p-toluenesulphonamide (53 mg, 0.31 mmol) in dichloromethane (5 ml) and dimethylformamide (1 ml) at room temperature under a nitrogen atmosphere. After 14 h the solvent was removed in vacuo and the product was extracted from 1 N hydrochloric acid (50 ml) with ethyl acetate (2×50 ml). The organic layers were dried and concentrated to give a fawn foam. Flash column chromatography (elution with 95% dichloromethane/5% methanol) gave the product (95 mg) as a white solid.

$^1$H NMR (300 MHz, CD$_3$OD): δ=2.40 (s, 3 H), 3.75 (s, 3 H), 5.05 (s, 1 H), 5.90 (s, 2 H), 6.60 (m, 3 H), 6.90 (s, 1 H), 7.20 (d, 1 H), 7.30 (d, 2 H), 7.40 (d, 1 H), 7.80 (d, 2 H), 7.95 (s, 1 H).

LRMS (APCI): 506 (MH$^+$).

Examples 29–45 were prepared by reacting the compound of Example 28(f) with the appropriate aromatic sulphonamide using the method of Example 28(g).

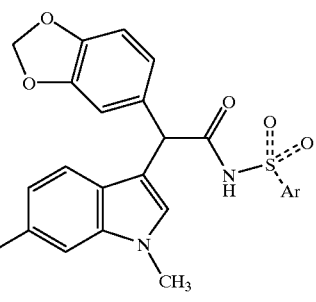

| Example N° | Ar | Physical Data |
|---|---|---|
| 29 | MeO-2,5-dimethylphenyl (2-OMe, 5-Me) | ¹H NMR(400 MHz, d₆-DMSO): δ=2.35(s, 3H), 3.60(s, 3H), 3.75(s, 3H), 5.20(s, 1H), 5.95(d, 2H), 6.60–8.00(m, 12H). LRMS(Thermospray) 536.4(MH⁺) |
| 30 | 2,5-dimethylthiophene | ¹H NMR(300 MHz, CD₃OD): δ=2.45(s, 3H), 3.80(s, 3H), 5.00(s, 1H), 5.85(s, 2H), 6.90(m, 4H), 7.00(s, 1H), 7.20(d, 1H), 7.40(d, 1H), 7.50(d, 1H), 7.90(s, 1H). LRMS(APCI): 512.1 (MH⁺). |
| 31 | 5-methyl-2-(dimethylamino)pyridine | ¹H NMR(300MHz, CD₃OD): δ=3.10(s, 6H), 3.60(s, 3H), 5.00(s, 1H), 5.80(s, 2H), 6.45(d, 1H), 6.65(m, 3H), 7.00(s, 1H), 7.20(d, 1H), 7.40(d, 1H), 7.80(d, 1H), 7.90(s, 1H), 8.50(s, 1H). LRMS(APCI): 536.2(MH⁺). |
| 32 | 3-methylpyridine | ¹H NMR(300 MHz, d₆-DMSO): δ=3.70(s, 3H), 4.80(s, 1H), 5.90(d, 2H), 6.65(d, 1H), 6.70(d, 1H), 6.80(s, 1H), 7.10–7.40(m, 5H), 7.90(s, 1H), 8.00(d, 1H), 8.50(d, 1H), 8.80(s, 1H). LRMS(APCI): 493.8(MH⁺). |
| 33 | 1,5-dimethyltetrazole | ¹H NMR(400 MHz, CD₃OD): δ=3.80(s, 3H), 4.00(s, 3H), 5.00(s, 1H), 5.80(s, 2H), 6.70(d, 1H), 6.80(m, 2H), 7.20(m, 4H). LRMS(APCI): 498(MH³⁰. |
| 34 | 3-chlorophenyl | ¹H NMR(400 MHz, d₆-DMSO): δ=3.75(s, 3H), 5.05(s, 1H), 5.95(s, 2H), 6.70(d, 1H), 6.75(s, 1H), 6.80(d, 1H), 7.05(s, 1H), 7.20(d, 1H), 7.45(d, 1H), 7.60(t, 1H), 7.75(m, 3H), 8.00(s, 1H). LRMS(Thermospray): 525.7, 527.3(MH⁺). |

-continued

| Example N° | Ar | Physical Data |
|---|---|---|
| 35 | phenyl | ¹H NMR(300MHz, CDCl₃): 3.85(s, 3H), 4.70(s, 2H), 5.15(s, 1H), 6.00(s, 2H), 6.80–8.00(m, 14H) 11.95(s, 1H). LRMS(Thermospray): 505.4(MH⁺) |
| 36 | 2-methyl-4-chloro-methoxyphenyl | ¹H NMR(300 MHz, d₆-DMSO): 3.65(s, 3H), 3.75(s, 3H), 5.20(s, 1H) 5.95(d, 2H)6.60–8.00(m, 12H), 12.60(s, 1H). LRMS(Thermospray): 555.7(MH⁺) |
| 37 | 4-methylphenyl-CH₂CO₂Et | ¹H NMR(400 MHz, CDCl₃): δ=1.10(t, 3H), 3.55(s, 2H), 3.60(s, 3H), 4.00(q, 2H), 4.80(s, 1H), 5.75(s, 2H), 6.60(s, 3H), 6.80(s,1H), 7.00(d, 1H), 7.25(m, 3H), 7.75(s, 1H), 7.80(d, 2H). LRMS(APCI): 578.5(MH⁺). |
| 38 | 2-methoxy-methylphenyl | ¹H NMR(400 MHz, CDCl₃): δ=2.50(s, 3H), 3.70(s, 3H), 5.05(s, 1H), 5.80(s, 2H), 6.60(d, 1H), 6.70(d, 1H), 6.75(s, 1H), 7.00(s, 1H), 7.05(d, 1H), 7.10(d, 1H), 7.25(d, 1H), 7.85(s, 1H), 7.90(d, 1H). LRMS(APCI):nl 508.0 (MH⁺). |
| 39 | 2-methoxyphenyl | ¹H NMR(400 MHz, d₆-DMSO): 3.65(s, 3H), 3.75(s, 3H), 5.20(s, 1H), 5.95(d, 2H), 6.60–8.00(m, 13H), 12.40(s, 1H). |
| 40‡ | 2-chloro-4-methyl-5-methoxybenzyl | ¹H NMR(400MHz, d₆-DMSO): 2.40(s, 3H), 3.65(s, 3H), 3.80(s, 3H), 5.20(s, 1H), 5.95(d, 2H), 6.60–8.00(m, 11H), 12.50(s, 1H). |

‡

35
-continued

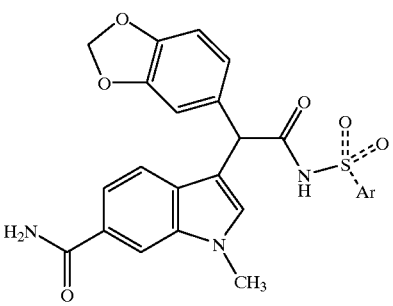

| Example N° | Ar | Physical Data |
|---|---|---|
| 41* | [4-methylphenyl-CH=CH-CO2Et] | ¹H NMR(400MHz, CD₃OD): δ=2.45(t, 3H), 3.75(s, 3H), 4.35(q, 2H), 5.15(s, 1H), 5.95(s, 2H), 6.80(m, 4H), 6.95 (s, 1H), 7.35(d, 1H), 7.55(d, 1H), 7.75(d, 2H), 7.80(s, 1H), 7.95(d, 2H), 8.00(s, 1H). |
| 42† | [2-methyl-5-pyridyl] | ¹H NMR(400MHz, d₆-DMSO): δ=3.40(s, 3H), 3.80(s, 3H), 5.20(s, 1H), 6.00(s, 2H), 6.70(d, 1H), 6.75(s, 1H), 6.80(d, 1H), 7.00(s, 1H), 7.20 (m, 2H), 7.45(d, 1H), 7.80(m, 2H), 7.95(s, 1H), 8.45(s, 1H). LRMS(APCI): 506.7(MH⁺). |
| 43 | [4-methylphenyl-CO2Me] | ¹H NMR(400 MHz, CD₃OD): δ=3.70(s, 3H), 3.95(s, 3H), 5.00(s, 1H), 5.80(s, 2H), 6.60(d, 1H), 6.80(s, 1H), 6.85(d, 1H), 7.05(s, 1H), 7.25(d, 1H), 7.40(d, 1H), 7.80(d, 2H), 7.90(s, 1H), 7.95(d, 2H). LMRS(Thermospray): 550.0(MH⁺) |
| 44 | [3-methyl-4-morpholino-acetylphenyl] | ¹H NMR(400 MHz, CD₃OD): δ=2.70(m, 2H), 2.75(s, 3H), 2.85 (m, 2H), 3.75(m, 4H), 3.95(s, 3H), 5.25(s, 1H), 6.00(d, 2H), 6.80(m, 3H), 7.10(s, 1H), 7.40(d, 1H), 7.50(d, 1H), 7.60(d, 1H), 8.05(s, 1H), 8.30(d, 1H),8.80(s, 1H). LRMS(APCI): 619.9(MH⁺). |

36
-continued

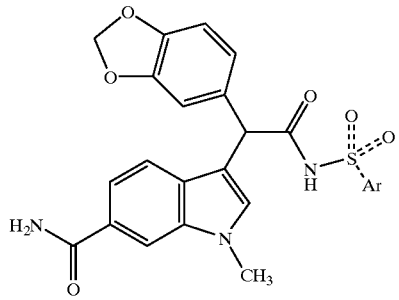

| Example N° | Ar | Physical Data |
|---|---|---|
| 45 | [2-methylphenyl-CO2Me] | ¹H NMR(300MHz, d₆DMSO): δ=3.70(s, 3H), 3.75(s, 3H), 4.96 (br, 1H), 5.90(d, 2H), 6.70–6.78(m, 2H), 6.84(s, 1H), 7.10(brs, 1H), 7.22(s, 1H), 7.32(d, 1H), 7.40–7.60(m, 4H), 7.80(brs, 1H), 7.90–7.95(m, 2H), 12.50(brs. 1H exchangeable), Analysis: Found: C, 54.90; H, 3.94; N, 6.98. C₂₇H₂₃N₂O₈S; 0.6CH₂Cl₂ Requires: C, 55.20; H, 4.06; N, 7.00. |

‡See Preparation 8 for sulphonamide preparation
*See Preparation 3 for sulphonamide preparation
†See Preparation 4 for sulphonamide preparation

EXAMPLE 46
Ethyl 3-(4-[2-(6-carbamoyl-1-methyl-1H-3-indolyl)-2-(1,3-benzodioxol-5-yl)acetyl]sulfamoylphenyl)propanoate

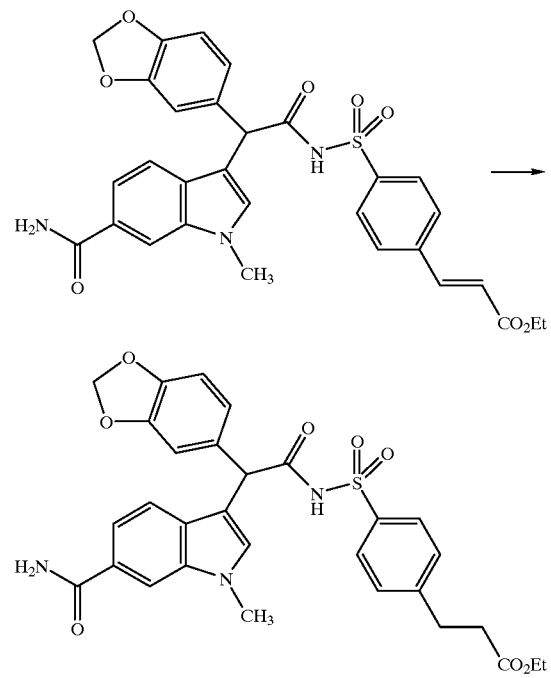

Ethyl (E)-3-(4-[2-(6-carbamoyl-1-methyl-1H-3-indolyl)-2-(1,3-benzodioxol-5-yl)acetyl]sulfamoylphenyl)-2-propenoate (the compound of Example 41, 0.24 g, 0.40 mmol) was dissolved in ethanol (5 ml) and 5% palladium-on-carbon (24 mg) was added. The mixture was placed in a pressure vessel and a hydrogen pressure of 345 kpa (50 psi) was maintained for 48 h. The reaction mixture was filtered through Arbocel™ and concentrated in vacuo. Flash column chromatography (elution with 5% methanol/90% dichloromethane) gave the product (70 mg).

$^1$H NMR (400 MHz, CD$_3$OD): δ=1.20 (t, 3 H), 2.60 (t, 2 H) 3.00 (t, 2 H), 3.75 (s, 3 H), 4.05 (q, 2 H), 5.05 (s, 1 H), 5.85 (s, 2 H), 6.60 (s, 1 H), 6.70 (s, 2 H), 6.90 (s, 1 H), 7.20 (d, 1 H), 7.30 (d, 2 H), 7.40 (d, 1 H), 7.80 (d, 2 H), 7.90 (s, 1 H).

LRMS (APCI): 591.9 (MH$^-$).

EXAMPLE 47

2-(4-[2-(1,3-Benzodioxol-5-yl)-2-(6-carbamoyl-1-methyl-1H-3-indolyl)acetyl]-sulfamoylphenyl)acetic acid

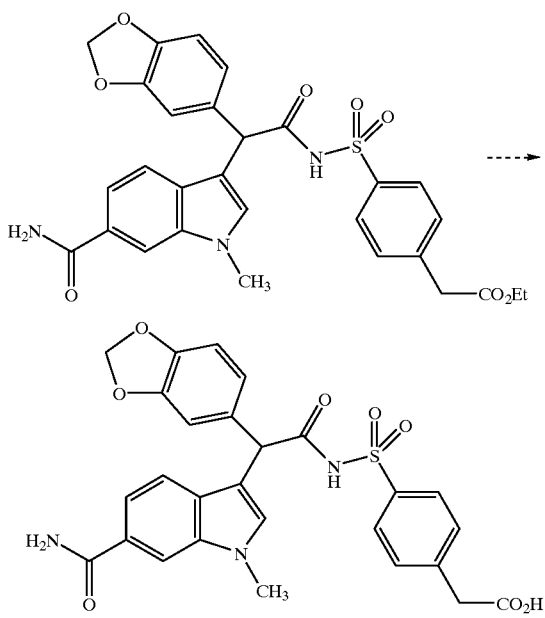

1 M Sodium hydroxide solution (0.57 ml) was added to a stirred solution of ethyl 2-(4-[2-(1,3-benzodioxol-5-yl)-2-(6-carbamoyl-1-methyl-1H-3-indolyl)acetyl] sulfamoylphenyl) acetate (the product of Example 37, 110 mg, 0.19 mmol) in aqueous dioxan (8 ml dioxan:2 ml H$_2$O) at room temperature. After 1 h the solvent was removed in vacuo. The reaction mixture was diluted with ethyl acetate and poured into 0.5M hydrochloric acid (50 ml) and extracted with ethyl acetate (2×50 ml). The organic layers were dried (magnesium sulphate) and concentrated in vacuo to give a yellow foam. Flash column chromatography (elution with 95% dichloromethane/5% methanol) gave the product as a white solid (90 mg).

$^1$H NMR (400 MHz CDCl$_3$): δ3.40 (s, 2 H), 3.90 (s, 3 H), 5.20 (s, 1 H), 6.00 (s, 2 H), 6.80 (m, 3 H), 7.00 (s, 1 H), 7.30 (d, 1 H), 7.60 (d, 2 H), 7.65 (s, 1 H), 8.00 (s, 1 H), 8.10 (d, 2 H).

LRMS (APCI): 549.9 (MH$^+$).

Examples 48–50 were made using the method of Example 47, starting with the compounds of Examples 45, 43 and 46 respectively.

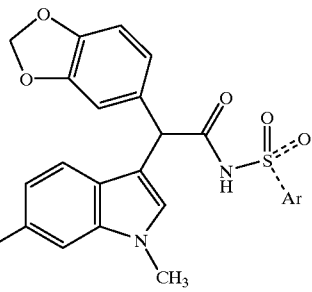

| Example N° | Ar | Physical Data |
|---|---|---|
| 48 | 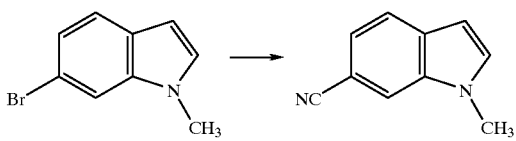 2-methylphenyl, CO$_2$H | $^1$H NMR(300 MHz, d$_6$-DMSO): δ=3.75(s, 3H), 5.26(s, 1H), 5.96(s, 2H), 6.70–6.82(m, 3H), 7.10–7.17(m, 2H), 7.27(d, 1H), 7.46 (d, 1H), 7.60–7.86(m, 4H), 7.96(s, 1H), 8.00 (d, 1H). LRMS(APCI): 536.1(MH$^+$) |
| 49 | 4-methylphenyl, CO$_2$H | $^1$H NMR(400 MHz, CD$_3$OD: δ=3.80(s, 3H), 5.05(s, 1H), 5.80(d, 2H), 6.60(s, 1H), 6.70(d, 1H), 6.75(d, 1H), 6.90(s, 1H), 7.20(d, 1H), 7.40(d, 1H), 7.85(s, 1H), 7.90(d, 2H), 8.00(d, 2H). LRMS(APCI): 536.0(MH$^+$); |
| 50 | 4-methylphenyl-CH$_2$CH$_2$-CO$_2$H | $^1$NMR(300 MHz, CD$_3$OD): δ=2.80(t, 2H), 3.00(t, 2H), 3.75(s, 3H), 5.00(s, 1H), 5.80(d, 2H), 6.60(m, 3H), 6.90 (s, 1H), 7.20(d, 1H), 7.30(d, 2H), 7.40(d, 1H), 7.80(d, 2H), 7.90 (s, 1H). LRMS(APCI): 563.8(MH$^+$). |

EXAMPLE 51

3-1-(1,3-Benzodioxol-5-yl)-2-[(4-isopropylphenyl)sulfonamido]-2-oxoethyl-6-cyano-1-methyl-1H-indole (a) 6-cyano-1-methylindole Cuprous cyanide (12.8 g, 143 mmol) was added to a stirred solution of 6-bromo-1-methylindole (10 g, 47 mmol) in N-methylpyrrolidinone (60 ml) under a nitrogen atmosphere. The reaction mixture was heated at 150° C. for 48 h. The reaction mixture was cooled and partitioned between ethyl acetate (200 ml) and aqueous ammonia (200 ml of 0.88 M). The organic layer was washed with brine (3×200 ml), dried (MgSO$_4$) and concentrated. Flash column chromatography (elution with 70% hexane/30% ethyl acetate) gave the product as a crystalline white solid (5.3 g).

¹H NMR (400 MHz, CDCl₃): δ=3.80 (s, 3 H), 6.60 (s, 1 H), 7.25 (d, 1 H), 7.35 (d, 1 H), 7.70 (d, 2 H).
LRMS (Thermospray): 174.1 (MNH₄⁺).

(b) 3-[1-(1,3-Benzodioxol-5-yl)-2-[(4-isopropylphenyl)sulfonamido]-2-oxoethyl]-6-cyano-1-methyl-1H-indole

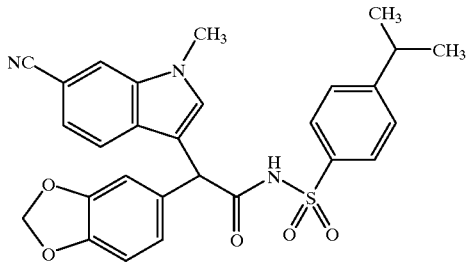

The title compound was prepared using the methods of Examples 1(d), 2 and 3, but starting with the compound of step (a) in place of 6-methoxycarbonyl-1-ethylindole.

¹H NMR (400 MHz, CDCl₃): δ=1.30 (d, 6 H), 3.00 (m, 1 H), 3.80 (s, 3 H), 5.00 (s, 1 H), 6.00 (s, 2 H), 6.60 (s, 1 H), 6.65 (d, 1 H), 6.70 (d, 1 H), 7.00 (s, 1 H), 7.20 (s, 2 H), 7.40 (d, 2 H), 7.60 (s, 1 H), 7.85 (d, 2 H), 8.20 (s, 1 H).
LRMS (APCI): 516.2 (MH⁺).

EXAMPLE 52
3-[1-(1,3-Benzodioxol-5-yl)-2-[(4-isopropylphenyl)sulfonamido]-2-oxoethyl]-1-methyl-6-(2H-1,2,3,4-tetrazol-5-yl)-1H-indole

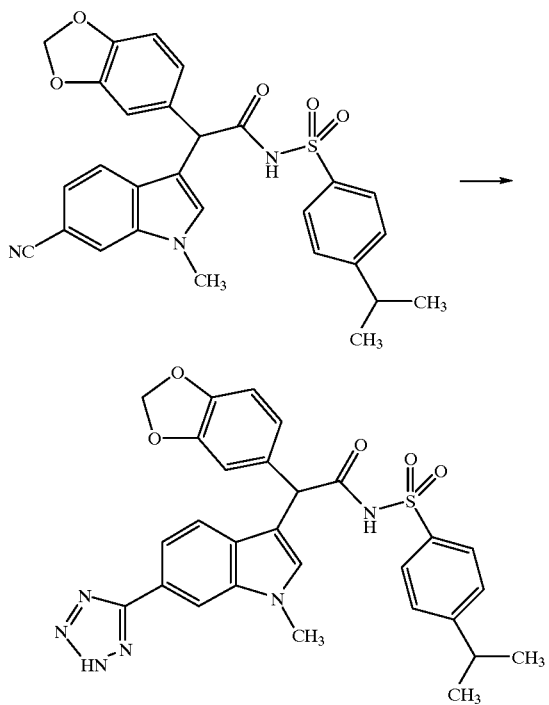

Trimethylsilylazide (0.23 ml, 1.74 mmol) and dibutyl tin oxide (52 mg, 0.2 mmol) were added to a solution of 3-{1-(1,3-benzodioxol-5-yl)-2-[(4-isopropylphenyl)sulfonamido]-2-oxoethyl}-6-cyano-1-methyl-1H-indole (the product of Example 51, 300 mg 0.58 mmol) in toluene (10 ml) and the solution was heated at reflux under an atmosphere of nitrogen for 14 h. Tlc analysis showed incomplete reaction. Further aliquots of trimethylsilylazide (0.23 ml, 1.74 mmol) and dibutyl tin oxide (52 mg, 0.2 mmol) were added and heating was continued at reflux for a further 24 h. The reaction was cooled and concentrated. The crude product was purified by flash column chromatography (gradient elution from 95% dichloromethane/5% methanol to 90% dichloromethane/10% methanol) giving a pale pink solid (100 mg).

¹H NMR (300 MHz d₆-DMSO): δ=1.20 (d, 6 H), 3.00 (m, 1 H), 3.80 (s, 3 H), 5.10 (s, 1 H), 5.95 (s, 2 H), 6.70 (d, 1 H), 6.75 (s, 1 H), 6.80 (d, 1 H), 7.10 (s, 1 H), 7.25 (d, 1 H), 7.40 (d, 2 H), 7.60 (d, 1 H), 7.75 (d, 2 H), 8.00 (s, 1 H).
LRMS (APCI): 559 (MH⁺).

EXAMPLE 53
6-(Aminomethyl)-3-1-(1,3-benzodioxol-5-yl)-2-[(4-isopropylphenyl)sulfonamido]-2-oxoethyl-1-methyl-1H-indole

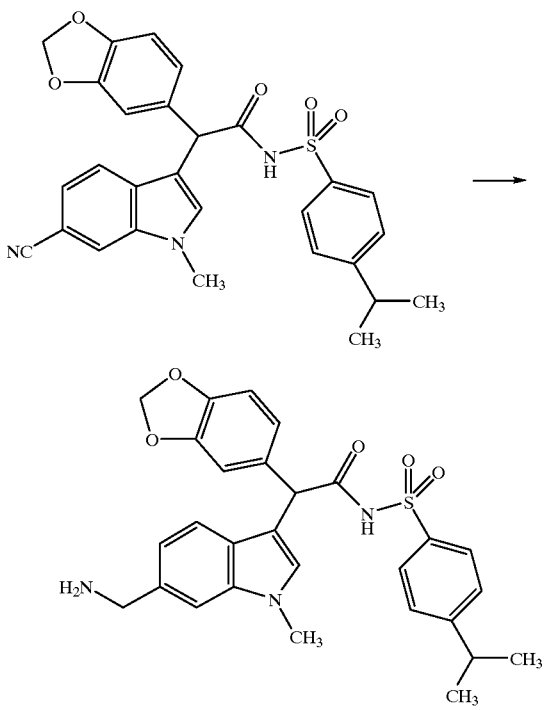

Sodium borohydride (213 mg, 5.6 mmol) was added slowly to a vigorously stirred solution of 3-{1-(1,3-benzodioxol-5-yl)-2-[(4-isopropylphenyl)sulfonamido]-2-oxoethyl}-6-cyano-1-methyl-1H-indole (the product of Example 51, 290 mg, 0.56 mmol) and CoCl₂.6H₂O (200 mg, 0.84 mmol) in methanol (12 ml) at room temperature under a nitrogen atmosphere. After 2 h the reaction was complete and 2N hydrochloric acid (4 ml) was added dropwise. Stirring was continued until the black precipitate had dissolved. The methanol was removed in vacuo and the product was extracted from water with dichloromethane(50 ml) and ethyl acetate (50 ml). The organic layers were combined, dried (MgSO₄) and concentrated. The crude product was purified by flash column chromatography (elution with 90% dichloromethane/10% methanol/2% acetic acid) giving a brown gum. The residue was dissolved in methanol (10 ml) and stirred with charcoal for 30 mins. Filtration and concentration gave the product as a yellow oil.

¹H NMR (300 MHz, CD₃OD): δ=1.20 (d, 6 H), 2.95 (m, 1 H), 3.65 (s, 3 H), 4.20 (s, 2 H), 5.00 (s, 1 H), 5.80 (d, 2 H), 6.60 (d, 1 H), 6.70 (d, 1 H), 6.75 (s, 1 H), 6.80 (s, 1 H), 7.00 (d, 1 H), 7.25 (d, 3 H), 7.40 (s, 1 H), 7.80 (d, 2 H).

EXAMPLE 54

3-{1-(1,3-Benzodioxol-5-yl)-2-[(4-isopropylphenyl)sulfonamido]-2-oxoethyl}-6-(4,5-dihydro-1H-2-imidazolyl)-1-methyl-1H-indole

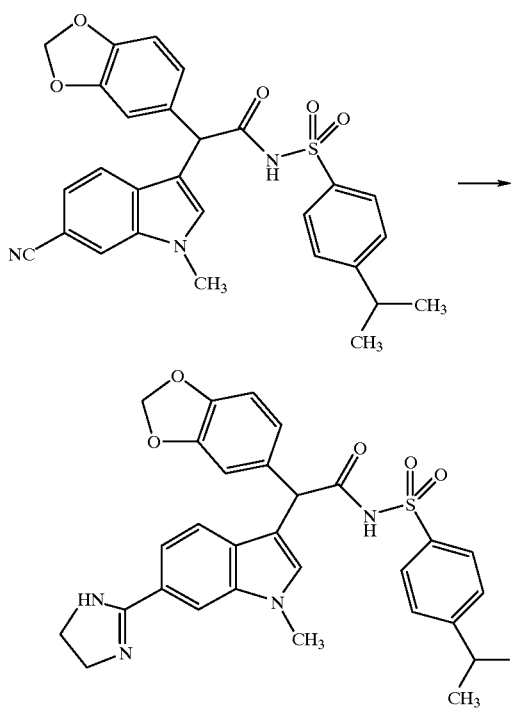

Diethyldithiophosphate (1.3 ml, 7.7 mmol) was added to 3-{1-(1,3-benzodioxol-5-yl)-2-[(4-isopropylphenyl)sulfonamido]-2-oxoethyl}-6-cyano-1-methyl-1H-indole (the product of Example 51, 800 mg, 1.5 mmol) in a mixture of ethanol (10 ml) and water (5 drops). The reaction was heated at reflux with stirring for 14 h. After cooling the solvent was removed in vacuo and the residues purified by flash column chromatography (elution with 98% dichloromethane/2% methanol) to give a brown oil. This residue was dissolved in ethylenediamine and the reaction mixture heated at reflux for 3 h. After cooling the ethylenediamine was removed in vacuo. Hydrochloric acid (10 ml) was added and the resulting precipitate was filtered and washed with dichloromethane and methanol. Flash column chromatography (elution with 80% dichloromethane/20% methanol/5%NH$_3$) gave the product as a white solid.

$^1$H NMR (300 MHz, d$_6$-DMSO): δ=1.20 (d, 6 H), 2.80 (m, 1 H), 3.80 (s, 3 H), 3.95 (s, 4 H), 4.80 (s, 1 H), 5.85 (s, 2 H), 6.70 (d, 1 H), 6.75 (d, 1 H), 6.80 (s, 1 H), 7.20 (d, 2 H), 7.35 (s, 1 H), 7.40 (d, 1 H), 7.55 (d, 1 H), 7.60 (d, 2 H), 8.05 (s, 1 H).

LRMS (Electrospray): 559.1 (MH$^-$).

EXAMPLE 55

3-{1-(1,3-Benzodioxol-5-yl)-2-[(4-methylphenyl)sulfonamido]-2-oxoethyl}-6-bromo-1-methyl-1H-indole

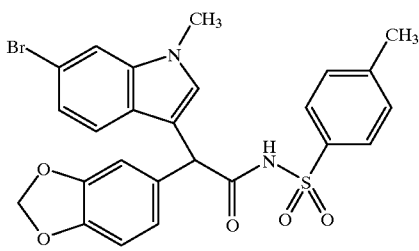

→

The title compound was prepared from the compound of Example 13(a), using the methods of Examples 1(d), 2 and 3, and using 4-methylbenzenesulphonamide in place of 4-isopropylbenzenesulphonamide in the last step.

$^1$H NMR (300 MHz, CDCl$_3$): δ=2.40 (s, 3 H), 3.70 (s, 3 H), 4.90 (s, 1 H), 5.90 (s, 2 H), 6.60 (s, 1 H), 6.65 (d, 1 H), 6.70 (d, 1 H), 6.75 (s, 1 H), 6.90 (d, 1 H), 7.05 (d, 1 H), 7.20 (d, 2 H), 7.40 (s, 1 H), 7.80 (d, 2 H), 8.20 (brs, 1 H).

EXAMPLE 56

3-{1-(1,3-Benzodioxol-5-yl)-2-[(4-isopropylphenyl)sulfonamido]-2-oxoethyl}-6-bromo-1-methyl-1H-indole

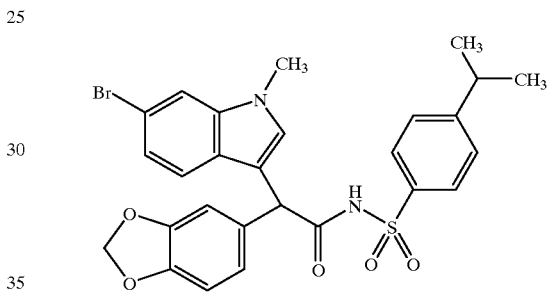

The title compound was prepared from the compound of Example 13(a), using the methods of Examples 1(d), 2 and 3.

$^1$H NMR (300 MHz, d$_6$-DMSO): δ=1.20 (d, 6 H), 3.00 (m, 1 H), 3.60 (s, 3 H), 5.00 (s, 1 H), 5.90 (s, 2 H), 6.70 (m, 3 H), 6.85 (s, 1 H), 6.95 (d, 1 H), 7.00 (d, 1 H), 7.40 (d, 2 H), 7.60 (s, 1 H), 7.75 (d, 2 H).

LRMS (APCI): 568.9, 571.2 (MH$^-$).

Analysis: found C, 54.82; H, 4.39; N, 4.53; C$_{27}$H$_{25}$N$_2$O$_5$SBr.H$_2$O requires C, 55.20; H, 4.63; N, 4.77.

EXAMPLE 57

Ethyl (E)-3-[3-{1-(1,3-benzodioxol-5-yl)-2-[4-isopropylphenyl)sulfonamido]-2-oxoethyl}-1-methyl-1H-6-indolyl]-2-propenoate

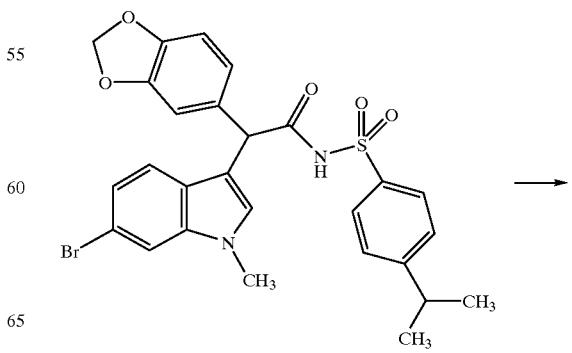

→

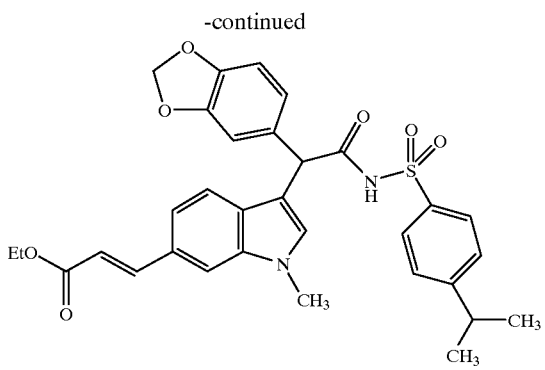

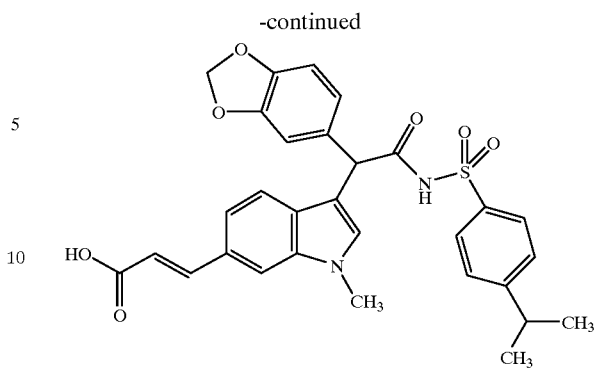

Palladium acetate (9.5 mg, 0.42 mmol) was added to a stirred solution of 3-{1-(1,3-benzodioxol-5-yl)-2-[(4-isopropylphenyl)sulfonamido]-2-oxoethyl}-6-bromo-1-methyl-1H-indole (the product of Example 56, 200 mg, 0.35 mmol), ethyl acrylate (0.048 ml, 0.44 mmol), triethylamine (0.146 ml, 1 mmol) and tri-o-tolylphosphine (32 mg, 0.1 mmol) in acetonitrile (10 ml) at room temperature under a nitrogen atmosphere. The solution was heated at reflux for 2 h. After cooling the mixture was poured into brine (50 ml) and extracted with ethyl acetate (2×50 ml). The organic layers were washed with water (50 ml), dried (MgSO$_4$) and concentrated to give a grey foam. Purification by flash column chromatography (elution with 95% dichloromethane/5% methanol) gave the product as a pale yellow foam.

$^1$H NMR (400 MHz, CDCl$_3$): δ=1.30 (d, 6 H), 1.35 (t, 3 H), 3.00 (m, 1 H), 3.75 (s, 3 H), 4.30 (q, 2 H), 5.00 (s, 1 H), 5.95 (s, 2 H), 6.40 (d, 1 H), 6.70 (m, 3 H), 6.90 (s, 1 H), 7.10 (d, 1 H), 7.20 (d, 1 H), 7.35 (d, 2 H), 7.40 (s, 1 H), 7.80 (d, 1 H), 7.85 (d, 2 H), 8.20 (brs, 1 H).

LRMS (Thermospray): 589.5 (MH$^+$).

EXAMPLE 58

(E)-3-[3-{1-(1,3-Benzodioxol-5-yl)-2-[(4-isopropylphenyl)sulfonamido]-2-oxoethyl}-1-methyl-1H-6-indolyl]-2-propenoic acid

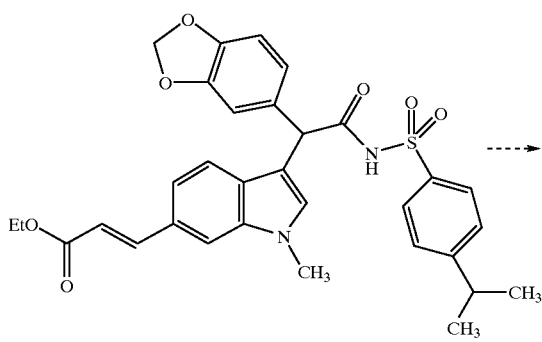

Ethyl (E)-3-(3-1-(1,3-benzodioxol-5-yl)-2-[(4-isopropylphenyl)sulfonamido]-2-oxoethyl-1-methyl-1H-6-indolyl)-2-propenoate (the product of Example 57, 120 mg, 0.2 mmol) was dissolved in a 1:1 mixture of tetrahydrofuran and methanol (5 ml). Sodium hydroxide solution (0.6 ml of 1N NaOH) was added and the mixture was heated to reflux with stirring. After 3 h the solvent was removed in vacuo and the product was extracted from 1N hydrochloric acid (50 ml) with ethyl acetate (2×50 ml). The organic layers were dried (MgSO$_4$) and concentrated. Purification by flash column chromatography (gradient elution from 100% dichloromethane to 90% dichloromethane/10% methanol/1% acetic acid) gave the product as a pale green foam (90 mg).

$^1$H NMR (300 MHz, CDCl$_3$): δ=1.30 (d, 6 H), 3.00 (m, 1 H), 3.80 (s, 3 H), 5.00 (s, 1 H), 5.95 (s, 2 H), 6.40 (d, 1 H), 6.65 (m, 3 H), 6.90 (s, 1 H), 7.20 (m, 3 H), 7.35 (d, 2 H), 7.40 (s, 1 H), 7.80 (d, 1 H), 7.90 (d, 2 H).

LRMS (Thermospray): 578.0 (MNH$_4$$^+$).

EXAMPLE 59

3-[3-{1-(1,3-Benzodioxol-5yl)-2-[(4-isopropylphenyl)sulfonamido]-2-oxoethyl}-1-methyl-1H-6-indolyl]propanoic acid

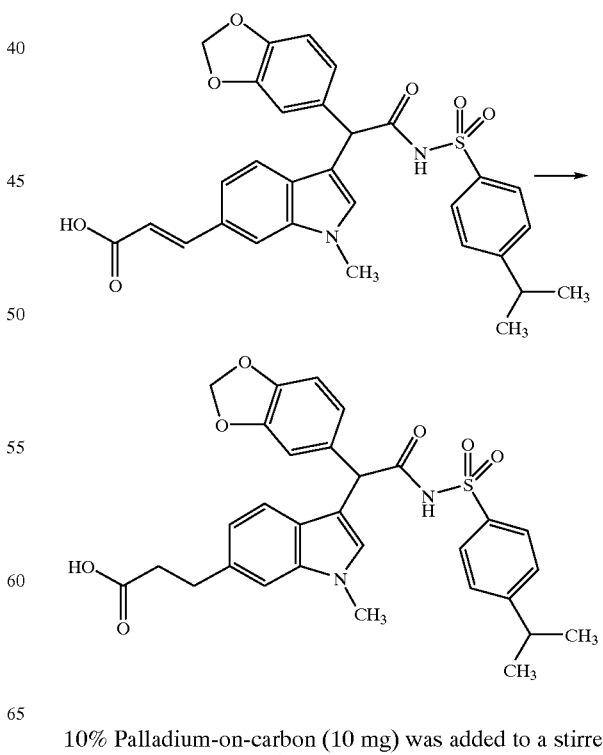

10% Palladium-on-carbon (10 mg) was added to a stirred solution of (E)-3-[3-{1-(1,3-benzodioxol-5-yl)-2-[(4- isopropylphenyl)sulfonamido]-2-oxoethyl}-1-methyl-1H-6-indolyl]-2-propenoic acid (the compound of Example 58, 80 mg, 0.14 mmol) and ammonium formate (64 mg, 0.5 mmol) in a 1:1 mixture of tetrahydrofuran and ethanol (10 ml total). The mixture was stirred at reflux for 48 h, cooled, filtered through Arbocel™ and concentrated. The grey foam was purified by flash column chromatography (elution with 98% dichloromethane/2% methanol) giving the product as a white foam.

$^1$H NMR (300 MHz, CDCl$_3$): δ=1.25 (d, 6 H), 2.70 (t, 2 H), 3.00 (m, 3 H), 3.60 (s, 3 H), 4.95 (s, 1 H), 5.90 (s, 2 H), 6.60 (m, 4 H), 6.80 (d, 1 H), 7.00 (d, 1 H), 7.10 (s, 1 H), 7.40 (d, 2 H), 7.80 (d, 2 H), 8.20 (brs, 1 H).

LRMS (Thermospray): 563.6 (MH$^-$).

EXAMPLE 60
3-{1-(1,3-Benzodioxol-5-yl)-2-[(4-isopropylphenyl)sulfonamido]-2-oxoethyl}-1-methyl-6-(4H-1,2,4-triazol-3-yl)-1H-indole

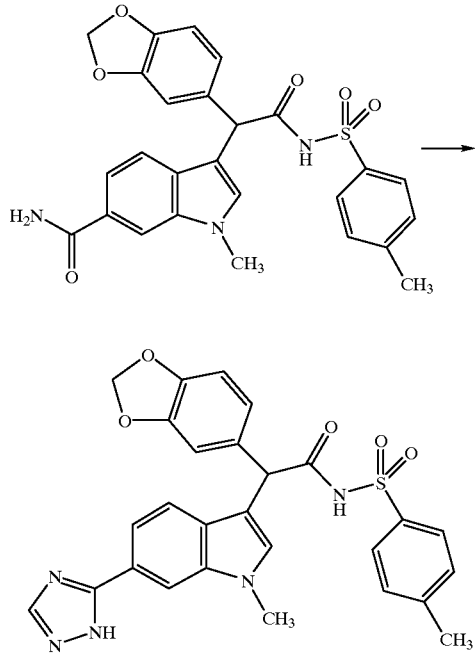

Dimethylformamide dimethylacetal (10 ml) was added to 3-{1-(1,3-benzodioxol-5-yl)-2-[(4-isopropylphenyl)sulfonamido]-2-oxoethyl}-1-methyl-1H-6-indolecarboxamide (the compound of Example 28, 180 mg, 0.36 mmol) and the slurry was heated at reflux for 48 h. The solvent was removed in vacuo and the residue redissolved in glacial acetic acid (8 ml). Hydrazine hydrate (12 mg, 4.68 mmol) was added and the solution heated at reflux for 24 h. After cooling the crude product was extracted from brine (50 ml) with ethyl acetate (2×50 ml). The organic layers were dried (MgSO$_4$) and concentrated. Flash column chromatography (elution with 96% dichloromethane/4% methanol) gave the desired product as a pale yellow solid.

$^1$H NMR (300 MHz, CDCl$_3$): δ=2.40 (s, 3 H), 2.55 (s, 3 H), 5.00 (s, 1 H), 5.80 (s, 2 H), 5.90 (brs, 1 H), 6.60 (s, 3 H), 6.80 (s, 1 H), 7.00 (d, 1 H), 7.20 (d, 2 H), 7.45 (d, 1 H), 7.80 (d, 2 H), 7.90 (s, 1 H), 8.20 (s, 1 H).

LRMS (APCI): 530.0 (MH$^-$).

EXAMPLE 61
2-(1,3-Benzodioxol-5-yl)-2-[1-methyl-6-(triisopropylsilyloxymethyl)-1H-3-indolyl]acetic acid (a) 6-Hydroxymethyl-1-methylindole

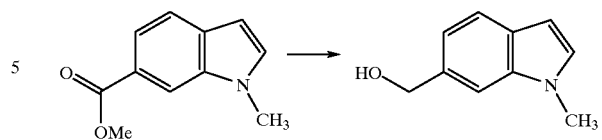

To a solution of 6-methoxycarbonyl-1-methylindole (prepared by the method of Example 1(b), but using 6-bromo-1-methylindole in place of 6-bromo-1-ethylindole, 5 g) in tetrahydrofuran (30 ml) at −70° C. under a nitrogen atmosphere, was added diisobutyl aluminium hydride (66 ml of a 1.0 M solution in tetrahydrofuran) dropwise with stirring. The solution was stirred at −70° C. for 15 mins then warmed to room temperature for 2 hours. The mixture was diluted with water (100 ml) and partitioned between ethyl acetate and aqueous sodium hydroxide. The aqueous layer was re-extracted with ethyl acetate and combined organic extracts were dried (MgSO$_4$) and evaporated to give crude product which was purified by flash column chromatography using 80% ethyl acetate/20% hexane eluant to give the subtitle compound as a clear oil which solidified on standing (4.1 g).

$^1$H NMR (400 MHz, CDCl$_3$): δ=1.60 (s, 1 H), 3.80 (s, 3 H), 4.80 (d, 2 H), 6.45 (s, 1 H), 7.00 (s, 1 H), 7.05 (d, 1 H), 7.35 (s, 1 H), 7.60 (d, 1 H).

LRMS (Thermospray): 162.3 (MH$^+$)

(b) Methyl 2-(1,3-benzodioxol-5-yl)-2-hydroxyacetate

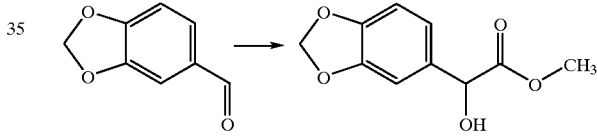

Lithium chloride (11.8 g), potassium hydroxide (31.4 g) and tetrabutylammonium bromide (4.5 g) were dissolved in a mixture of 1,4-dioxane (120 ml) and water (120 ml). Piperonal (21 g, 140 mmol) was added to this vigorously stirred ice-cold mixture, and after 10 minutes bromoform (12.2 ml 140 mmol) was added dropwise over ~30 minutes. Stirring was continued for 20 hours at ambient temperature. Water (500 ml) was added and the mixture warmed to dissolve the precipitate. After washing with diethylether, the aqueous solution was acidified with concentrated hydrochloric acid. The crude carboxylic acid intermediate was isolated by extraction with diethylether and evaporation in vacuo. The residue was dissolved in methanol (500 ml) and acidified with 20 drops of concentrated sulphuric acid. The solution was heated to reflux for 2 hours, then cooled and evaporated in vacuo. The residue was dissolved in diethylether and washed with water. The organic fraction was dried (magnesium sulphate), and concentrated in vacuo. Flash chromatography using dichloromethane as eluant, and then recrystallisation from diisopropylether gave 13.2 g of the subtitle compound, (m.p. 93–95° C.)

$^1$H NMR (300 MHz, CDCl$_3$): δ=3.35 (d, 1 H exchangeable), 3.77 (s, 3 H), 5.07 (d, 1 H), 5.95 (s, 2 H), 6.80 (d, 1 H), 6.90 (s, 1 H), 6.92 (d, 1 H).

LRMS (Thermospray): 228.5 (MNH$_4^+$)

(c) Methyl 2-(1,3-benzodioxol-5-yl)-2-bromoacetate

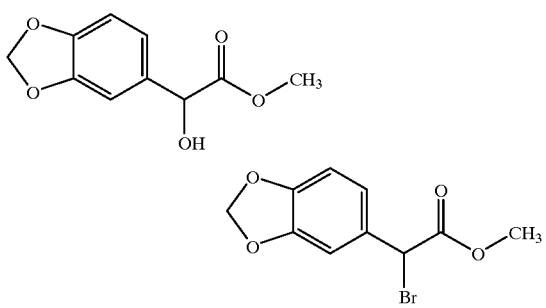

Hydrobromic acid (20 ml of 62% w/v solution in water) was added to methyl 2-(1,3-benzodioxol-5-yl)-2-hydroxyacetate (from step (b), 11 g, 52 mmol) in toluene (200 ml). After stirring for 3 hours the aqueous layer was removed and the organic layer was evaporated in vacuo. The residue was flash chromatographed, eluting with dichloromethane, and then crystallised with diisopropylether and hexane.

$^1$H NMR (300 MHz, CDCl$_3$): δ=3.76 (s, 3 H), 5.26 (s, 1 H), 5.95 (s, 2 H), 6.70 (d, 1 H), 6.92 (d, 1 H), 7.09 (s, 1 H). m.p.: 39–41° C.

(d) Methyl 2-(1,3-benzodioxol-5-yl)-2-[6-(hydroxymethyl)-1-methyl-1H-3-indolyl]acetate

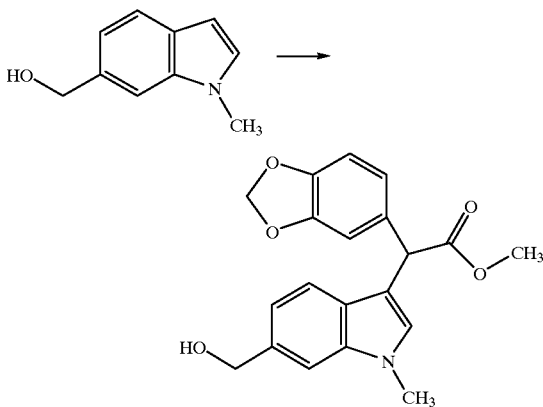

2,6-Dimethylpyridine (0.12 ml) was added to a stirred solution of methyl 2-(1,3-benzodioxol-5-yl)-2-bromoacetate (from step (c). 273 mg, 1 mmol) and 6-(hydroxymethyl)-1-methylindole (from step (a), 161 mg, 1 mmol) in anhydrous dimethylformamide (2 ml) at ambient temperature, under a nitrogen atmosphere. The solution was heated to 80° C. for 3 hours. The reaction mixture was cooled, and partitioned between diethylether and water, separated and the organic layer dried (magnesium sulphate) and evaporated in vacuo. The residue was flash chromatographed (using diethyl ether as eluant) to give the subtitle compound as a colourless foam (273 mg).

$^1$H NMR (300 MHz, CDCl$_3$): δ=1.64 (t, 1H exchangeable), 3.72 (s, 3 H), 3.76 (s, 1 H), 4.79 (d, 2 H), 5.16 (s, 1 H), 5.90 (s, 2 H), 6.73 (d, 1 H), 6.85 (d, 1 H), 6.90 (s, 1 H), 7.03 (d, 1 H), 7.08 (s, 1 H), 7.31 (s, 1 H), 7.40 (d, 1 H).

LRMS (Thermospray): 353.9 (MH$^-$)

(e) Methyl 2-(1,3-benzodioxol-5-yl)-2-[1-methyl-6-(triisopropylsilyloxymethyl)-1H-3-indolyl]acetate

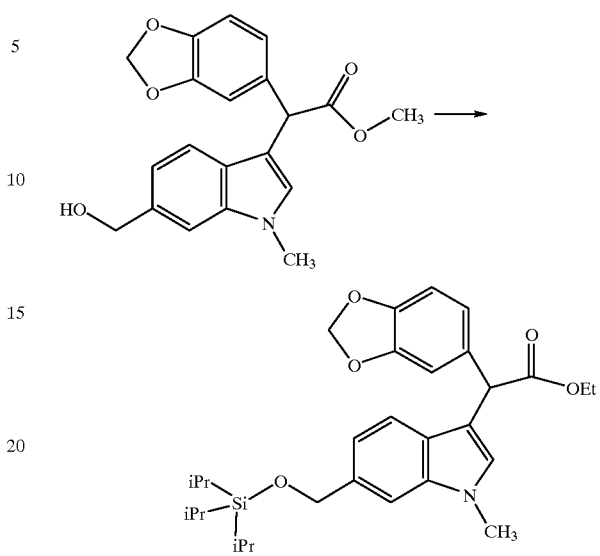

Chlorotriisopropylsilane (0.19 ml, 0.88 mmol) was added to a solution of methyl 2-(1,3-benzodioxol-5-yl)-2-[6-(hydroxymethyl)-1-methyl-1H-3-indolyl]acetate (from step (d), 260 mg, 0.74 mmol) and imidazole (100 mg, 1.47 mmol) in anhydrous dimethylformamide (3 ml). After 3 hours the mixture was partitioned between diethyl ether and water, the organic layer was separated and washed with water. The organic layer was dried (magnesium sulphate), and the solvent removed in vacuo. The residue was flash chromatographed (using 50% dichloromethane, 50% hexane as eluent) to give the subtitle compound (305 mg) as an oil.

$^1$H NMR (300 MHz, CDCl$_3$): δ=1.00–1.20 (m, 21 H), 3.74 (s, 3 H), 3.75 (s, 3 H), 4.95 (s, 2 H), 5.15 (s, 1 H), 5.90 (d, 2 H), 6.72 (d, 1 H), 6.88 (d, 1 H), 6.91 (s, 1 H), 7.00 (d, 1 H), 7.03 (s, 1 H), 7.34 (s, 1 H), 7.36 (d, 1 H).

LRMS (Thermospray): 510.4 (MH$^-$).

(f) 2-(1,3-Benzodioxol-5-yl)-2-[1-methyl-6-(triisopropylsilyloxymethyl)-1H-3-indolyl]acetic acid

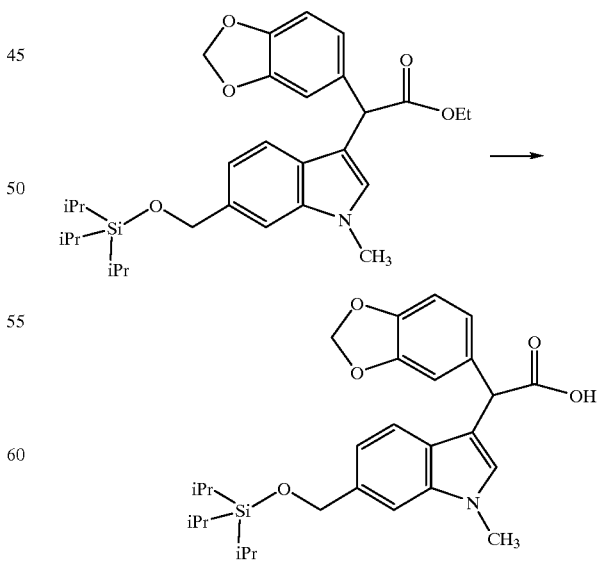

The subtitle compound was prepared by the method of Example 2 from the compound of step (e).

¹H NMR (300 MHz, CDCl₃): δ=1.03–1.22 (m, 21 H), 3.72, (s, 3 H), 4.96 (s, 2 H), 5.18 (s, 1 H), 5.91 (s, 2 H), 6.72 (d, 1 H), 6.88 (d, 1 H), 6.90 (s, 1 H), 7.00 (d, 1 H), 7.06 (s, 1 H), 7.36 (s, 1 H), 7.37 (d, 1 H).

LRMS (Thermospray): 497.1 (MH⁺)

(g) 3-{1-(1,3-Benzodioxol-5-yl)-2-[2-ethyl-4-methylphenyl)sulfonamido]-2-oxoethyl}-6-(triisopropylsilyloxymethyl)-1-methyl-1H-indole

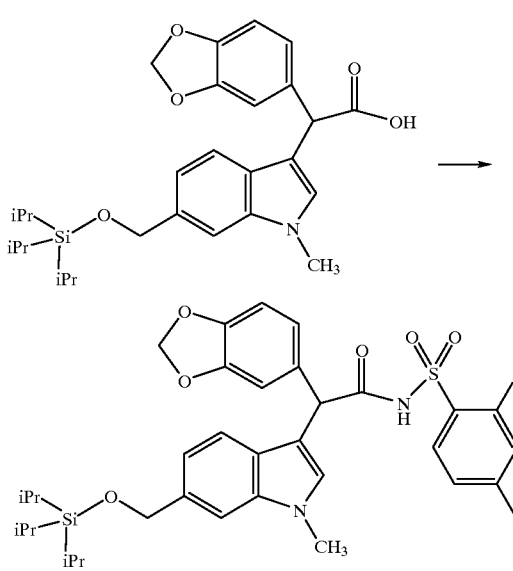

1-(3-Dimethylaminopropyl)-3-ethylcarbodiimide hydrochloride (113 mg, 0.59 mmol) was added to a stirred solution of 2-(1,3-benzodioxol-5-yl)-2-[6-(triisopropylsilyloxymethyl)-1-methyl-1H-3-indolyl]acetic acid (from step (f), 250 mg, 0.49 mmol), N,N-dimethylaminopyridine (78 mg, 0.64 mmol) and the sulphonamide from Preparation 1 (107 mg, 0.54 mmol) in dichloromethane (6 ml) at room temperature under a nitrogen atmosphere. After 12 h the reaction mixture was poured into 1N hydrochloric acid (50 ml) and extracted with dichloromethane (2×50 ml). The organic fractions were dried (MgSO₄) and concentrated to give a yellow foam. Flash column chromatography (elution with 98% dichloromethane/2% methanol) gave the subtitle (95 mg) as a white foam.

¹H NMR (400 MHz, CDCl₃): δ=1.00 (t, 3 H), 1.10 (d, 18 H), 1.15 (m, 3 H), 2.35 (s, 3 H), 2.50 (q, 2 H), 3.60 (s, 3 H), 4.90 (s, 2 H), 4.95 (s, 1 H), 5.80 (s, 2 H), 6.65 (m, 3 H), 6.70 (s, 1 H), 6.90 (d, 1 H), 7.05 (s, 1 H), 7.10 (m, 2 H), 7.35 (s, 1 H), 8.00 (d, 1 H).

LRMS (Thermospray): 677.4 (MH⁻).

(h) 3-{1-(1,3-Benzodioxol-5-yl)-2-[2-ethyl-4-methylphenyl)sulfonamido]-2-oxoethyl}-6-(hydroxymethyl)-1-methyl-1H-indole

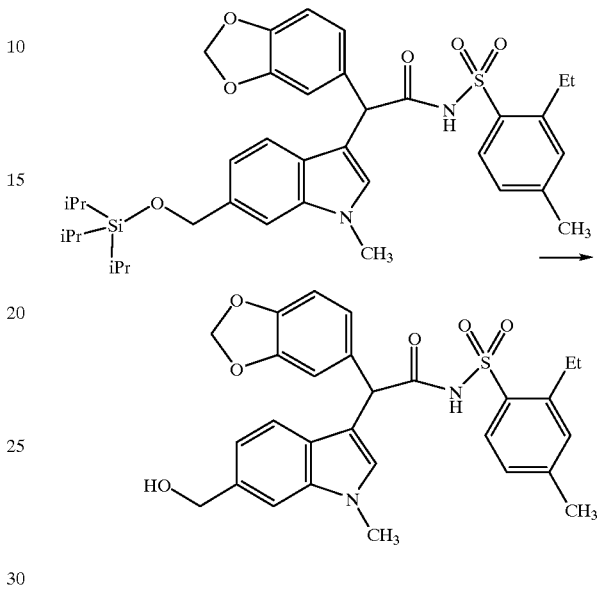

Tetraethylammonium fluoride (312 mg, 2.18 mmol) was added to a stirred solution of the compound of step (g) (380 mg, 0.55 mmol) in acetonitrile (6 ml) at room temperature under a nitrogen atmosphere. After 12 h the mixture was poured into 1M hydrochloric acid (50 ml) and extracted into ethyl acetate (2×50 ml). The organic fractions were combined, dried (MgSO₄) and concentrated in vacuo to give a yellow foam. Flash column chromatography (eluting with 98% dichloromethane/2% methanol) gave the product as a white solid (242 mg).

¹H NMR (400 MHz, CDCl₃): δ=1.15 (t, 2 H), 2.30 (s, 3 H), 2.60 (q, 2 H), 3.60 (s, 3 H), 4.75 (s, 2 H), 5.25 (s, 1 H), 5.80 (s, 2 H), 6.60 (m, 3 H), 6.80 (s, 1 H), 6.95 (d, 1 H), 7.05 (s, 1 H), 7.10 (d, 2 H), 7.20 (s, 1 H), 8.00 (d, 1 H).

LRMS (Thermospray): 538.2 (MNH₄⁺).

Examples 62–64 were prepared by the methods of Example 61, but using the appropriate sulphonamide in the penultimate step.

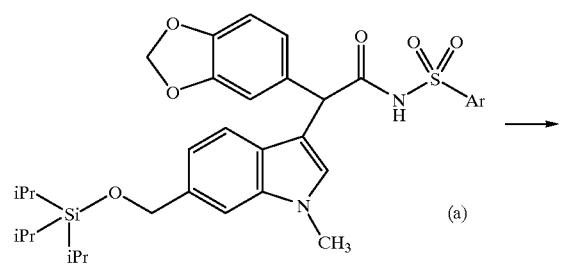

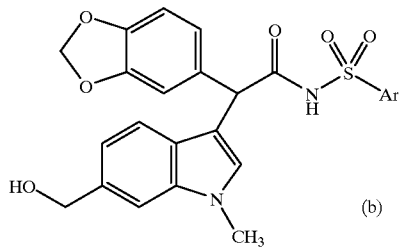

(b)

| Example N° | Ar | Physical Data |
|---|---|---|
| 62(a)* | 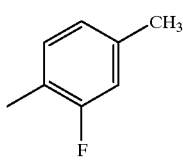 | $^1$H NMR(300MHz, CDCl$_3$): δ=1.05(d, 18H), 1.20 (m, 3H), 2.40(s, 3H), 3.75(s, 3H), 4.95(s, 3H), 5.95 (s, 2H), 6.70(d, 2H), 6.75(s, 1H), 6.80(s, 1H), 6.90 (d, 1H), 7.00(d, 1H), 7.10(d, 1H), 7.20(d, 1H), 7.40 (s, 1H), 7.90(t, 1H), 8.25(s, 1H). LRMS(APCI): 668.0(MH$^+$). |
| 62(b) | " | $^1$H NMR(400MHz, d$_6$-DMSO): δ=2.30(s, 3H), 3.60 (s, 3H), 4.50(s, 2H), 5.00(brs, 1H), 5.10(s, 1H), 5.90 (s, 2H), 6.60(s, 1H), 6.65(d, 1H), 6.80(d, 1H), 6.85 (s, 1H), 6.90(d, 1H), 7.10(d, 1H), 7.15(d, 1H), 7.20 (d, 1H), 7.25(s, 1H), 7.50(s, 1H), 7.70(t, 1H), 12.50 (s, 1H). LRMS(Thermospray): 511.2(MH$^+$). |
| 63(a) | 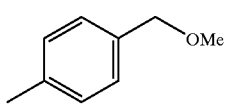 | $^1$H NMR(400MHz, CDCl$_3$): δ=1.10(d, 18H), 1.15 (m, 3H), 3.40(s, 3H), 3.65(s, 3H), 4.45(s, 2H), 4.90 (s, 3H), 5.90(s, 2H), 6.60(m, 3H), 6.90(d, 1H), 7.00 (d, 1H), 7.30(s, 1H), 7.40(d, 2H), 7.85(d, 2H), 8.05 (s, 1H). LRMS(APCI): 681.6(MH$^+$). |
| 63(b) | " | $^1$H NMR(400MHz, d$_6$-DMSO): δ=3.25(s, 3H), 3.60 (s, 3H), 4.45(s, 2H), 4.50(m, 2H), 5.00(brs, 1H), 5.05 (s, 1H), 5.80(s, 2H), 6.60(s, 1H), 6.65(d, 1H), 6.75 (d, 2H), 6.85(d, 1H), 7.00(d, 1H), 7.25(s, 1H), 7.40 (d, 2H), 7.80(d, 2H), 12.4(brs, 1H), LRMS(Thermospray): 523.4(MH$^+$). |
| 64(a) | 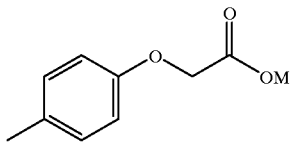 | $^1$H NMR(400MHz, CDCl$_3$): δ=1.05(d, 18H), 1.20 (m, 3H), 3.60(s, 3H), 3.80(s, 3H), 4.60(s, 2H), 4.90 (s, 3H), 5.85(s, 2H), 6.60(m, 4H), 6.90(d, 3H), 7.00 (d, 1H), 7.35(s, 1H), 7.80(d, 2H), 8.10(brs, 1H) LRMS(APCI): 723.0(MH$^+$). |
| 64(b) | " | $^1$H NMR(400MHz, CDCl$_3$): δ 2.00(brs, 1H), 3.60 (s, 3H), 3.75(s, 3H), 4.60(s, 2H), 4.70(s, 2H), 5.00(s, 1H), 5.80(s, 2H), 6.60(d, 1H), 6.70(d, 1H), 6.75(s, 1H), 6.80(s, 1H), 6.85(d, 2H), 6.90(d, 1H), 7.10(d, 1H), 7.20(s, 1H), 7.80(d, 2H), LRMS(APCI): 567(MH$^+$). |

*See Preparation 2 for sulphonamide preparation

EXAMPLE 65

3-{1-(1,3-Benzodioxol-5-yl)-2-[(2-methoxy-4-methylphenyl)sulfonamido]-2-oxoethyl}-6-(hydroxymethyl)-1-methyl-1H-indole (a) 3-{1-(1,3-Benzodioxol-5-yl)-2-[(2-methoxy-4-methylphenyl)sulfonamido]-2-oxoethyl}-6-(methoxycarbonyl)-1-methyl-1H-indole The subtitle compound was prepared using the methods of Examples 1(b), 1(d), 2 and 3, but starting with 6-bromo-1-methylindole in place of 6-bromo-1-ethylindole, and reacting with the sulphonamide of Preparation 11 in the method of Example 3.

(b) 3-{1-(1,3-Benzodioxol-5-yl)-2-[(2-methoxy-4-methylphenyl)sulfonamido]-2-oxoethyl}-6-(hydroxymethyl)-1-methyl-1H-indole

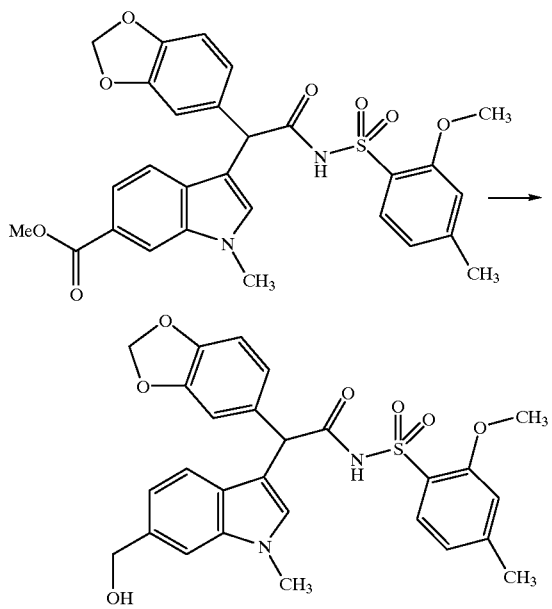

Lithium aluminium hydride (15 mg, 0.2 mmol) was added slowly to a stirred solution of methyl 3-{1-(1,3-benzodioxol-5-yl)-2-[(2-methoxy-4-methylphenyl)sulfonamido]-2-oxo-ethyl}-1-methyl-1H-6-indolecarboxylate (from step (a), 220 mg, 0.4 mmol) in tetrahydrofuran at 0° C. under a nitrogen atmosphere. After 2 h a further 1 equivalent (30 mg) of lithium aluminium hydride was added and the mixture was warmed to room temperature. After 1 h ethyl acetate (10 ml) was carefully added and the product extracted from 1 N hydrochloric acid with ethyl acetate (2×50 ml). The combined organic layers were dried (MgSO$_4$) and concentrated in vacuo. Purification by flash column chromatography (elution with 95% dichloromethane/5% methanol) gave the product as a white solid (130 mg).

$^1$H NMR (400 MHz, CD$_3$OD): δ=2.45 (s, 3 H), 3.55 (s, 3 H), 3.75 (s, 3 H), 4.75 (s, 2 H), 5.15 (s, 1 H), 5.95 (d, 2 H), 6.70 (s, 1 H), 6.75 (m, 3 H), 6.85 (s, 1 H), 6.95 (d, 1 H), 7.00 (d, 1H), 7.25 (d, 1 H), 7.35 (s, 1 H), 7.85 (d, 1 H).

LRMS (Thermospray): 523.7 (MH$^+$).

Analysis: Found: C, 61.00; H, 5.12; N, 5.19. C$_{27}$H$_{26}$N$_2$O$_7$S.0.5H$_2$O; Requires: C, 61.00; H, 5.12; N, 5.7. m.p.=184–186° C.

The title compound was separated into its individual enantiomers using a Chiralpak™ AD column (25×2 cm) with a flow rate of 10 ml/min using a 70:30 mix of hexane:isopropylalcohol with 0.6% trifluoroacetic acid and 0.4% diethylamine added. The products were detected at 220 nm and had retention times of 32 min and 39 min.

The enantiomeric purity was checked by chromatographing 100 μl of the eluent from the above separation, using a Chiralpak™ AD column (25×0.46 cm), a flow rate of 1 ml/min and a 70:30 mix of hexane:iso-propylalcohol with 0.3% trifluoroacetic acid and 0.2% diethylamine added as eluant. The products were detected at 220 nm and had retention times of 15.5 min and 18 min.

Examples 66 and 67 were prepared by the method of Example 65, but using the sulphonamides of Preparations 10 and 9 respectively.

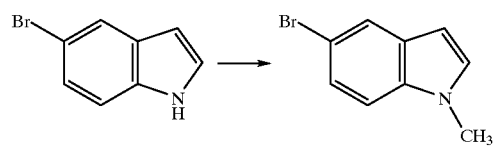

| Example N° | Ar | Physical Data |
|---|---|---|
| 66 | ![Ar group with CH3, CH3, O-CH2CH2-OMe] | $^1$H NMR(300MHz CDCl$_3$); 2.40 (s, 3H), 3.25(s, 3H), 3.40–4.00 (m, 2H), 3.70(s, 3H) 4.80(d, 2H), 5.05(s, 1H), 5.90(s, 2H), 5.60–7.40(m, 9H), 7.90(d, 2H), 9.00(s, 1H). LRMS(Thermospray): 567.1(MH$^-$) |
| 67 | ![Ar group with CH3, CH3, OEt] | $^1$H NMR(400MHz d$_6$-DMSO): 1.10(t, 3H), 2.30(d, 2H)3.60(s, 3H), 3.70–3.90(m, 2H), 4.50 (d, 2H), 5.00(t, 1H), 5.15(s, 1H), 5.90(d, 2H), 6.60–7.65(m, 10H), 12.05(s, 0.5H), 12.30(s, 0.5H). LRMS(Thermospray): 537.4 (MH$^-$) |

EXAMPLE 68

2-(1,3-Benzodioxol-5-yl)-2-(5-bromo-1-methyl-1H-3-indolyl)acetic acid (a) 5-Bromo-1-methylindole Sodium hydride (440 mg of a 60% dispersion in paraffin wax) was added to a stirred solution of 5-bromoindole (1.96 g, 10 mmol) in dimethylformamide (20 ml) at ambient temperature under a nitrogen atmosphere. After 30 minutes methyl p-toluenesulphonate (2.05 g 11 mmol) was added. After 20 hours the mixture was partitioned between diethyl ether and water. The organic layer was separated and washed twice with water. The organic layer was dried (magnesium sulphate) and the solvent was removed in vacuo. The residue was purified by flash column chromatography (using 50% hexane, 50% dichloromethane as eluant) to give 2.07 g of product as a waxy solid.

$^1$H NMR (300 MHz, CDCl$_3$): δ=3.75 (s, 3 H), 6.42 (d, 1 H), 7.05 (d, 1 H), 7.17 (d, 1 H), 7.28 (d, 1 H), 7.75 (s, 1 H).

LRMS (Thermospray): 212 (MH$^+$)

(b) Methyl 2-(1,3-benzodioxol-5-yl)-2-(5-bromo-1-methyl-1H-3-indolyl)acetate

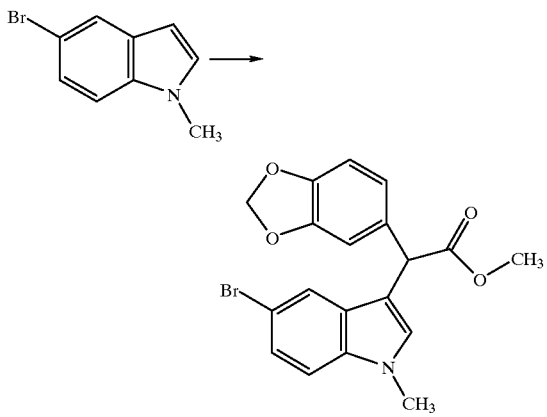

2,6-Dimethylpyridine (0.75 ml) was added to a stirred solution of methyl 2-(1,3-benzodioxol-5-yl)-2-bromoacetate (from Example 61(c), 1.75 g, 6.43 mmol) and 5-bromo-1-methylindole (from step (a), 1.35 g) in anhydrous dimethylformamide (10 ml) at ambient temperature, under a nitrogen atmosphere. The solution was heated to 80° C. for 8 hours. The reaction mixture was partitioned between diethylether and water, separated and the organic layer dried (magnesium sulphate) and evaporated in vacuo. The residue was flash chromatographed (using 50% dichloromethane and 50% hexane as eluant) to give the subtitle compound as a colourless oil (1.98 g).

$^1$H NMR (300 MHz, CDCl$_3$): δ=3.72 (s, 3 H), 3.74 (s, 3 H), 5.09 (s, 1 H), 5.92 (s, 2 H), 6.75 (d, 1 H), 6.85 (d, 1 H), 6.88(s, 1 H), 7.10 (s, 1 H), 7.15 (d, 1 H), 7.28 (d, 1 H), 7.55 (s, 1 H).

LRMS (Thermospray): 402.0, 404.0 (MH$^-$).

(c) 2-(1,3-Benzodioxol-5-yl)-2-(5-bromo-1-methyl-1H-3-indolyl)acetic acid

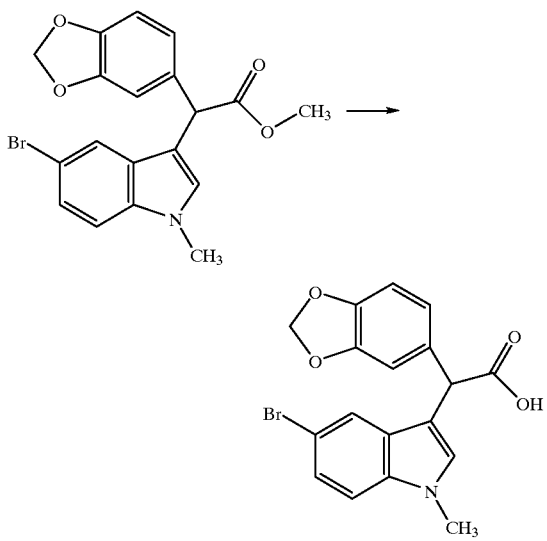

Aqueous sodium hydroxide (14.7 ml of 1M) was added to a solution of methyl 2-(1,3-benzodioxol-5-yl)-2-(5-bromo-1-methyl-1H-3-indolyl)acetate from (b) (1.97 g, 4.9 mmol) in a 3:1 mixture of methanol and 1,4-dioxane at ambient temperature. The mixture was heated to reflux for 1 hour before recooling and removing the organic solvents in vacuo. The residue was redissolved in water and acidified with drops of concentrated hydrochloric acid. The resultant precipitate was extracted with diethylether, dried (magnesium sulphate) and the solvent removed in vacuo. The residue was crystallised from diisopropylether to give the subtitle compound (1.59 g).

$^1$H NMR (300 MHz, CDCl$_3$): δ=3.74 (s, 3 H), 5.09 (s, 1 H), 5.92 (s, 2 H), 6.75 (d, 1 H), 6.85 (d, 1 H), 6.88 (s, 1 H), 7.10 (s, 1 H), 7.15 (d, 1 H), 7.28 (d, 1 H), 7.55 (s, 1 H).

LRMS (Thermospray): 388.4, 390.4 (MH$^+$)

Analysis: Found C, 55.61; H, 3.66; N, 3.51. C$_{18}$H$_{14}$BrNO$_4$ requires: C, 55.69; H, 3.64; N, 3.60. m.p.: 191–193° C.

Examples 69–78 were prepared by the method of Example 68, starting with the appropriately substituted indole.

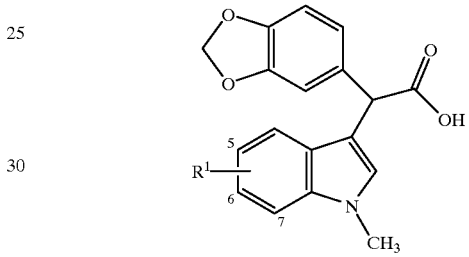

| Example | R$^1$= | Data |
|---|---|---|
| 69 | 5-F (C$_{18}$H$_{14}$FNO$_4$) | $^1$H NMR(300MHz, CDCl$_3$): δ=3.75(s, 3H), 5.10(s, 1H), 5.92(s, 2H), 6.74(d, 1H), 6.83–7.00(m, 3H), 7.06(d, 1H), 7.15(s, 1H), 7.18(m, 1H) LRMS(Thermospray): 328.2(MH$^-$) |
| 70 | 5-NC (C$_{19}$H$_{14}$N$_2$O$_4$) | $^1$H NMR(300MHz, CDCl$_3$): δ=3.80(s, 3H), 5.15(s, 1H), 5.94(s, 2H), 6.76(d, 1H), 6.84 (s, 1H), 6.85(d, 1H), 7.26(s, 1H), 7.32(d, 1H), 7.42(d, 1H), 7.75(s, 1H). LRMS(Thermospray): 352.3(MH$^+$) |
| 71 | 5-CH$_3$O (C$_{19}$H$_{17}$NO$_5$) | $^1$H NMR(300MHz, CDCl$_3$): δ=3.72(s, 3H), 3.78(s, 3H), 5.13(s, 1H), 5.92(s, 2H), 6.77 (d, 1H), 6.86(m, 2H), 6.92(s, 1H), 7.06(s, 1H), 7.16–7.27(m, 2H). LRMS(Thermospray): 340.4(MH$^+$) |
| 72 | 6-F (C$_{18}$H$_{14}$FNO$_4$) | $^1$H NMR(300MHz, CDCl$_3$): δ=3.70(s, 3H), 5.13(s, 1H), 5.92(s, 2H), 6.70–6.98(m, 5H), 7.06(s, 1H), 7.33(m, 1H). LRMS(Thermospray): 327.8(MH$^+$) m.p.: 150–152° C. |
| 73 | 6-Cl (C$_{18}$H$_{14}$ClNO$_4$) | $^1$H NMR(300MHz, d$_6$-DMSO): δ=3.75(s, 3H), 5.08(s, 1H), 5.95(s, 2H), 6.80–6.90(m, 3H), 6.97(d, 1H), 7.27(s, 1H), 7.40(d, 1H), 7.50(s, 1H), 12.50(br, 1H exchangeable). LRMS(Thermospray): 343.9(MH$^+$) |
| 74 | 6-Br (C$_{18}$H$_{14}$BrNO$_4$) | $^1$H NMR(400MHz, d$_6$-DMSO): δ=3.71(s, 3H), 5.03(s, 1H), 5.90(d, 2H), 6.75–6.82(m, 2H), 6.84(s, 1H), 7.06(d, 1H), 7.22(s, 1H), 7.32(d, 1H), 7.61(s, 1H), 12.60(br, 1H exchangeable). Analysis: Found: C, 55.50: H, 3.60: N, 3.54, C$_{18}$H$_{14}$BrNO$_4$ Requires: C, 55.69: H, 3.64: N, 3.60. |
| 75 | 7-F (C$_{18}$H$_{14}$FNO$_4$) | $^1$H NMR(400MHz, CDCl$_3$): δ=3.93(s, 3H), 5.10(s, 1H), 5.90(s, 2H), 6.72(d, 1H), 6.80–6.93(m, 4H), 7.02(s, 1H), 7.11(d, 1H). LRMS(Thermospray): 328.2(MH$^+$) |

-continued

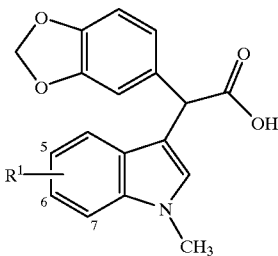

| Example | R¹= | Data |
|---|---|---|
| 76 | 7-Cl ($C_{18}H_{14}ClNO_4$) | ¹H NMR(400MHz, CDCl₃): δ=4.09(s, 3H), 5.10(s, 1H), 5.90(s, 2H), 6.72(d, 1H), 6.82 (d, 1H), 6.83(s, 1H), 6.88(t, 1H), 7.01(s, 1H), 7.10(s, 1H), 7.28(d, 1H). LRMS(Thermospray): 344.2(MH⁺) m.p.: 146–147° C. |
| 77 | 7-Br ($C_{18}H_{14}BrNO_4$) | ¹H NMR(300MHz, CDCl₃): δ=4.10(s, 3H), 5.10(s, 1H), 5.90(s, 2H), 6.71(d, 1H), 6.80–6.86(m, 3H), 7.03(s, 1H), 7.29–7.34(m, 2H). LRMS(Thermospray): 388.1(MH⁺) m.p.: 151° C. |
| 78 | 6-CN ($C_{19}H_{14}N_2O_4$) | ¹H NMR(400MHz, CDCl₃): δ=3.80(s, 3H), 5.15(s, 1H), 5.80(s, 2H), 6.75(d, 1H), 6.85 (m, 1H), 7.25(m, 2H), 7.40(d, 1H), 7.60(s, 1H). LRMS(Thermospray): (MH⁺). |

EXAMPLE 79
3-{1-(1,3-Benzodioxol-5-yl)-2-[(2-methoxy-4-methylphenyl)sulfonamido]-2-oxoethyl}-5-bromo-1-methyl-1H-indole

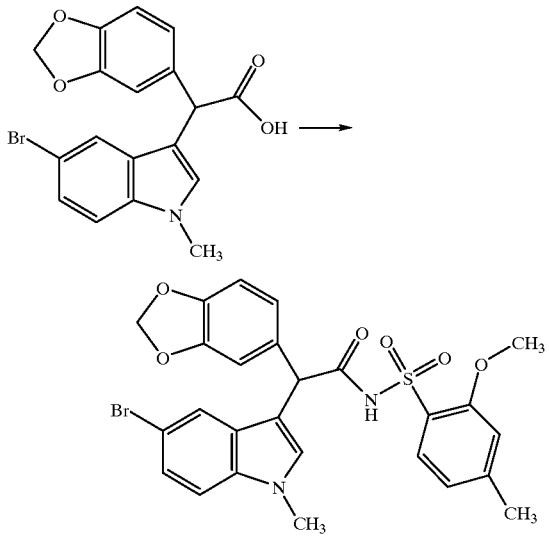

4-Dimethylaminopyridine (151 mg) was added to a solution of 2-(1,3-benzodioxol-5-yl)-2-(5-bromo-1-methyl-1H-3-indolyl)acetic acid (the product of Example 68, 480 mg, 1.24 mmol) in anhydrous dichloromethane (10 ml) at ambient temperature. 2-Methoxy-4-methyl-1-benzenesulfonamide (from Preparation 11, 300 mg, 1.48 mmol) was added to the solution, followed by 1-(3-dimethylaminopropyl)-3-ethylcarbodiimide hydrochloride (355 mg, 1.85 mmol), and stirring was continued for 20 hours. The solution was washed twice with 2N hydrochloric acid, and dried (magnesium sulphate) and the solvents removed in vacuo. The residue was flash chromatographed using 1% methanol in dichloromethane as eluant, and crystallised from dichloromethane and diethyl ether mixture to give the subtitle compound (535 mg).

¹H NMR (400 MHz, d₆-DMSO): δ=2.30 (s, 3 H), 3.55 (s, 3 H), 3.64 (s, 3 H), 5.10 (s, 1 H), 5.90 (d, 2 H), 6.63 (d, 1 H), 6.66 (s, 1 H), 6.72–7.00 (m, 4 H), 7.19 (d, 1 H), 7.32 (d, 1 H), 7.34 (s, 1 H), 7.62 (d, 1 H), 11.70 (s, 1 H exchangeable).

LRMS (Thermospray): 588.2 (MNH₄⁺) Analysis: Found C, 53.79; H, 4.29; N, 4.62. $C_{26}H_{23}BrN_2O_6S$; 0.5 H₂O requires: C, 53.80; H, 4.17; N, 4.83.

m.p.: 145–150° C.

Examples 80–88 were prepared by the method of Example 79 using the carboxylic acids of Examples 69–76 and 78 respectively.

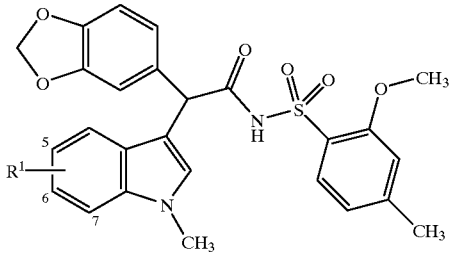

| Example | R¹= | Data |
|---|---|---|
| 80 | 5-F ($C_{26}H_{23}FN_2O_6S$) | ¹H NMR(400MHz, CDCl₃): δ=2.37(s, 3H), 3.45(s, 3H), 3.68(s, 3H), 4.96(s, 1H), 5.88 (s, 2H), 6.60(s, 1H), 6.63–6.69(m, 3H), 6.74–6.96(m, 4H), 7.15(m, 1H), 7.89(d, 1H), 8.50(br, 1H exchangeable). LRMS(Thermospray): 511.4(MH⁺), 528.1(MNH₄⁺) |
| 81 | 5-NC | ¹H NMR(300MHz, CDCl₃): δ=2.42(s, 3H), 3.63(s, 3H), 3.75(s, 3H), 5.03(s, 1H), 5.94(s, 2H), 6.68(s, 1H), 6.70–6.76(m, 3H), 6.90(d, 1H), 7.02(s, 1H), 7.30(d, 1H), 7.42(d, 1H), 7.50(s, 1H), 7.90(d, 1H), 8.38(brs, 1H exchangeable). LRMS(Thermospray): 535.0 (MNH₄⁺) Analysis: Found: C, 61.54; H, 4.75; N, 7.49, $C_{27}H_{23}N_3O_6S$: 0.5 H₂O Requires: C, 61.59; H, 4.59; N, 7.98. |
| 82 | 5-CH₃O | ¹H NMR(300MHz, CDCl₃): δ=2.40(s, 3H), 3.35(s, 3H), 3.62(s, 3H), 3.74(s, 3H), 5.00(s, 1H), 5.92(s, 2H), 6.58(m, 2H), 6.70–6.78(m, 3H), 6.80(s, 1H), 6.82–6.90(m, 2H), 7.20(d, 1H), 7.92(d, 1H), 8.40(brs, 1H exchangeable). LRMS(Thermospray): 523.0(MH⁺) |
| 83 | 6-F ($C_{26}H_{23}FN_2O_6S$) | ¹H NMR(400MHz, CDCl₃): δ=2.37(s, 3H), 3.41(s, 3H), 3.60(s, 3H), 4.96(s, 1H), 5.88(s, 2H), 6.55(s, 1H), 6.62–6.70(m, 4H), 6.81(s, 1H), 6.80–6.90(m, 2H), 7.08(m, 1H), 7.89(d, 1H), 8.80(br, 1H exchangeable). LRMS(Thermospray): 511.4(MH⁺) |
| 84 | 6-Cl ($C_{26}H_{23}ClN_2O_6S$) | ¹H NMR(300MHz, d₆-DMSO): δ=2.35(s, 3H), 3.62(s, 3H), 3.70(s, 3H), 5.18(s, 1H), 5.92(s, 2H), 6.68–6.74(m, 2H), 6.80(d, 1H), 6.87(d, 1H), 6.93–7.00(m, 3H), 7.20(d, 1H), 7.50(s, 1H), 7.67(d, 1H), 12.25 (s, 1H exchangeable). LRMS(Thermospray): 526.9(MH⁺) |
| 85 | 6-Br ($C_{26}H_{23}BrN_2O_6S$) | ¹H NMR(400MHz:, CDCl₃): δ=2.38(s, 3H), 3.40(s, 3H), 3.60(s, 3H), 4.95(s, 1H), 5.88(s, 2H), 6.55(s, 1H), 6.64(m, 3H), 6.82(m, 2H), 7.00(m, 2H), 7.36(s, 1H), 7.87(d, 1H), 8.75 (br, 1H exchangeable). |

-continued

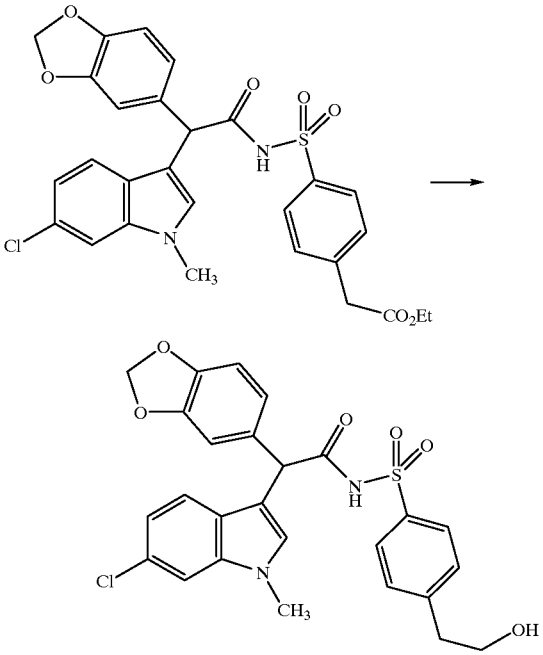

| Example | $R^1=$ | Data |
|---|---|---|
| 86 | 7-F ($C_{26}H_{23}FN_2O_6S$) | LRMS(APCI): 571.8(MH$^+$)<br>Analysis: Found: C, 52.20; H, 3.91; N, 4.62.<br>$C_{26}H_{23}BrN_2O_6S$:0.4$CH_2Cl_2$ requires:<br>C, 52.38; H, 3.96; N, 4.63.<br>m.p.: 145–150° C.(dec.),<br>$^1$H NMR(400MHz, CDCl$_3$): δ=2.38(s, 3H), 3.47(s, 3H), 3.84(s, 3H), 4.98(s, 1H), 5.90(s, 2H), 6.59(s, 1H), 6.67(s, 3H), 6.77(s, 1H), 6.80–6.96(m, 3H), 6.93 (m, 1H), 7.88(d, 1H), 8.50(br, 1H exchangeable),<br>LRMS(Thermospray): 51.2(MH$^+$), 528.1(MNH$_4^+$) m.p.: 123–124° C. |
| 87 | 7-Cl ($C_{27}H_{23}N_3O_6S$) | $^1$H NMR(300MHz. CDCl$_3$): δ=2.38(s, 3H), 3.47(s, 3H), 3.89(s, 3H), 4.98(s, 1H), 5.90(s, 2H), 6.59(s, 1H), 6.66(s, 3H), 6.75(s, 1H), 6.80–6.90(m, 2H), 7.03–7.13(m, 2H), 7.85(d, 1H), 8.40(br, 1H exchangeable).<br>LRMS(APCI): 528.7(MH$^+$)<br>m.p.: 233–234° C. |
| 88 | 6-CN ($C_{27}H_{23}N_3O_6S$) | $^1$H NMR(400MHz, CDCl$_3$): δ=2.40(s, 3H), 3.50(s, 3H), 3.70(s, 3H), 5.00(s, 1H), 5.90(s, 2H), 6.60(d, 1H), 6.65(d, 1H), 6.65(s, 1H), 6.80(d, 1H), 7.10(s, 1H), 7.15(d, 1H), 7.20(s, 1H), 7.25(d, 1H), 7.55(s, 1H), 7.85(d, 1H), 8.70(s, 1H).<br>LRMS(APCI): 517.8(MH$^+$). |

EXAMPLE 89

Ethyl 2-(4-[2-(1,3-benzodioxol-5-yl)-2-(6-chloro-1-methyl-1H-3-indolyl)acetyl]-sulfamoylphenyl)acetate

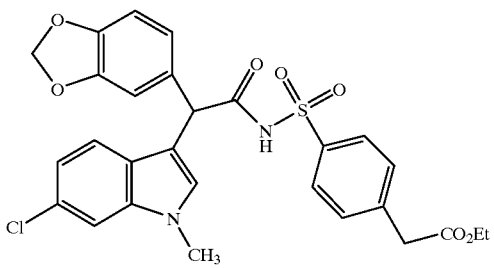

The title compound was prepared by the method of Example 79 from the compound of Example 73 and the appropriate sulphonamide.

$^1$H NMR (400 MHz, CDCl$_3$): δ=1.15 (t, 3 H), 3.60 (s, 3 H), 3.80 (s, 2 H), 4.00 (q, 2 H), 5.00 (s, 1 H), 5.85 (s, 2 H), 6.60 (m, 2 H), 6.75 (d, 1 H), 6.85 (s, 1 H), 6.90 (d, 1 H), 7.05 (d, 1 H), 7.40 (d, 2 H), 7.45 (s, 1 H), 7.80 (d, 2 H).

LRMS (Thermospray): 585.9, 588.6 (MNH$_4^-$).

EXAMPLE 90

3-[1-(1,3-Benzodioxol-5-yl)-2-[4-(2-hydroxyethyl)phenyl]sulfonamido-2-oxoethyl]-6-chloro-1-methyl-1H-indole Lithium aluminium hydride (6 mg, 0.16 mmol) was added to a stirred solution of ethyl 2-(4-[2-(1,3-benzodioxol-5-yl)-2-(6-chloro-1-methyl-1H-3-indolyl)acetyl] sulfamoylphenyl)acetate (the product of Example 89, 80 mg, 0.14 mmol) in tetrahydrofuran (6 ml) at 0° C. under a nitrogen atmosphere. After 40 mins ethyl acetate (1 ml) was slowly added and the reaction mixture was poured into hydrochloric acid (50 ml). The product was extracted into ethyl acetate (2×50 ml), dried (MgSO$_4$) and concentrated. Recrystallisation (methanol/ether) gave the product as a white crystalline solid (50 mg).

$^1$H NMR (400 MHz, d$_6$-DMSO): δ=2.80 (t, 2 H), 3.60 (t, 2 H), 3.65 (s, 3 H), 4.60 (brs, 1 H), 5.00 (s, 1 H), 5.95 (s, 2 H), 6.65 (d, 1 H), 6.70 (s, 1 H), 6.80 (d, 1 H), 6.90 (s, 1 H), 6.95 (d, 1 H), 7.10 (d, 1 H), 7.40 (d, 2 H), 7.45 (s, 1 H), 7.75 (d, 2 H).

LRMS (Thermospray): 544.0, 545.7 (MNH$_4^+$).

EXAMPLE 91

3-(1-(1,3-Benzodioxol-5-yl)-2-[4-(2-hydroxyethoxy)phenyl]sulfonamido-2-oxoethyl)-6-hydroxymethyl-1-methyl-1H-indole

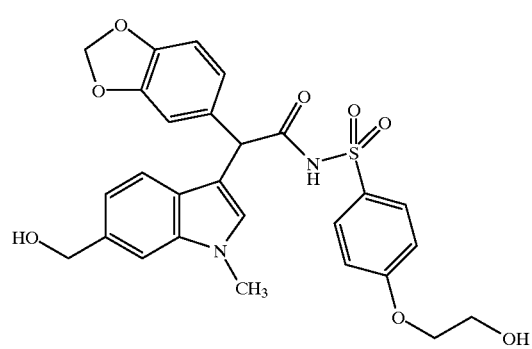

The title compound was prepared by the method of Example 90 from the compound of Example 64(b).

$^1$H NMR (400 MHz, CDCl$_3$): δ=3.50 (s, 3 H), 3.60 (t, 1 H), 3.80 (m, 2 H), 3.90 (t, 1 H), 3.95 (m, 2 H), 4.55 (d, 2 H), 4.95 (s, 1 H), 5.70 (s, 2 H), 6.50 (d, 1 H), 5.95 (s, 1 H), 6.60 (d, 1 H), 6.65 (d, 1 H), 6.80 (d, 3 H), 6.90 (d, 1 H), 7.10 (s, 1 H), 7.70 (d, 2 H).

LRMS (APCI): 540.0 (MH⁺).

EXAMPLE 92

6-Bromo-3-{1-(7-methoxy-1,3-benzodioxol-5-yl)-2-[(2-methoxy-4-methylphenyl)sulfonamido]-2-oxoethyl}-1-methyl-1H-indole (a) Methyl 2-hydroxy-2-(7-methoxy-1,3-benzodioxol-5-yl) acetate

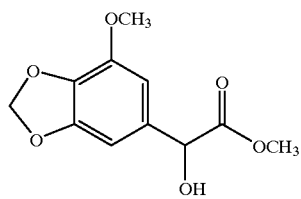

The subtitle compound was prepared using the method of Example 61(b) from 7-methoxy-1,3-benzodioxote-5-carbaldehyde (12.6 g) as a waxy solid (4.5 g).

¹H NMR (300 MHz, CDCl₃): δ=3.40 (d, 1 H exchangeable), 3.76 (s, 3 H), 3.90 (s, 3 H), 5.06 (d, 1 H), 5.97 (s, 2 H), 6.59 (s, 1 H), 6.61 (s, 1 H).

LRMS (Thermospray): 258 (MNH₄⁻)

(b) Methyl 2-bromo-2-(7-methoxy-1,3-benzodioxol-5-yl) acetate

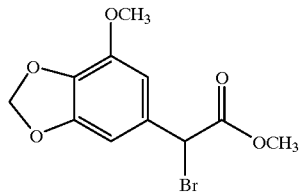

The subtitle compound was prepared from methyl 2-hydroxy-2-(7-methoxy-1,3-benzodioxol-5-yl)acetate (the product of step (a), 4.45 g, 19 mmol) by the method of Example 61(c) (yield 2.25 g).

¹H NMR (300 MHz, CDC₃): δ=3.80 (s, 3 H), 3.92 (s, 3 H), 5.25 (s, 1 H), 5.98 (s, 2 H), 6.73 (s, 1 H), 6.78 (s, 1 H).

(c) Methyl 2-(6-bromo-1H-3-indolyl)-2-(7-methoxy-1,3-benzodioxol-5-yl)acetate

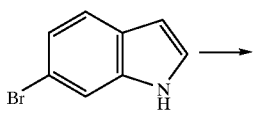

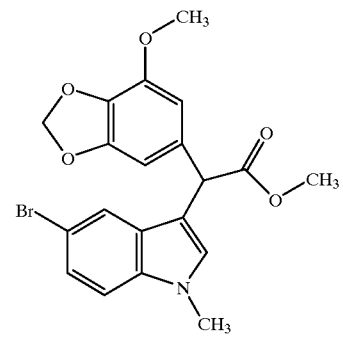

Methyl magnesium bromide (3.6 ml of 3 M solution in diethyl ether) was added dropwise to a stirred solution of 6-bromo-indole (2.13 g, 10.9 mmol) in toluene (20 ml) under a nitrogen atmosphere. After 20 minutes the reaction mixture was transferred via a cannula over ~10 minutes, to a stirred solution of methyl 2-bromo-2-(7-methoxy-1,3-benzodioxol-5-yl)acetate (from step (b), 2.2 g, 7.26 mmol) in toluene (20 ml) at ambient temperature. After a further 2 hours the mixture was poured into a mixture of diethyl ether and aqueous ammonium chloride. The organic layer was separated and dried (magnesium sulphate), and the solvent was removed in vacuo. The residue was flash chromatographed using dichloromethane as eluant to give the subtitle compound (2.7 g).

¹H NMR (300 MHz, CDCl₃): δ=3.72 (s, 3 H), 3.83 (s, 3 H), 5.08 (s, 1 H), 5.92 (s, 2 H), 6.58 (s, 2 H), 7.10–7.30 (m, 3 H), 7.50 (s, 1 H), 8.1 (br, 1 H).

LRMS (Thermospray): 420.1 (MH⁻)

(d) Methyl 2-(6-bromo-1-methyl-1H-3-indolyl)-2-(7-methoxy-1,3-benzodioxol-5-yl)acetate

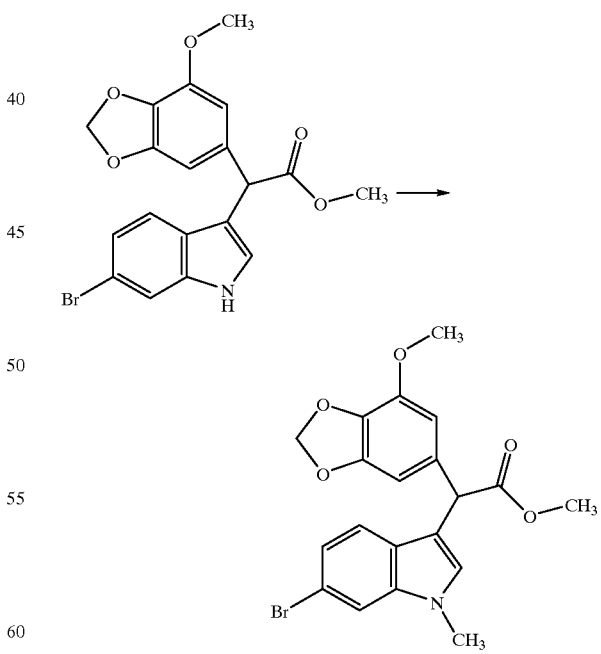

Sodium hydride (289 mg of a 60% dispersion in paraffin wax) was added in portions to a stirred solution of methyl 2-(6-bromo-1H-3-indolyl)-2-(7-methoxy-1,3-benzodioxol-5-yl)acetate (from step (c), 2.7 g, 6.5 mmol) in anhydrous dimethylformamide (20 ml) at 0° C. under a nitrogen atmosphere. After 30 minutes, methyl p-toluenesulphonate (1.34 g, 7.2 mmol) was added. After a further 1 hour the mixture was partitioned between diethyl ether and water. The organic layer was separated and washed twice with water. The organic layer was dried (magnesium sulphate) and the solvent was removed in vacuo. The residue was purified by flash column chromatography (using 30% hexane, 70% dichloromethane as eluant) to give 1.49 g of the subtitle compound.

$^1$H NMR (300 MHz, CDCl$_3$): δ=3.72 (s, 3 H), 3.75 (s, 3 H), 3.85 (s, 3 H), 5.08 (s, 1 H), 5.92 (s, 2 H), 3.78 (s, 2 H), 7.04 (s, 1 H), 7.17 (d, 1 H), 7.28 (s, 1 H), 7.43 (s, 1 H).

LRMS (Thermospray): 432.2 (MH$^-$)

(e) 6-Bromo-3-{1-(7-methoxy-1,3-benzodioxol-5-yl)-2-[2-methoxy-4-methylphenyl)sulfonamido]-2-oxoethyl}-1-methyl-1H-indole

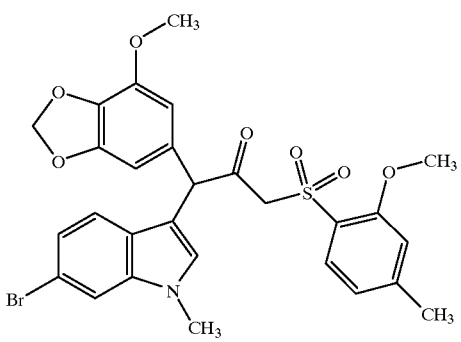

The title compound was prepared from the product of step (d) using the methods of Examples 68(c) and 79.

$^1$H NMR (300 MHz, d$_6$-DMSO): δ=2.36 (s, 3 H), 3.60 (s, 3 H), 3.69 (s, 3 H), 3.72 (s, 3 H), 5.12 (s, 1 H), 5.95 (s, 2 H), 6.39 (s, 1 H), 6.45 (s, 1 H), 6.88 (d, 1 H), 6.95 (s, 2 H), 7.07 (d, 1 H), 7.17 (d, 1 H), 7.62 (s, 1 H), 7.64 (d, 1 H), 12.20 (s, 1 H exchangeable).

LRMS (APCI): 602.9 (MH$^+$)

Analysis: Found: C, 53.47; H, 4.11; N, 4.62. C$_{27}$H$_{25}$BrN$_2$O$_7$S; requires: C, 53.91; H, 4.19; N, 4.66. m.p.: 235° C. (dec.) from methanol.

EXAMPLE 93

6-Bromo-3-{1-(6-chloro-1,3-benzodioxol-5-yl)-2-[(4-methylphenyl)sulfonamido]-2-oxoethyl}-1-methyl-1H-indole (a) Methyl 2-(6-chloro-1,3-benzodioxol-5-yl)-2-hydroxyacetate

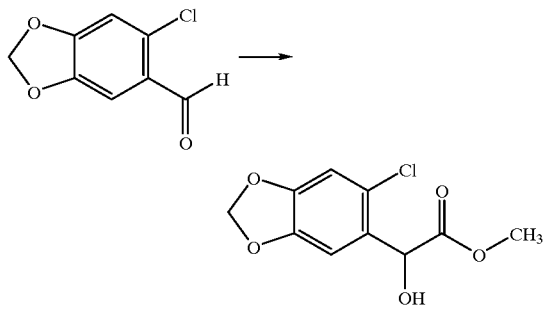

The subtitle compound was prepared by the method of Example 61(b), but starting with 6-chloro-1,3-benzodioxole-5-carbaldehyde (12.9 g). Yield 9.4 g, m.p.: 66–68° C.

$^1$H NMR (300 MHz, CDCl$_3$): δ=3.42 (d, 1 H exchangeable), 3.77 (s, 3 H), 5.48 (d, 1 H), 5.98 (s, 2 H), 6.82 (s, 1 H), 6.83 (s, 1 H).

LRMS (Thermospray): 262 (MNH$_4^+$)

(b) Methyl 2-bromo-2-(6-chloro-1,3-benzodioxol-5-yl)acetate

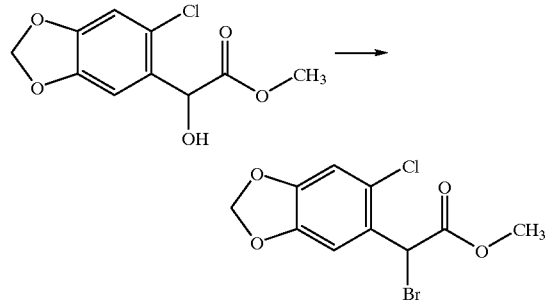

Thionyl bromide (3.7 ml) was added to a stirred solution of methyl 2-(6-chloro-1,3-benzodioxol-5-yl)-2-hydroxyacetate from step (a) (7.8 g, 32 mmol) in toluene (50 ml) at ambient temperature. After 6 hours the reaction mixture was evaporated in vacuo, and the residue was flash chromatographed using dichloromethane as eluant, followed by crystallisation from diisopropylether to give the subtitle compound (7.6 g).

$^1$H NMR (300 MHz, CDCl$_3$): δ=3.80 (s, 3 H), 5.87 (s, 1 H), 6.00 (d, 2 H), 6.80 (s, 1 H), 7.26 (s, 1 H).

(c) Methyl 2-(6-bromo-1H-3-indolyl)-2-(6-chloro-1,3-benzodioxol-5-yl)acetate

The subtitle compound was prepared following the procedure of Example 92(c), using methyl 2-bromo-2-(6-chloro-1,3-benzodioxol-5-yl)acetate from step (b), m.p. 172–174° C. from diethyl ether and hexane.

$^1$H NMR (300 MHz, CDCl$_3$): δ=3.72 (s, 3 H), 5.58 (s, 1 H), 5.86 (d, 2 H), 6.70 (s, 1 H), 6.83 (s, 1 H), 7.10–7.30 (m, 3 H), 7.50 (s, 1 H), 8.10 (br, 1 H).

LRMS (Thermospray): 441.2 (MH$^-$)

(d) Methyl 2-(6-bromo-1-methyl-1H-3-indolyl)-2-(6-chloro-1,3-benzodioxol-5-yl)acetate The subtitle compound was prepared following the procedure of Example 92(d), using methyl 2-(6-bromo-1H-3-indolyl)-2-(6-chloro-1,3-benzodioxol-5-yl)acetate from step (c). m.p. 183–185° C. from diisopropyl ether.

$^1$H NMR (300 MHz CDCl$_3$): δ=3.75 (s, 3 H), 3.76 (s, 3 H), 5.60 (s, 1 H), 5.90 (d, 2 H), 6.77 (s, 1 H), 6.87 (s, 1 H), 7.06 (s, 1 H), 7.17 (d, 1 H), 7.30 (d, 1 H), 7.45 (s, 1 H).

LRMS (Thermospray): 437.9 (MH$^+$)

(e) 6-Bromo-3-{1-(6-chloro-1,3-benzodioxol-5-yl)-2-[(4-methylphenyl)sulfonamido]-2-oxoethyl}-1-methyl-1H-indole

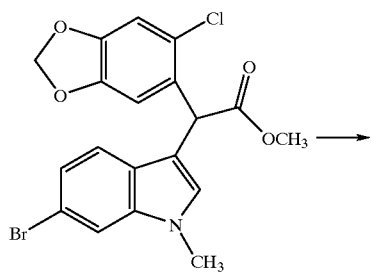

-continued

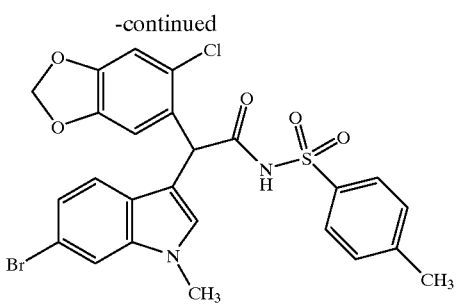

The subtitle compound was prepared from the compound of step (d) following the methods of Examples 68(c) and 79, and using the appropriate sulphonamide in the last step.

$^1$H NMR (300 MHz, CDCl$_3$): δ=2.46 (s, 3 H), 3.71 (s, 3 H), 5.36 (s, 1 H), 5.90 (s, 2 H), 6.48 (s, 1 H), 6.82 (s, 1 H), 6.85 (s, 1 H), 7.00 (d, 1 H), 7.07 (d, 1 H), 7.28 (d, 2 H), 7.45 (s, 1 H), 7.83 (d, 2 H), 8.25 (s, 1 H exchangeable).

LRMS (APCI): 575.0 (MH$^-$)

EXAMPLE 94

3-{1-(1,3-Benzodioxol-5-yl)-2-[(4-methylphenyl) sulfonamido]-2-oxoethyl}-6-formyl-1-methyl-1H-indole

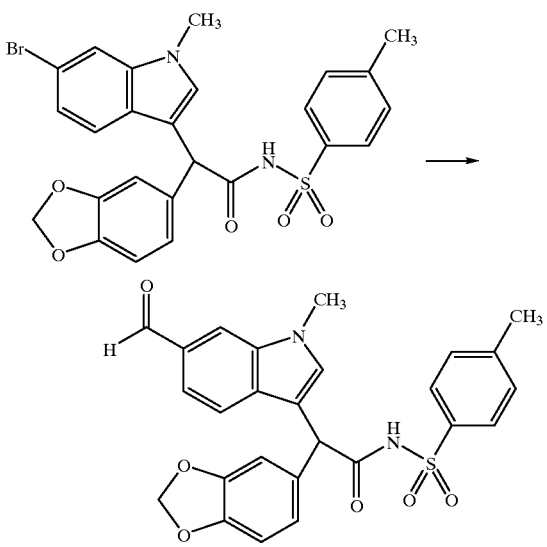

Carbon monoxide was bubbled through a stirred solution of 3-{1-(1,3-benzodioxol-5-yl)-2-[(4-methylphenyl) sulfonamido]-2-oxoethyl}-6-bromo-1-methyl-1H-indole (from Example 55, 400 mg, 0.79 mmol), sodium formate (107 mg, 1.57 mmol) and dichlorobis(triphenylphosphine)-palladium (II) (11 mg, 0.016 mmol) in dimethylformamide (6 ml) at 110° C. for 4 h. The reaction mixture was cooled and extracted from 1N hydrochloric acid with ethyl acetate (2×50 ml). The organic layers were dried (MgSO$_4$) and concentrated. Flash column chromatography (elution with 95% dichloromethane/5% methanol) gave the product (320 mg) as a fawn solid.

$^1$H NMR (400 MHz CDCl$_3$): δ=2.40 (s, 3 H), 3.80 (s, 3 H), 5.05 (s, 1 H), 5.90 (s, 2 H), 6.60 (m, 3 H), 7.05 (s, 1 H), 7.2–7.6 (m, 4 H), 7.80 (m, 3 H), 9.20 (brs, 1 H), 10.00 (s, 1 H).

LRMS (Thermospray): 491.4 (MH$^-$).

EXAMPLE 95

3-{1-(1,3-Benzodioxol-5-yl)-2-[(4-methylphenyl) sulfonamido]-2-oxoethyl}-6-(hydroxymethyl)-1-methyl-1H-indole

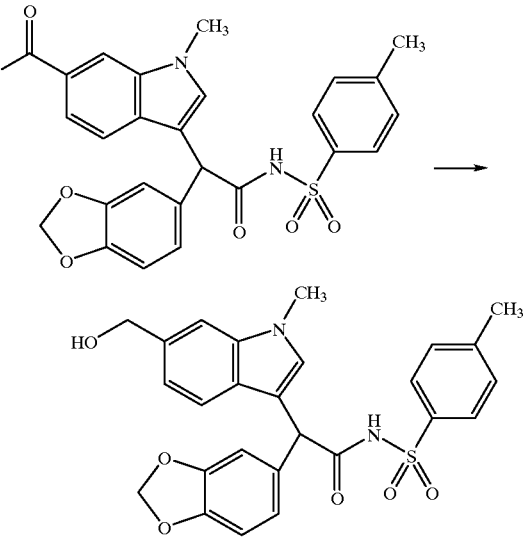

Sodium borohydride (51 mg, 1.33 mmol) was added to a stirred solution of 3-{1-(1,3-benzodioxol-5-yl)-2-[(4-methylphenyl)sulfonamido]-2-oxoethyl}-6-bromo-1-methyl-1H-indole (from Example 94, 305 mg, 0.66 mmol) in ethanol (10 ml) at room temperature under a nitrogen atmosphere. After 1 h the ethanol was removed in vacuo and the product was extracted from 0.5N hydrochloric acid (50 ml) with dichloromethane (2×50 ml). The organic layers were dried (MgSO$_4$) and concentrated. Flash column chromatography (elution with 95% dichloromethane/5% methanol) gave the product (230 mg) as a white foam.

$^1$H NMR (400 MHz, d$_6$-DMSO): δ=2.35 (s, 3 H), 3.60 (s, 3 H), 4.50 (s, 2 H), 4.95 (brs, 1 H), 5.05 (s, 1 H), 5.90 (s, 2 H), 6.60 (s, 1 H), 6.65 (d, 1 H), 6.70 (d, 2 H), 6.80 (d, 1 H), 7.00 (d, 1 H), 7.20 (s, 1 H), 7.35 (d, 2 H), 7.70 (d, 2 H).

LRMS (Thermospray): 493.2 (MH$^+$).

Analysis: Found: C, 60.40; H, 5.29; N, 5.79. C$_{26}$H$_{24}$BrN$_2$O$_6$S.1.5H$_2$O: requires: C, 60.10; H, 5.24; N, 5.39,

EXAMPLE 96

6-Formyl-3-{1-(7-methoxy-1,3-benzodioxol-5-yl)-2-[(2-methoxy-4-methylphenyl)sulfonamido]-2-oxoethyl}-1-methyl-1H-indole

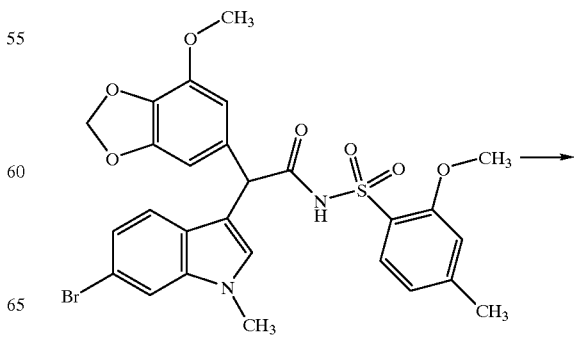

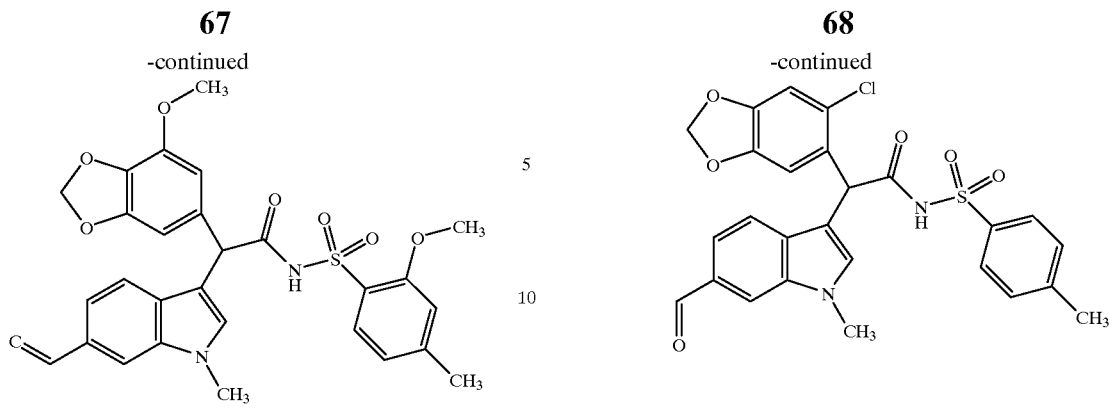

n-Butyllithium (0.8 ml of 2.5M solution in hexane) was added to a stirred solution of 6-bromo-3-{1-(7-methoxy-1,3-benzodioxol-5-yl)-2-[(2-methoxy-4-methylphenyl)sulfonamido]-2-oxoethyl}-1-methyl-1H-indole (from Example 92, 400 mg, 0.67 mmol) in anhydrous tetrahydrofuran at −75° C. under a nitrogen atmosphere. After 30 minutes dimethylformamide (0.15 ml) was added to the orange solution, and after a further 30 minutes the mixture was allowed to warm to 0° C. before quenching with excess 1N hydrochloric acid. Ethyl acetate was added and the organic layer was separated and washed with water. The organic layer was dried (magnesium sulphate), and the solvents removed in vacuo. The residue was flash chromatographed using 1% methanol in dichloromethane as eluant, and the product was crystallised from dichloromethane and diethyl ether mixture to give the title compound (187 mg).

$^1$H NMR (300 MHz, $d_6$-DMSO): δ=2.33 (s, 3 H), 3.61 (s, 3 H), 3.72 (s, 3 H), 3.80 (s, 3 H), 5.20 (s, 1 H), 5.94 (s, 2 H), 6.42 (s, 1 H), 6.50 (s, 1 H), 6.87 (d, 1 H), 6.95 (s, 1 H), 7.28 (s, 1H), 7.40 (d, 1 H), 7.50 (d, 1 H), 7.66 (d, 1 H), 8.02 (s, 1 H), 10.00 (s, 1 H), 12.28 (brs, 1 H exchangeable).

LRMS (APCI): 550.3 (MH$^+$)

Analysis: Found: C, 61.24; H, 5.17; N, 4.61. $C_{28}H_{26}N_2O_8S$: requires: C, 61.08; H, 4.76; N, 5.09.

m.p.: 233° C.-dec.

EXAMPLE 97

3-{1-(6-Chloro-1,3-benzodioxol-5-yl)-2-[(4-methylphenyl)sulfonamido]-2-oxoethyl}-6-formyl-1-methyl-1H-indole

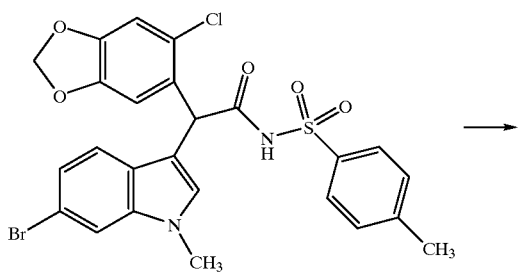

Using 6-bromo-3-{1-(6-chloro-1,3-benzodioxol-5-yl)-2-[(4-methylphenyl)sulfonamido]-2-oxoethyl}-1-methyl-1H-indole (from Example 93) the title compound was prepared in a similar way to Example 96.

$^1$H NMR (300 MHz, CDCl$_3$): δ=2.44 (s, 3 H), 3.82 (s, 3 H), 5.41 (s, 1 H), 5.90 (d, 2 H), 6.48 (s, 1 H), 6.83 (s, 1 H), 7.16 (s, 1 H), 7.20–7.33 (m, 3 H), 7.50 (d, 1 H), 7.82 (s, 1 H), 7.85 (d, 2 H), 8.40 (brs, 1H exchangeable), 10.02 (s, 1 H).

LRMS (APCI): 524.9 (MH$^+$)

EXAMPLE 98

6-(Hydroxymethyl)-3-{1-(7-methoxy-1,3-benzodioxol-5-yl)-2-[(2-methoxy-4-methylphenyl)sulfonamido]-2-oxoethyl}-1-methyl-1H-indole

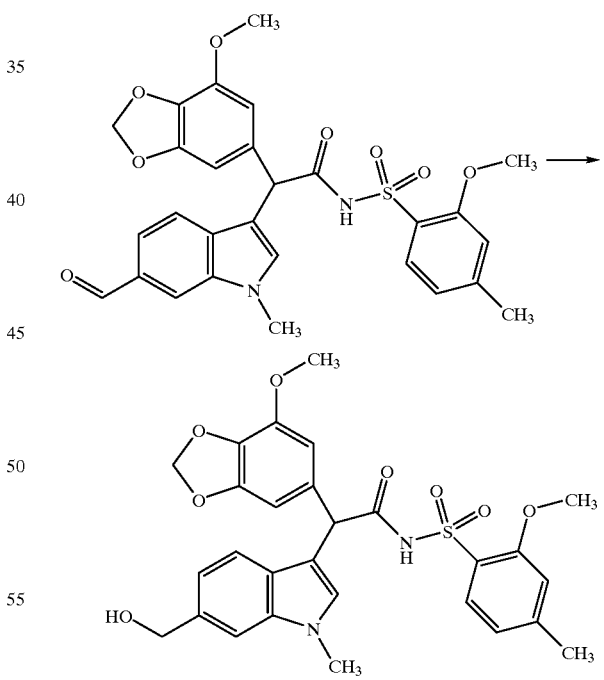

Sodium borohydride (9 mg) was added to a suspension of 6-formyl-3-{1-(7-methoxy-1,3-benzodioxol-5-yl)-2-[(2-methoxy-4-methylphenyl)sulfonamido]-2-oxoethyl}-1-methyl-1H-indole (from Example 96, 130 mg, 0.24 mmol) in a mixture of ethanol (3 ml) and 1,4-dioxane (3 ml) at ambient temperature. Stirring was continued for 1.5 hours, and then water was added dropwise until a solution was achieved. After carefully acidifying with drops of concentrated hydrochloric acid, the solvents were evaporated in vacuo. The residue was partitioned between ethyl acetate and water, and the organic layer was separated and rewashed with water. The organic layer was dried (magnesium sulphate) and the solvents removed in vacuo. The residue was crystallised from a mixture of methanol and diethyl ether to give the title compound (105 mg).

$^1$H NMR (300 MHz, d$_6$-DMSO): δ=2.35 (s, 3 H), 3.60 (s, 3 H), 3.68 (s, 3 H), 3.74 (s, 3 H), 4.56 (d, 2 H), 5.02 (t, 1 H exchangeable), 5.16 (s, 1 H), 5.92 (s, 2 H), 6.39 (s, 1 H), 6.48 (s, 1 H), 6.82–6.98 (m, 4 H), 7.16 (d, 1 H), 7.30 (s, 1 H), 7.66 (d, 1 H), 12.20 (s, 1 H exchangeable).

LRMS (Thermospray): 553.6 (MH$^-$)

Analysis: Found: C, 60.34; H, 5.43; N, 4.71. C$_{28}$H$_{28}$N$_2$O$_8$S: Requires: C, 60.86; H, 5.11; N, 5.07.

m.p.: 145–147° C.

EXAMPLE 99

3-{1-(6-Chloro-1,3-benzodioxol-5-yl)-2-[(4-methylphenyl)sulfonamido]-2-oxoethyl}-6-(hydroxymethyl)-1-methyl-1H-indole

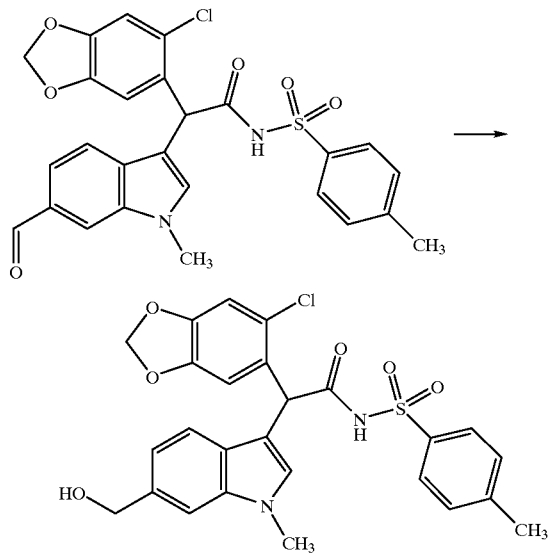

Using 3-{1-(6-Chloro-1,3-benzodioxol-5-yl)-2-[(4-methylphenyl)sulfonamido]-2-oxoethyl}-6-formyl-1-methyl-1H-indole from Example 97, the title compound was prepared by the method of Example 98.

$^1$H NMR (300 MHz, d$_6$-DMSO): δ=2.40 (s, 3 H), 3.70 (s, 3 H), 4.56 (d, 2 H), 5.05 (t, 1 H exchangeable), 5.42 (s, 1 H), 5.92 (s, 1 H), 5.96 (s, 1 H), 6.32 (s, 1 H), 6.66 (s, 1 H), 6.90 (d, 1 H), 7.03 (s, 1 H), 7.09 (d, 1 H), 7.36 (s, 1 H), 7.40 (d, 2 H), 7.73 (d, 2 H), 12.22 (s, 1 H exchangeable).

LRMS (APCI): 527.3 (MH$^-$) (Thermospray): 544.3 (MNH$_4^-$)

m.p.: 207–209° C.

EXAMPLE 100

3-{1-(1,3-Benzodioxol-5-yl)-2-[(2-methoxy-4-methylphenyl)sulfonamido]-2-oxoethyl}-5-(hydroxymethyl)-1-methyl-1H-indole

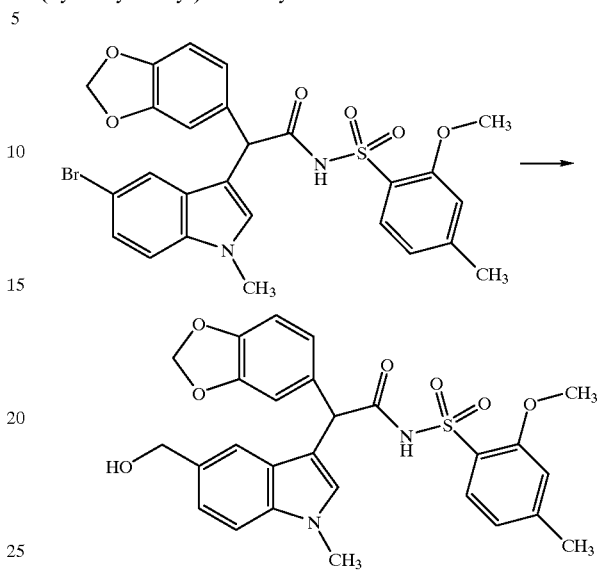

To a solution of 3-{1-(1,3-benzodioxol-5-yl)-2-[(2-methoxy-4-methylphenyl)sulfonamido]-2-oxoethyl}-5-bromo-1-methyl-1H-indole (from Example 79, 300 mg, 0.53 mmol) in 1,4-dioxane (1.5 ml) under a nitrogen atmosphere was added hydroxymethyltributylstannane (253 mg, 0.79 mmol), followed by tetrakis(triphenylphosphine)palladium (O) (30 mg). The mixture was heated to reflux for 8 hours, and then cooled. Sodium hydroxide solution (1M) was added and the mixture boiled to dissolve the product. The solution was decanted clear of an insoluble tar residue, and washed with diethyl ether. After acidification with concentrated hydrochloric acid, the aqueous mixture was extracted with ethyl acetate. The organic extract was dried (magnesium sulphate) and the solvents were evaporated in vacuo. The residue was flash chromatographed using 2% methanol in dichloromethane as eluant to give the title compound (35 mg).

$^1$H NMR (300 MHz, d$_6$-DMSO): δ=2.35 (s, 3 H), 3.58 (s, 3 H), 3.68 (s, 3 H), 4.47 (d, 2 H), 4.95 (t, 1 H exchangeable), 5.20 (s, 1 H), 5.92 (d, 2 H), 6.65–7.00 (m, 6 H), 7.08 (d, 1 H), 7.22 (s, 1 H), 7.30 (d, 1 H), 7.65 (d, 1 H), 12.40 (s, 1H exchangeable).

LRMS (Thermospray): 540.0 (MNH$_4^+$)

EXAMPLE 101

6-Acetyl-3-{1-(1,3-benzodioxol-5-yl)-2-[(2-methoxy-4-methylphenyl)sulfonamido]-2-oxoethyl}-1-methyl-1H-indole

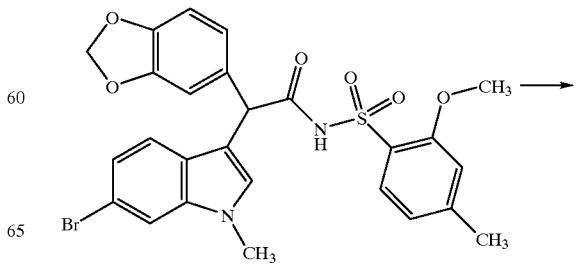

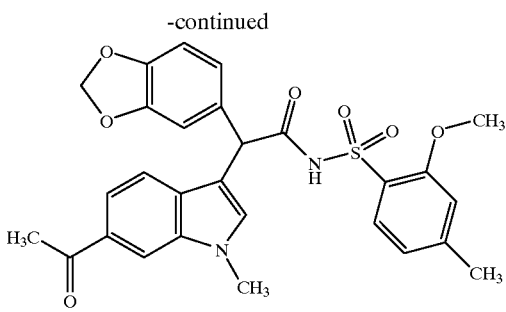

A mixture of 3-{1-(1,3-benzodioxol-5-yl)-2-[(2-methoxy-4-methylphenyl)sulfonamido]-2-oxoethyl}-6-bromo-1-methyl-1H-indole (from Example 85, 300 mg, 0.53 mmol), ethyl vinyl ether (0.063 ml), palladium(II)acetate (6 mg), tri-o-tolylphosphine (13 mg) and triethylamine (0.1 ml) in acetonitrile (5 ml) was heated at reflux for 18 hours under a nitrogen atmosphere. After cooling, the solvent was evaporated in vacuo and the residue was stirred with 2N hydrochloric acid (~6 ml) for 45 minutes. The mixture was twice extracted with ethyl acetate, and then washed with water, and brine. The organic layer was dried (magnesium sulphate) and the solvents were evaporated in vacuo. The residue was flash chromatographed using a gradient elution of a mixture of 90% hexane and 10% ethyl acetate, through to 40% hexane and 60% ethyl acetate, to give the title compound (80 mg).

$^1$H NMR (400 MHz, CDCl$_3$): δ=2.38 (s, 3 H), 2.60 (s, 3 H), 3.42 (s, 3 H), 3.70 (s, 3 H), 5.00 (s, 1 H), 5.89 (s, 2 H), 6.55 (s, 1 H), 6.60–6.70 (m, 3 H), 6.83 (d, 1 H), 7.03 (s, 1 H), 7.21 (d, 1 H), 7.55 (d, 1 H), 7.90 (m, 2 H), 8.80 (s, 1 H, exchangeable).

LRMS (APCI): 534.7 (MH$^-$)

Analysis: Found: C, 60.20; H, 4.84; N, 4.83. C$_{28}$H$_{26}$N$_2$O$_7$S; 0.4 CH$_2$Cl$_2$ Requires: C, 60.00; H, 4.75; N, 4.93.

EXAMPLE 102
3-{1-(1,3-Benzodioxol-5-yl)-2-[(2-methoxy-4-methylphenyl)sulfonamido]-2-oxoethyl}-6-(methoxymethyl)-1-methyl-1H-indole

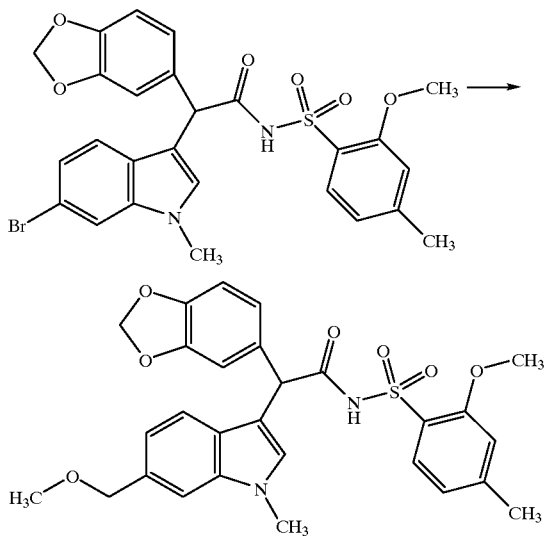

To a solution of 3-{1-(1,3-benzodioxol-5-yl)-2-[(2-methoxy-4-methylphenyl)sulfonamido]-2-oxoethyl}-6-bromo-1-methyl-1H-indole (from Example 85, 300 mg, 0.53 mmol) in 1,4-dioxane (1.5 ml) under a nitrogen atmosphere was added methoxymethyltributylstannane (220 mg, 0.66 mmol), followed by tetrakis(triphenylphosphine)palladium (O) (35 mg). The mixture was heated to reflux for 16 hours, and then cooled. An additional portion of tetrakis (triphenylphosphine)palladium(O) (30 mg) was added, and reflux was continued for a further 8 hours. The solvent was removed in vacuo, and the residue was flash chromatographed using a gradient elution of a mixture of 1% methanol and 99% dichloromethane, through to 5% methanol and 95% dichloromethane, to give the title compound (33 mg).

$^1$H NMR (400 MHz, CDCl$_3$): δ=2.37 (s, 3 H), 3.38 (s, 3 H), 3.40 (s, 3 H), 3.65 (s, 3 H), 4.53 (s, 2 H), 4.99 (s, 1 H), 5.88 (s, 2 H), 6.57 (s, 1 H), 6.62–6.71 (m, 3 H), 6.83 (s, 1 H), 6.84 (d, 1 H), 6.92 (d, 1 H), 7.15 (d, 1 H), 7.25 (s, 1 H), 7.90 (d, 1 H), 8.77 (s, 1 H, exchangeable).

LRMS (APCI): 536.9 (MH$^-$)

EXAMPLE 103

N6-Methoxy-N6,1-dimethyl-3-{1-(1,3-benzodioxol-5-yl)-2-[(4-methylphenyl)-sulfonamido]-2-oxoethyl}-1H-6-indolecarboxamide

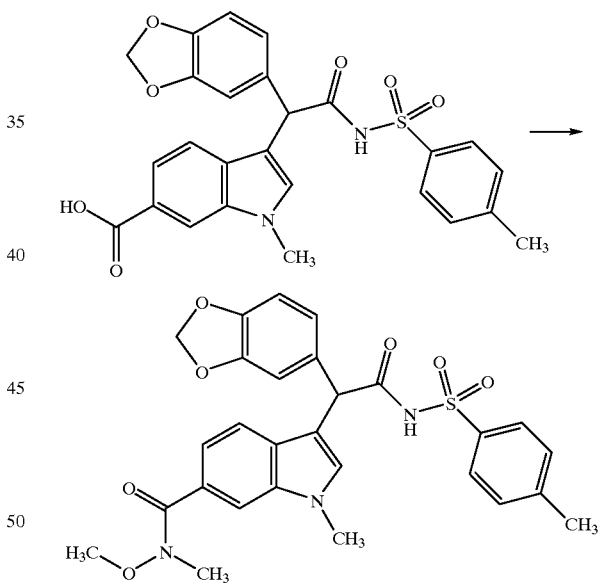

6-Bromo-1-methylindole was treated according to the method of Example 65(a), but using (4-methylphenyl) sulphonamide in place of the sulphonamide of Preparation 11, to give the methyl ester, which was then treated by the method of Example 4 to give the corresponding acid, which was then converted to the title compound by the method of Example 5 using (CH$_3$O)CH$_3$NH.

$^1$H NMR (400 MHz, CDCl$_3$): δ=2.47 (s, 3 H), 3.42 (s, 3 H), 3.59 (s, 3 H), 3.75 (s, 3 H), 4.98 (s, 1 H), 5.93 (s, 2 H), 6.65–6.77 (m, 3 H), 6.89 (s, 1 H), 7.02 (d, 1 H), 7.22–7.34 (m, 3 H), 7.72 (s, 1 H), 7.82 (d, 2 H), 8.55 (brs, 1H exchangeable).

Analysis: Found: C, 59.14; H, 4.84; N, 7.35. $C_{28}H_{27}N_2O_7S$; 0.6 $CH_2Cl_2$: Requires: C, 59.11; H, 4.84; N, 7.31.

EXAMPLE 104
6-Acetyl-3-{1-(1,3-benzodioxol-5-yl)-2-[(4-methylphenyl) sulfonamido]-2-oxoethyl}-1-methyl-1H-indole

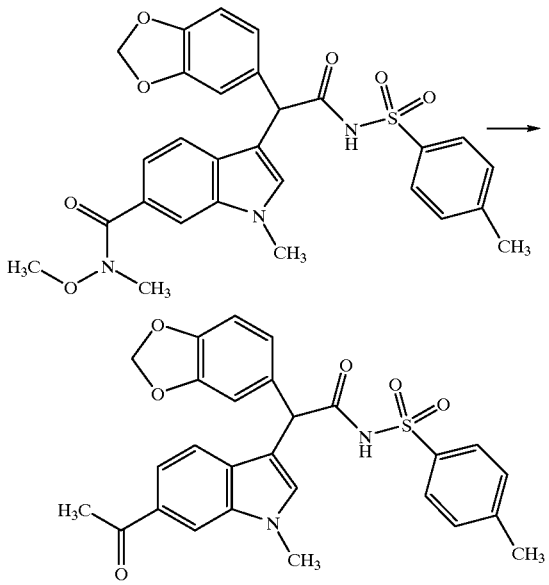

Methylmagnesium bromide (0.23 ml of a 3M solution in diethyl ether) was added dropwise to a stirred solution of N6-methoxy-N6,1-dimethyl-3-{1-(1,3-benzodioxol-5-yl)-2-[(4-methylphenyl)sulfonamido]-2-oxoethyl}-1H-6-indolecarboxamide (from Example 103, 174 mg, 0.32 mmol) in anhydrous tetrahydrofuran (5 ml) at −70° C. under a nitrogen atmosphere. The mixture was stirred at −70° C. for an additional 2 hours before warming to room temperature. Aqueous hydrochloric acid (5 ml of 1M solution) was slowly added to the mixture, and then it was extracted with ethyl acetate (100 ml). The organic phase was separated and washed with brine, dried (magnesium sulphate) and the solvent were removed in vacuo. The residue was flash chromatographed using a gradient elution of a mixture of 90% hexane and 10% ethyl acetate, through to 100% ethyl acetate, to give the title compound (18 mg).

$^1$H NMR (400 MHz, $d_6$-DMSO): δ=2.30 (s, 3 H), 2.56 (s, 3 H), 3.73 (s, 3 H), 4.90 (s, 1 H), 5.87 (d, 2 H), 6.65–6.77 (m, 3 H), 7.12 (s, 1 H), 7.17–7.23 (m, 3 H), 7.44 (d, 1 H), 7.60 (d, 2 H), 7.97 (s, 1 H), 12.40 (brs, 1 H exchangeable).

LRMS (Thermospray): 506.0 ($MH^+$), 522.6 ($MNH_4^+$)

EXAMPLE 105
3-{1-(1,3-Benzodioxol-5-yl)-2-[(4-methylphenyl) sulfonamido]-2-oxoethyl}-1-methyl-6-(2-pyridylcarbonyl)-1H-indole

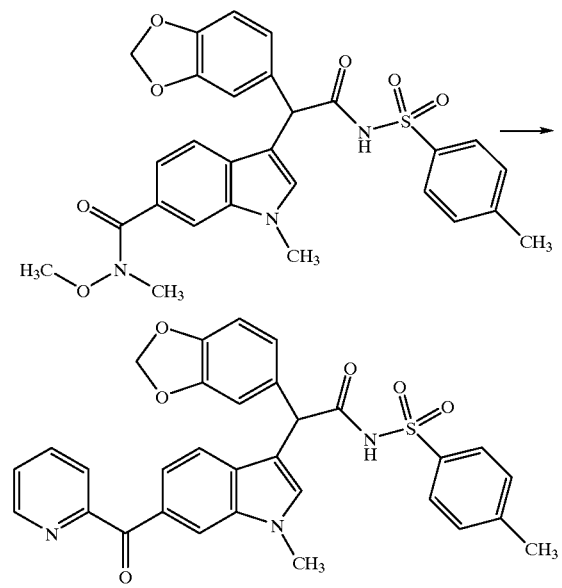

n-Butyllithium (0.32 ml of 2.5 M solution in hexane) was added to a stirred solution of 2-bromopyridine (0.08 ml, 0.8 mmol) in anhydrous tetrahydrofuran (5 ml) at −70° C. under a nitrogen atmosphere. After 30 minutes a solution of N6-methoxy-N6,1-dimethyl-3-{1-(1,3-benzodioxol-5-yl)-2-[(4-methylphenyl)sulfonamido]-2-oxoethyl}-1H-6-indolecarboxamide (the compound of Example 103, 200 mg, 0.36 mmol) in anhydrous tetrahydrofuran (2 ml) was added to the mixture at −70° C. The mixture was stirred at −70° C. for an additional 4 hours before being warmed to 0° C. and then quenched with the addition of water (5 ml).

The mixture was acidified with acetic acid, and extracted with ethyl acetate (100 ml). The organic phase was separated and washed with brine, dried (magnesium sulphate) and the solvent was removed in vacuo. The residue was flash chromatographed using a gradient elution of a mixture of 90% hexane and 10% ethyl acetate, through to 100% ethyl acetate, to give the title compound (42 mg).

$^1$H NMR (400 MHz, $CDCl_3$): δ=2.42 (s, 3 H), 3.73 (s, 3 H), 4.98 (s, 1 H), 5.91 (s, 2 H), 6.60–6.70 (m, 3 H), 6.98 (s, 1 H), 7.10 (d, 1 H), 7.27 (d, 2 H), 7.48 (dd, 1 H), 7.62 (d, 1 H), 7.81 (d, 2 H), 7.90 (dd, 1 H), 8.00 (d, 1 H), 8.10 (s, 1 H), 8.72 (d, 1 H).

LRMS (APCI): 568.3 ($MH^+$)

EXAMPLE 106

3-{1-(1,3-Benzodioxol-5-yl)-2-[(4-methylphenyl)sulfonamido]-2-oxoethyl}-1-methyl-6-[2-(2-pyridyl)acetyl]-1H-indole

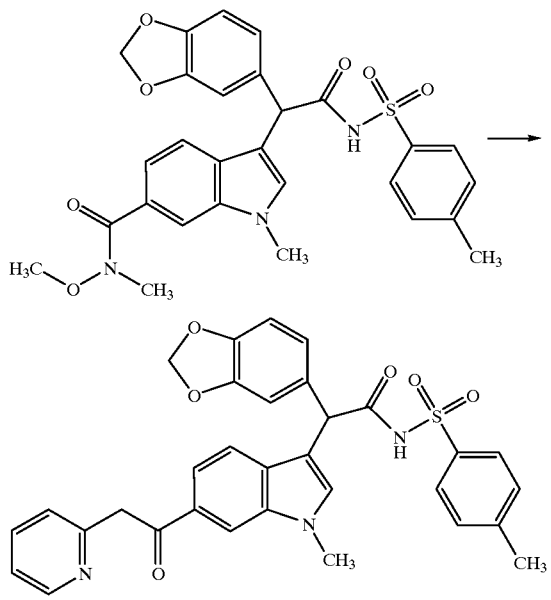

Lithium diisopropylamide mono(tetrahydrofuran) (0.53 ml of 1.5M solution in cyclohexene) was added to a stirred solution of 2-methylpyridine (0.08 ml, 0.8 mmol) in anhydrous tetrahydrofuran (3 ml) at −70° C. under a nitrogen atmosphere. After 20 minutes a solution of N6-methoxy-N6,1-dimethyl-3-{1-(1,3-benzodioxol-5-yl)-2-[(4-methylphenyl)sulfonamido]-2-oxoethyl}-1H-6-indolecarboxamide (the compound of Example 103, 200 mg, 0.36 mmol) in anhydrous tetrahydrofuran (2 ml) was added to the mixture at −70° C. The mixture was stirred at −70° C. for an additional 2 hours before being warmed to 0° C. and then quenched with the addition of water (5 ml). The mixture was acidified with acetic acid, and extracted with ethyl acetate (100 ml). The organic phase was separated and washed with brine, dried (magnesium sulphate) and the solvent was removed in vacuo. The residue was flash chromatographed using a gradient elution of a mixture of 90% hexane and 10% ethyl acetate, through to 100% ethyl acetate, to give the title compound (95 mg).

$^1$H NMR (400 MHz, d$_6$-DMSO): Complex due to keto and enol forms of the (2-pyridyl)acetyl group of the compound.

$^1$H NMR (300 MHz TFA-d): δ=2.43 (s, 3 H), 3.79 (s, 3 H), 5.21 (s, 1 H), 5.90 (s, 2 H), 6.62 (s, 1 H), 6.66 (d, 1 H), 6.75 (d, 1 H), 7.02 (s, 1 H), 7.30–7.40 (m, 3 H), 7.70 (d, 1 H), 7.81 (d, 2 H), 7.96–8.08 (m, 2 H), 8.13 (s, 1 H), 8.59 (dd, 1 H), 8.78 (d, 1 H), 11.5 (exchanged NH, and the CH$_2$ of (2-pyridyl)acetyl group).

LRMS (APCI): 582.7 (MH$^+$)

EXAMPLE 107

1-Allyl-3-{1-(1,3-benzodioxol-5-yl)-2-[(4-methylphenyl)sulfonamido]-2-oxoethyl}-1H-6-indolecarboxamide

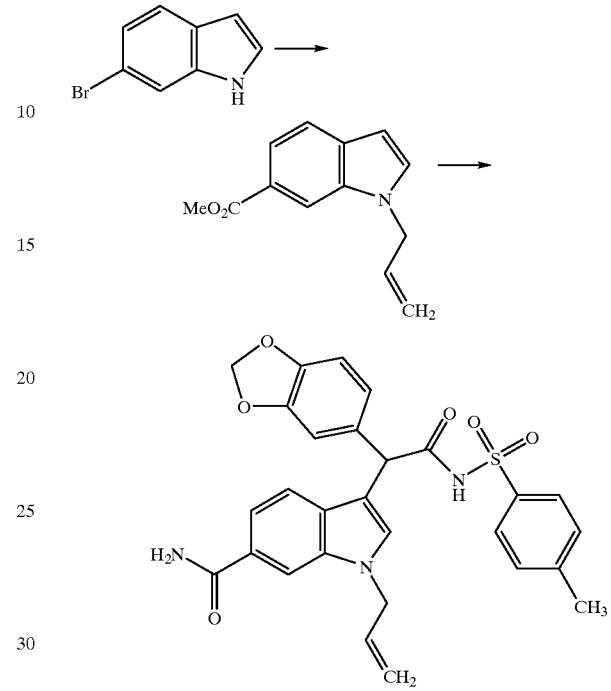

The title compound was prepared from 6-bromo-1-ethylindole using the methods of Examples 1(a) (but using allyl bromide in place of ethyl bromide), 1(b), 1(d), 2, 3 (but using (4-methylphenyl)sulphonamide), 4 and 12.

$^1$H NMR (300 MHz, CD$_3$OD): δ=2.40 (s, 3 H), 4.65 (d, 2 H), 4.95 (d, 1 H), 5.00 (s, 1 H), 5.10 (d, 1 H), 5.80 (d, 2 H), 5.95 (m, 1 H), 6.70 (m, 3 H), 6.95 (s, 1 H), 7.10 (s, 1 H), 7.20 (d, 2 H), 7.40 (d, 1 H), 7.70 (d, 2 H), 7.80 (s, 1 H).

LRMS (Thermospray): 549.3 (MNH$_4^-$).

EXAMPLE 108

3-{1-(1,3-Benzodioxol-5-yl)-2-[(4-methylphenyl)sulfonamido]-2-oxoethyl}-1-(2-hydroxyethyl)-1H-6-indolecarboxamide

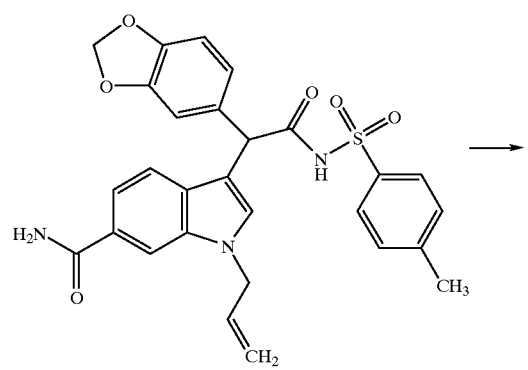

-continued

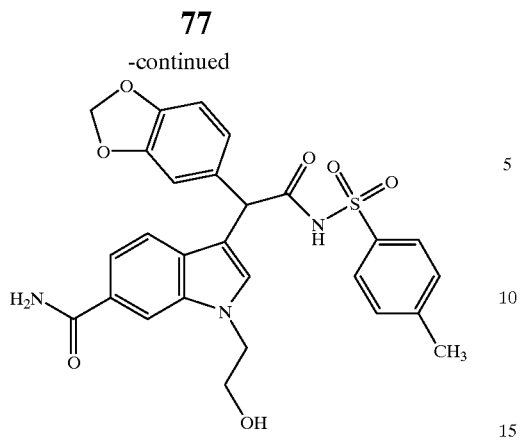

Osmium tetroxide (239 mg, 0.94 mmol), pyridine (0.225 ml, 4.7 mmol) and N-methylmorpholine N-oxide (549 mg, 2.84 mmol) were added to a stirred solution of 1-allyl-3-{1-(1, 3-benzodioxol-5-yl)-2-[(4-methylphenyl)sulfonamido]-2-oxoethyl}-1H-6-indolecarboxamide (the compound of Example 107) in aqueous tetrahydrofuran (10 ml tetrahydrofuran: 1 ml H$_2$O) at room temperature. After 4 h a solution of sodium thiosulphate (10 ml) was added and stirring continued for 1 h. The black precipitate was removed by filtration through celite and the solvent removed in vacuo. The crude diol was redissolved in ethyl acetate (50 ml) and washed with 1M hydrochloric acid (50 ml) then brine (50 ml). The organic layer was dried (MgSO$_4$) and concentrated to give a brown solid. Sodium metaperiodate (1.0 g, 4.7 mmol) dissolved in water (1 ml) was added to a stirred slurry of the brown solid in ethyl acetate (10 ml). After 2 h the mixture was filtered, diluted with ethyl acetate (50 ml) and washed with saturated sodium chloride solution. The organic layer was dried (magnesium sulphate) and concentrated in vacuo Partial purification was undertaken at this stage by flash column chromatography (elution with 90% dichloromethane/10% methanol) giving an aldehyde intermediate as a fawn solid. Without further purification this solid was dissolved in methanol (15 ml) at room temperature under a nitrogen atmosphere. Sodium borohydride (36 mg) was added portionwise over 10 minutes and stirring was continued for 4 h. The methanol was removed in vacuo and the residue redissolved in ethyl acetate (50 ml). The ethyl acetate solution was washed with saturated aqueous NH$_4$Cl (50 ml), dried (MgSO$_4$) and concentrated to give a yellow foam. Flash column chromatography (elution with 90% dichloromethane/10% methanol) gave the product as a fawn solid (126 mg).

$^1$H NMR (300 MHz, d$_6$-DMSO): δ=2.40 (s, 3 H), 3.60 (m, 2 H), 4.10 (m, 2 H), 5.10 (s, 1 H), 5.90 (s, 1 H), 6.65 (s, 1 H), 6.70 (d, 1 H), 6.80 (d, 1 H), 7.10 (s, 1 H), 7.15 (d, 1 H), 7.30 (d, 2 H), 7.40 (d, 1 H), 7.70 (d, 2 H), 8.00 (s, 1 H).

LRMS (APCI): 536.2 (MH$^-$).

EXAMPLE 109

3-{1-1,3-benzodioxol-5-yl)-2-[(4-methyl-2-methoxyphenyl)sulfonamido]-2-oxoethyl}-1-(2-methoxyethyl)-1H-6-indolecarboxamide

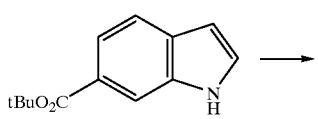

-continued

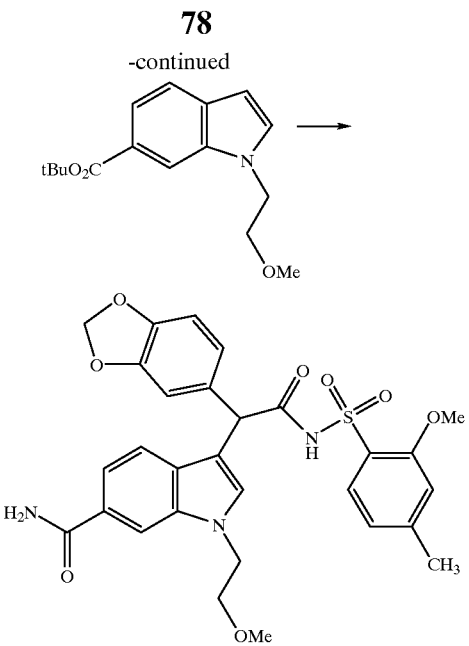

The title compound was prepared from the compound of Example 28(b) using the methods of Examples 28(c) (but using CH$_3$OCH$_2$CH$_2$Br in place of methyl iodide), 28(d), 28(e), 28(f) and 28(g) (but using the sulphonamide of Preparation 11 in place of p-toluenesulphonamide).

$^1$H NMR (300 MHz, d$_6$-DMSO): δ=2.35 (s, 3 H), 3.20 (s, 3 H), 3.60 (m, 2 H), 3.65 (s, 3 H), 4.20 (m, 2 H), 5.20 (s, 1 H), 5.95 (s, 2 H), 6.70 (s, 1 H), 6.75 (d, 1 H), 6.80 (d, 1 H), 6.85 (d, 1 H), 6.90 (s, 1 H), 7.15 (s, 1 H), 7.20 (d, 1 H), 7.45 (d, 1 H), 7.60 (d, 1 H), 7.80 (brs, 1 H), 8.00 (s, 1 H).

LRMS (Thermospray): 580.8 (MH$^-$).

EXAMPLE 110

The compounds of Examples 17, 50, 65, 83 101 and 109 were tested in Test A above, and found to have an IC$_{50}$(ET$_A$) <500 nM, and a selectivity for ET$_A$ receptors over ET$_B$ receptors of greater than 100.

The preparation of some aromatic sulphonamides is described below.

PREPARATION 1

2-Ethyl-4-methyl-1-benzenesulfonamide

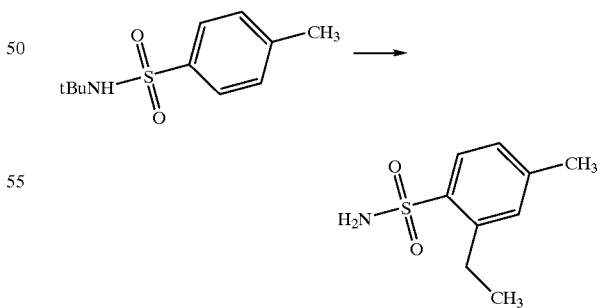

n-Butyllithium (5.3 ml of 2.5M in hexane solution) was added to a stirred solution of N1-(tert-butyl)-2-ethyl-4-methyl-1-benzenesulfonamide (1 g, 4.45 mmol) in tetrahydrofuran (30 ml) at 0° C. under a nitrogen atmosphere. After 2 h bromoethane was added dropwise. After 4 h the reaction mixture was poured into aqueous ammonium chloride and the product was extracted with ethyl acetate (2×100 ml). The combined organic fractions were washed with brine (100 ml), dried (MgSO$_4$) and concentrated in vacuo. A mixture of ethyl acetate (8 ml) and hexane (2 ml) was added and a white solid crystallised (450 mg).

$^1$H NMR (400 MHz, CDCl$_3$): δ=1.20 (s, 9 H), 1.30 (t, 3 H), 2.40 (s, 3 H), 3.00 (q, 2 H), 4.40 (s, 1 H), 7.00 (d, 1 H), 7.10 (s, 1 H), 7.80 (d, 1 H).

LRMS (Thermospray): 256.4 (MH$^+$).

Polyphosphoric acid (approx. 10 ml) was added to this white solid and the slurry was heated at 100° C. for 30 mins. The yellow solution was then carefully poured into iced water (100 ml) and extracted with ethyl acetate (2×100 ml). The organic layers were dried (MgSO$_4$) and concentrated. The product was purified by flash column chromatography (gradient elution from dichloromethane to 5%methanol/dichloromethane) giving the desired sulphonamide as a white solid.

$^1$H NMR (400 MHz, CDCl$_3$): δ=1.30 (t, 3 H), 2.40 (s, 3 H), 3.00 (q, 2 H), 4.80 (brs, 2 H), 7.05 (d, 1 H), 7.20 (s, 1 H), 7.80 (d, 1 H).

LRMS (Thermospray): 216.5 (MNH$_4$$^-$).

PREPARATION 2
2-Fluoro-4-methyl-1-benzenesulfonamide

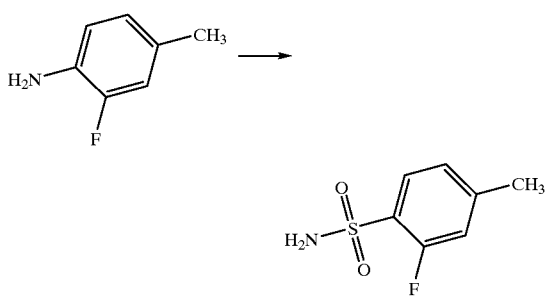

2-Fluoro-4-methylaniline (3 g, 24 mmol) was dissolved in glacial acetic acid (45 ml) and concentrated hydrochloric acid (15 ml) and the solution was cooled to −10° C. with overhead stirring. Sodium nitrite (1.82 g, 26.4 mmol) in water (3 ml) was added dropwise over 0.5 h maintaining the temperature below −5° C. Stirring was continued for a further 0.5 h after the final addition. This mixture was added in small portions to a stirred, saturated solution of sulphur dioxide in acetic acid (30 ml) at 0° C. After addition the mixture was warmed to room temperature and stirred for 1 h before pouring into iced water. After stirring for 0.5 h the product was extracted into ether and the aqueous layer further extracted with dichloromethane. The organic layers were combined, washed with brine, dried (MgSO$_4$) and concentrated (azeotroping with toluene to remove any remaining acetic acid). A mixture of 1,4-dioxan (30 ml) and aqueous ammonia (30 ml of 0.88M) was added to the residue which was stirred overnight. The 1,4-dioxan was removed in vacuo and the aqueous layer extracted with ethyl acetate (2×100 ml). The organic layers were combined, washed with brine (100 ml), dried (MgSO$_4$) and concentrated. Flash column chromatography (elution with 99% dichloromethane/1% methanol) gave the product as a pale yellow solid (1.62 g).

$^1$H NMR (400 MHz, CDCl$_3$): δ=1.30 (t, 3 H), 2.40 (s, 3 H), 3.00 (q, 2 H), 4.80 (brs, 2 H), 7.05 (d, 1 H), 7.20 (s, 1 H), 7.80 (d, 1 H).

LRMS (APCI): 216.5 (MNH$_4$$^+$).

PREPARATION 3
Ethyl (E)-3-(4-sulfamoylphenyl)-2-propenoate

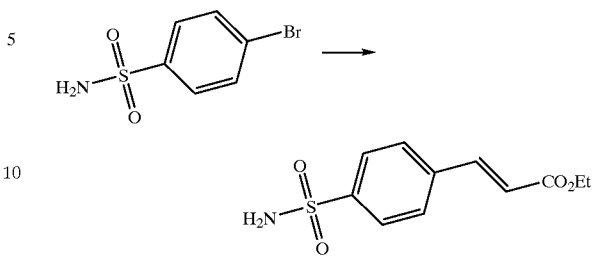

The title compound was prepared by the method of Example 57 from the starting material shown.

$^1$H NMR (400 MHz, CD$_3$OD): δ=1.40 (t, 3 H), 4.25 (q, 2 H), 6.60 (d, 1 H), 7.70 (d, 1 H), 7.75 (d, 2 H), 7.90 (d, 2 H).

LRMS (Thermospray): 272.9 (MNH$_4$$^-$).

PREPARATION 4
5-Methyl-2-pyridinesulfonamide

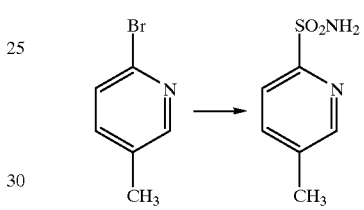

Sec-butyllithium (9.8 ml of 1.3 M in cyclohexane) and N,N,N'N'-tetramethylethylenediamine (1.8 ml, 12.2 mmol) were added to a stirred solution of 2-bromo-5-methylpyridine (2 g, 11.6 mmol) at −78° C. under a nitrogen atmosphere. After 90 min sulphur dioxide (approximately 30 ml) was condensed into the reaction mixture using a cold finger and the reaction mixture was slowly warmed to room temperature over 12 h. The reaction mixture was concentrated to dryness and the residue dissolved in ice-water. To this was added a mixture of sodium hydroxide (1.39 g, 35 mmol) and hydroxylamine sulphonic acid (3.9 g, 35 mmol) in water (20 ml). After 24 h the solution was extracted with ethyl acetate, dried (MgSO$_4$) and concentrated. Flash column chromatography (95% dichloromethane/5% methanol) gave the product (250 mg) as a clear oil which crystallised on standing.

$^1$H NMR (400 MHz, CDCl$_3$): δ=2.40 (s, 3 H), 5.20 (brs, 2 H), 7.80 (d, 1 H), 7.90 (d, 1 H), 8.50 (s, 1 H).

LRMS (Thermospray): 172.8 (MH$^+$).

PREPARATION 5
6-(Dimethylamino)-3-pyridinesulfonamide

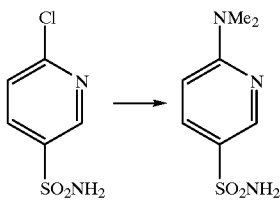

Chlorosulphonamide (500 mg) was dissolved in ethanol (5 ml) and dimethylamine (15 ml of a 2M solution in tetrahydrofuran). The reaction mixture was sealed in a pressure bomb and heated at 100° C. for 12 h. The mixture was cooled and the solvent removed in vacuo. Flash column chromatography (elution with 95% dichloromethane/5% methanol) gave the product (500 mg) as a pale orange solid.

$^1$H NMR (400 MHz, CDCl$_3$): δ=3.20 (s, 6 H), 4.80 (brs, 2 H), 6.50 (d, 1 H), 7.80 (d, 1 H), 8.65 (s, 1 H).

LRMS (Thermospray): 202.2 (MH$^-$).

PREPARATION 6
5-Chloro-2-ethoxy-4-methyl-1-benzenesulfonamide
(a) 1-Chloro-4-ethoxy-2-methylbenzene

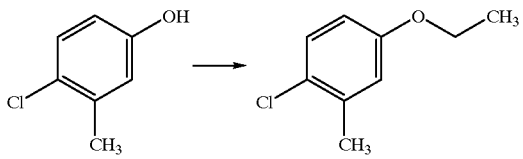

To a solution of 1-chloro-4-hydroxymethylbenzene (14.2 g, 0.1 mol) in tetrahydrofuran (250 ml) was added sodium hydride as a 40% suspension in oil (4 g, 0.1 mol) portionwise under nitrogen. When effervescence ceased iodoethane (15.6 g, 0.1 mol) was added and the solution heated at reflux for 8 hours. The reaction was quenched with water and extracted with ethyl acetate. The organic layer was washed with dilute aqueous sodium hydroxide and brine, then dried (MgSO$_4$) and evaporated to dryness. The subtitle compound was obtained as a clear oil (17.3 g).

$^1$H NMR (300 MHz CDCl$_3$): δ=1.40 (t, 3 H), 2.35 (s, 3 H), 4.00 (q, 2 H), 6.65 (dt, 1 H), 6.75 (d, 1 H), 7.20 (d, 1 H).

(b) 5-Chloro-2-ethoxy-4-methyl-1-benzenesulfonamide

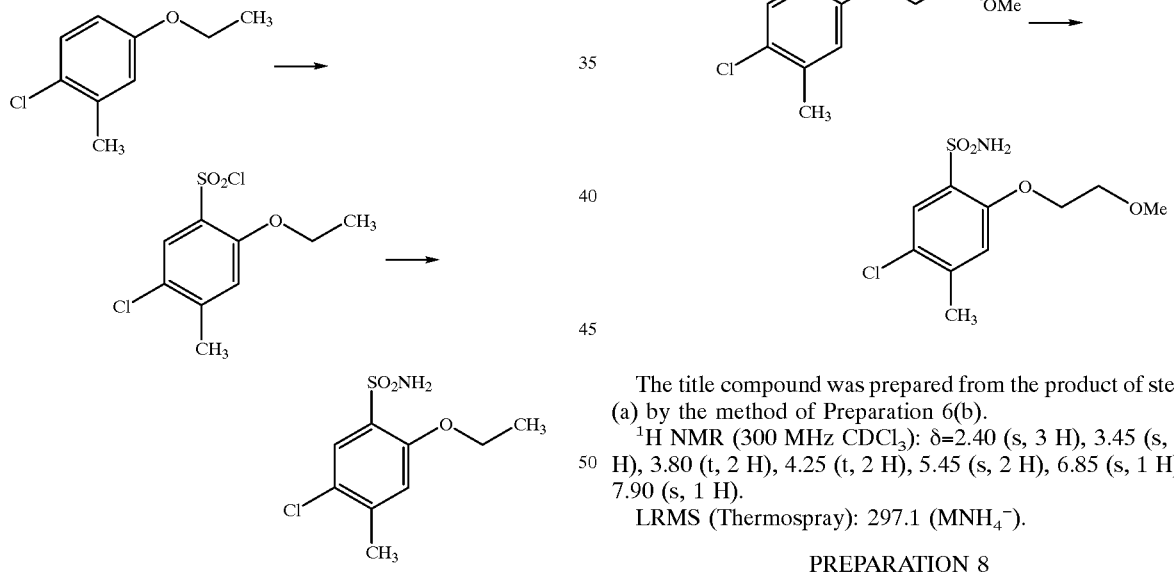

To 1-chloro-4-ethoxy-2-methylbenzene (from step (a), 17 g) was added chlorosulphonic acid (25 ml) dropwise with stirring and ice cooling. The solution was stirred for 30 minutes then poured onto ice (200 ml) and the crude intermediate sulphonyl chloride filtered off. This material was mixed thoroughly with ammonium carbonate solid (35 g) and heated at 100° C. for 30 minutes. The mixture was cooled and poured into ice water then filtered off and crystallised from hot ethyl acetate (15.2 g), m.p. 153–5° C.

$^1$H NMR (300 MHz d$_6$-DMSO): δ=1.40 (t, 3 H), 2.40 (s, 3 H), 4.20 (q, 2 H), 7.00 (s, 2 H), 7.25 (s, 1 H), 7.60 (s, 1 H).

LRMS (Thermospray): 267.5 (MNH$_4^+$).

PREPARATION 7
5-Chloro-2-(2-methoxyethoxy)-4-methyl-1-benzenesulfonamide
(a) 1-Chloro-4-(2-methoxyethoxy)-2-methylbenzene

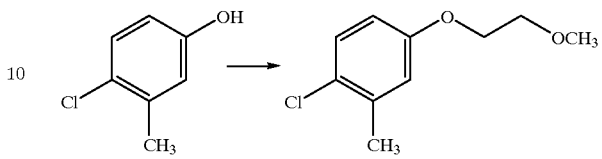

The subtitle compound was prepared using the method of Preparation 6(a), but using CH$_3$OCH$_2$CH$_2$Br in place of iodoethane.

$^1$H NMR (300 MHz CDCl$_3$): δ=2.35 (s, 3 H), 3.45 (s, 3 H), 3.75 (t, 2 H), 4.05 (t, 2 H), 6.70 (dd, 1 H), 6.80 (d, 1 H), 7.20 (d, 1 H).

(b) 5-Chloro-2-(2-methoxyethoxy)-4-methyl-1-benzenesulfonamide

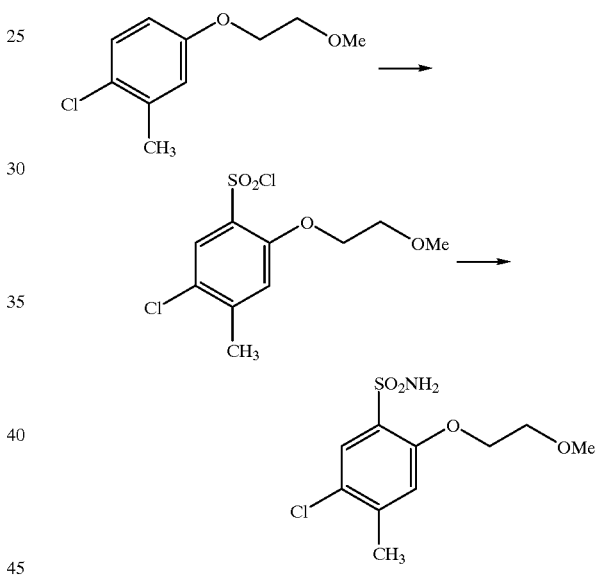

The title compound was prepared from the product of step (a) by the method of Preparation 6(b).

$^1$H NMR (300 MHz CDCl$_3$): δ=2.40 (s, 3 H), 3.45 (s, 3 H), 3.80 (t, 2 H), 4.25 (t, 2 H), 5.45 (s, 2 H), 6.85 (s, 1 H), 7.90 (s, 1 H).

LRMS (Thermospray): 297.1 (MNH$_4^-$).

PREPARATION 8
5-Chloro-2-methoxy-4-methyl-1-benzenesulfonamide

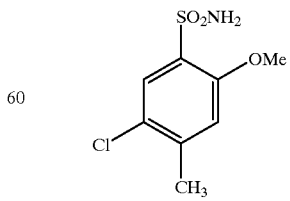

The title compound was prepared by the method of Preparation 6, but using iodomethane in place of iodoethane.

¹H NMR (300 MHz CDCl₃): δ=2.40 (s, 3 H), 4.00 (s, 3 H), 5.00 (s, 2 H), 6.90 (s, 1 H), 7.85 (s, 1 H).

LRMS (Thermospray): 252.9 (MNH₄⁺).

PREPARATION 9

2-Ethoxy-4-methyl-1-benzenesulfonamide

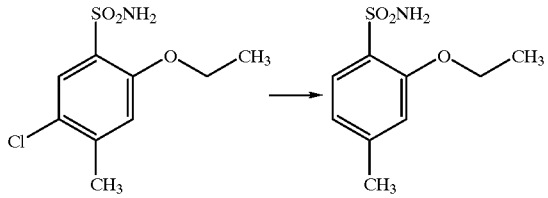

To a solution of the chlorosulphonamide from Preparation 6 (5.0 g) in ethanol (25 ml) and water (25 ml) was added Raney nickel (4 g of a 50% suspension in water) and the mixture heated at reflux for 24 hours. Hot methanol (100 ml) was added and the reducing agent removed by filtration. Solvents were evaporated and the residue crystallised from hot ethanol (2.42 g), m.p. 136–7° C.

¹H NMR (300 MHz, d₆-DMSO): δ=1.40 (t, 3 H), 2.35 (s, 3 H), 4.20 (q, 2 H), 6.75 (s, 2 H), 6.80 (d, 1 H), 7.00 (s, 1 H), 7.60 (d, 1 H).

LRMS (Thermospray): 233.5 (MNH₄⁺).

PREPARATION 10

2-(2-Methoxyethoxy)-4-methyl-1-benzenesulfonamide

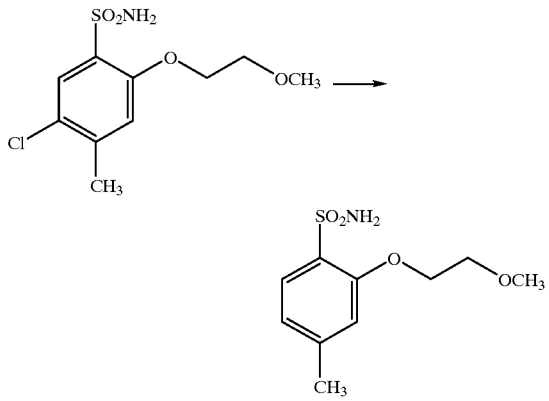

The title compound was prepared by the method of Preparation 9 from the product of Preparation 7.

¹H NMR (300 MHz CDCl₃): δ=2.40 (s, 3 H), 3.45 (s, 3 H), 3.80 (t, 2 H), 4.25 (t, 2 H), 5.20 (s, 2 H), 6.80 (s, 1 H), 6.90 (d, 1 H), 7.80 (d, 1 H).

LRMS (Thermospray): 246 (MH⁺).

Preparation 11
2-Methoxy-4-methyl-1-benzenesulfonamide

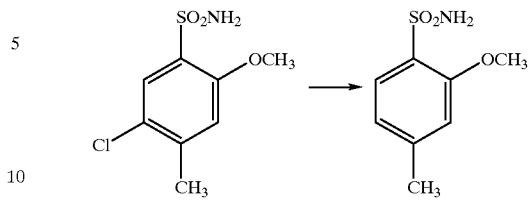

The title compound was prepared by the method of Preparation 9 from the product of Preparation 8.

¹H NMR (300 MHz CDCl₃): δ=2.40 (s, 3 H), 4.00 (s, 3 H), 5.00 (brs, 2 H), 6.80 (m, 2 H), 7.80 (d, 1 H).

LRMS (Thermospray): 219.0 (MNH₄⁺)

We claim:
1. A compound of formula I,

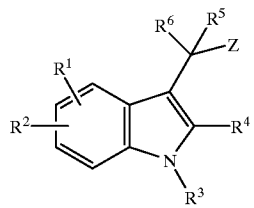

wherein $R^1$ and $R^2$ are optional substituents and independently represent $C_{1-6}$ alkyl, $C_{2-6}$ alkenyl, $C_{2-6}$ alkynyl, halogen, $C_{1-3}$ perfluoroalkyl, $(CH_2)_mAr^1$, $(CH_2)_mHet^1$, $(CH_2)_mCONR^7R^8$, $(CH_2)_mCO_2R^8$, $O(CH_2)_qCO_2R^8$, $(CH_2)_mCOR^8$, $(CH_2)_mOR^8$, $O(CH_2)_pOR^8$, $(CH_2)_mNR^7R^8$, $CO_2(CH_2)_qNR^7R^8$, $(CH_2)_mCN$, $S(O)_nR^8$, $SO_2NR^7R^8$, $CONH(CH_2)_mAr^1$ or $CONH(CH_2)_mHet^1$;

$R^3$ represents H, $C_{1-6}$ alkyl, $(CH_2)_pNR^9R^{10}$, $SO_2R^{10}$, $SO_2NR^9R^{10}$, $(CH_2)_mCOR^{10}$, $C_{2-6}$ alkenyl, $C_{2-6}$ alkynyl, $(CH_2)_mCONR^9R^{10}$, $(CH_2)_mCO_2R^{10}$, $(CH_2)_pCN$, $(CH_2)_pR^{10}$ or $(CH_2)_pOR^{10}$;

$R^4$ and $R^9$ independently represent H or $C_{1-6}$ alkyl;

$R^7$ represents H, $C_{1-6}$ alkyl or $C_{1-6}$ alkoxy;

$R^5$ represents H or OH;

$R^6$ represents methylenedioxyphenyl, optionally substituted by one or more groups selected from $C_{1-6}$ alkyl, $C_{1-6}$ alkoxy and halogen;

$R^8$ and $R^{10}$ independently represent H, $C_{1-6}$ alkyl, $Ar^2$, $Het^2$ or $C_{1-6}$ alkyl substituted by $Ar^2$ or $Het^2$;

Z represents $CO_2H$, $CONH(tetrazol-5-yl)$, $CONHSO_2O$ ($C_{1-4}$alkyl), $CO_2Ar^3$, $CO_2(C_{1-6}$ alkyl), tetrazol-5-yl, $CONHSO_2Ar^3$, $CONHSO_2(CH_2)_qAr^3$ or $CONHSO_2$ ($C_{1-6}$ alkyl);

m represents 0, 1, 2 or 3;

n represents 0, 1 or 2;

p represents 2, 3 or 4;

q represents 1, 2 or 3;

$Ar^{1-3}$ independently represent phenyl, naphthyl, or an aromatic heterocycle having 5 ring members one of which is selected from N, S and O, which aromatic heterocycle is optionally fused to a benzene ring, and which phenyl group is optionally fused to an aromatic heterocycle as defined immediately above, the group as a whole being optionally substituted by one or more groups falling within the definition of $R^1$ above; and Het$^1$ and Het$^2$ independently represent a non-aromatic heterocycle having 5 ring members one of which is selected from N, S and O, which group is optionally substituted by one or more groups falling within the definition of R$^1$ above, and is further optionally substituted by =O or =S;

or a pharmaceutically acceptable salt thereof.

2. A compound as claimed in claim 1, wherein R$^1$ represents halogen, $(CH_2)_m CONR^7R^8$, $(CH_2)_m CO_2R^8$, $(CH_2)_m COR^8$, $(CH_2)_m OR^8$ or $(CH_2)_m CN$.

3. A compound as claimed in claim 1, wherein R$^2$ is absent.

4. A compound as claimed in claim 1, wherein R$^3$ represents H, $C_{1-6}$ alkyl or $(CH_2)_p OR^{10}$.

5. A compound as claimed in claim 1, wherein R$^4$ represents H.

6. A compound as claimed in claim 1, wherein R$^5$ represents H.

7. A compound as claimed in claim 1, wherein R$^6$ represents methylenedioxyphenyl.

8. A compound as claimed in claim 1, wherein Z represents $CO_2H$ or $CONHSO_2Ar^3$.

9. A pharmaceutical formulation comprising a compound of formula I, as defined in claim 1, or a pharmaceutically acceptable salt thereof, and a pharmaceutically acceptable adjuvant, diluent or carrier.

10. A method of treatment of restenosis, renal failure, pulmonary hypertension, benign prostatic hypertrophy, congestive heart failure, stroke, angina, atherosclerosis, cerebral and cardiac ischaemia or cyclosporin induced nephrotoxicity, which comprises administering a therapeutically effective amount of a compound of formula I, as defined in claim 1, or a pharmaceutically acceptable salt thereof, to a patient in need of such treatment.

11. A process for the production of a compound of formula I, as defined in claim 1, or a pharmaceutically acceptable salt thereof, which comprises coupling a compound of formula I, in which Z represents $CO_2H$, with a compound of formula VI, $$H_2NSO_2Ar^3 \qquad \text{VI}$$

wherein Ar$^3$ is as defined in claim 1, to provide the corresponding compound of formula I in which Z represents $CONHSO_2Ar^3$; and where desired or necessary converting the resulting compound of formula I into a pharmaceutically acceptable salt thereof or vice versa.

* * * * *